US007915479B2

(12) United States Patent
Hussey et al.

(10) Patent No.: US 7,915,479 B2
(45) Date of Patent: *Mar. 29, 2011

(54) NEMATODE RESISTANT TRANSGENIC PLANTS

(75) Inventors: Richard S. Hussey, Athens, GA (US); Guozhong Huang, Athens, GA (US)

(73) Assignee: University of Georgia Research Foundation, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/511,578

(22) Filed: Jul. 29, 2009

(65) Prior Publication Data

US 2010/0186129 A1 Jul. 22, 2010

Related U.S. Application Data

(63) Continuation of application No. 11/249,919, filed on Oct. 13, 2005, now Pat. No. 7,576,261.

(60) Provisional application No. 60/704,560, filed on Aug. 2, 2005, provisional application No. 60/618,097, filed on Oct. 13, 2004.

(51) Int. Cl.

*A01H 1/00* (2006.01)
*A01H 5/00* (2006.01)
*C12N 15/09* (2006.01)
*C12N 15/82* (2006.01)

(52) U.S. Cl. ........ 800/279; 800/278; 800/298; 800/295; 800/320; 800/317; 800/288; 435/468; 435/419

(58) Field of Classification Search ........................ None
See application file for complete search history.

(56) References Cited

U.S. PATENT DOCUMENTS

| | | | | |
|---|---|---|---|---|
| 4,940,838 | A | 7/1990 | Schilperoort et al. | |
| 5,770,786 | A | 6/1998 | Sijmons | |
| 5,824,877 | A | 10/1998 | Hinchee et al. | |
| 5,981,839 | A | 11/1999 | Knauf et al. | |
| 5,981,840 | A | 11/1999 | Zhao et al. | |
| 6,051,757 | A | 4/2000 | Barton et al. | |
| 6,506,559 | B1 | 1/2003 | Fire et al. | |
| 6,593,513 | B2 | 7/2003 | Davis et al. | |
| 6,759,574 | B1 | 7/2004 | Ream, Jr. et al. | |
| 6,903,190 | B1 | 6/2005 | Williams et al. | |
| 6,936,708 | B1 | 8/2005 | Winicov | |
| 7,078,589 | B2 | 7/2006 | Hu et al. | |
| 7,576,261 | B2 * | 8/2009 | Hussey et al. | 800/279 |
| 2003/0150017 | A1 | 8/2003 | Mesa et al. | |
| 2004/0098761 | A1 | 5/2004 | Trick et al. | |
| 2004/0133943 | A1 | 7/2004 | Plaetinck et al. | |
| 2005/0091713 | A1 | 4/2005 | Atkinson | |
| 2005/0188438 | A1 | 8/2005 | Ren et al. | |
| 2006/0037101 | A1 | 2/2006 | Ren et al. | |
| 2006/0080749 | A1 | 4/2006 | Hussey et al. | |
| 2009/0012029 | A1 | 1/2009 | Hussey et al. | |
| 2009/0077687 | A1 | 3/2009 | Hussey et al. | |

FOREIGN PATENT DOCUMENTS

| | | |
|---|---|---|
| AU | 743316 | 1/2002 |
| AU | 769223 | 1/2004 |
| WO | WO 98/01569 | 1/1998 |
| WO | WO 99/07409 | 2/1999 |
| WO | WO 99/32619 | 7/1999 |
| WO | WO 00/01846 | 1/2000 |
| WO | WO 00/44895 | 8/2000 |
| WO | WO 00/44914 | 8/2000 |
| WO | WO 01/29058 | 4/2001 |
| WO | WO 01/36646 | 5/2001 |
| WO | WO 01/37654 | 5/2001 |
| WO | WO 01/70949 | 9/2001 |
| WO | WO 01/96584 | 12/2001 |
| WO | WO 03/52110 | 6/2003 |
| WO | WO 2004/005485 | 1/2004 |
| WO | WO 2005/019408 | 3/2005 |
| WO | WO 2005/082932 | 9/2005 |
| WO | WO 2006/044480 | 4/2006 |

OTHER PUBLICATIONS

Abad, et al., "Root-knot nematode parasitism and host response: molecular basis of a sophisticated interaction", *Molecular Plant Pathology,* 4(4):217-224 (2003).
Agrawal, et al., "RNA interference: biology, mechanism, and applications", *Microbiol. Mol. Biol. Rev.,* 67(4):657-85 (2003).
Alfonso, et al., "The *Caenorhabditis elegans* unc-17 gene: a putative vesicular acetylcholine transporter," *Science,* 261(5121):617-9 (1993).
Atkinson, et al., "Engineering plants for nematode resistance", *Annu. Rev. Phytopathol.,* 41:615-39 (2003).
Bakhetia, at al, "RNA interference and plant parasitic nematodes", *Trends Plant Sci.,* 10(8):362-7 (2005).
Bakhetia, at al., "RNA interference and plant parasitic nematodes", Elsevier Ltd., *TRENDS IN Parasitology,* 10(8): 362-367 (2005).
Bass, "Double-stranded RNA as a template for gene silencing", *Cell,* 101(3):235-8 (2000).
Bird, "Signaling between nematodes and plants", *Current Opinion in Plant Biology,* 7(4):372-376 (2004).
Davis, et al., "Getting to the roots of parasitism by nematodes", Elsevier Ltd., *Trends in Parasitology,* 20(3):134-141 (2004).
Davis, et al., "Nematode Parasitism Genes", *Annu. Rev. Phytopathol,* 38:365-396 (2000).
De Boer, et al., "Cloning of a Putative Pectate Lyase Gene Expressed in the Subventral Esophageal Glands of *Heterodera Glycines*", *Journal of Nematology,* 34:9-11 (2002),.
De Boer, et al., "The Use of DNA Microarrays for the Developmental Expression Analysis of cDNAs from the Oesophageal Gland Cell Region of *Heterodera Glycines*", *Molecular Plant Pathology,* 3:261-270 (2002).
Diehn, et al., "Problems that can limit the expression of foreign genes in plants: lessons to be learned from B.t. toxin genes", *Genet. Eng. (N. Y.*), 18:83-99 (1996).
Doyle, et al., "Meloidogyne javanica chorismate mutase 1 alters plant cell development", *Mol Plant Microbe Interact.,* 16(2):123-31 (2003).

(Continued)

*Primary Examiner* — Medina A Ibrahim
(74) *Attorney, Agent, or Firm* — Pabst Patent Group LLP

(57) ABSTRACT

Compositions and methods for providing nematode resistance are provided. One aspect provides transgenic plants or cells comprising an inhibitory nucleic acid specific for one or more nematode esophageal polypeptides. Other aspects provide transgenic plants or cells resistant to at least two different root-knot nematode species.

11 Claims, 7 Drawing Sheets

OTHER PUBLICATIONS

Fire, et al., "Potent and specific genetic interference by double-stranded RNA in *Caenorhabditis elegem*", *Nature,* 391(6669):806-11 (1998).
Fraser, et al., "Functional genomic analysis of *C. elegans* chromosome I by systematic RNA interference", *Nature,* 408(6810):325-30 (2000).
Gao, et al, "Defining a plant-parasitic nematode: a profile of putative parasitism genes expressed in the pharyngeal gland cells of *Heterodera glycines*", presented at the Fourth International Congress of Nematology Programme and Abstracts, Jun. 8-13 , 2002, poster session, 1 page.
Gao, et al., "Characterization and Developmental Expression of a Chitinase Gene in *Heterodera Glycines*", *International Journal for Parasitology,* 32:1293-1300 (2002).
Gao, et al., "Identification of Putative Parasitism Genes Expressed in the Esophageal Gland Cells of the soybean Cyst Nematode", *Heterodera Glycines., Molecular Plant-Microbe Interactions,* 14:1247-1254 (2001).
Gao, et al., "The Parasitome of the Phytonematode *Heferodera Glycines*", *Molecular Plant-Microbe Interactions,* 16:720-726 (2003).
Gheysen, et al., "Gene Expression in nematode Feeding Sites", *Annual Review of Phytopathology,* 40:191-219, with tow figures and a contents page (2002).
Gonczy, et al., "Functional genomic analysis of cell division in *C. elegans* using RNAi of genes on chromosome III", *Nature,* 408(6810):331-6 (2000).
Guo, et al., "par-1, a gene required for establishing polarity in *C. elegans*1 embryos, encodes a putative Ser/Thr kinase that Is asymmetrically distributed", *Cell,* 81(4):611-20 (1995).
Huang, al., "A Root-Knot Nematode Secretory Peptide Functions as a Ligand for a Plant Transcription Factor", *Mol. Molecular Plant-Microbe Interactions,* 19:463-470 (2006).
Huang, et al, "Engineering broad root-knot resistance in transgenic plants by RNAi silencing of a conserved and essential root-knot nematode parasitism gene", *Proc. Natl. Acad. Sci.* U.S.A., 103(39): 14302-14306 (2006).
Huang, et al., "A Profile of Putative Parasitism Genes Expressed in the Esophageal Gland Cells of the Root-knot Nematode *Meloidogyne incognita*", *Molecular Plant-Microbe Interactions,* 16(5):376-381 (2003).
Huang, et al., Root cell proliferation induced by a secretory root-knot nematode signaling peptide, Abstract in Aug. 2004.
Huang, et al., "Root cell proliferation induced by a secretory root-knot nematode signaling peptide", *APS Annual Meeting Abstracts of Presentation,* 94(6): S42-S43 (2004).
Huang, et al, "Two Chorismate Mutase Genes from the Root-Knot Nematode *Meloidogyne Incognita*", *Molecular Plant Pathology,* 6:23-30, (2005).
Huang, et al., "Use of solid-phase subtractive hybridization for the identification of parasitism gene candidates from the root-knot nematode *Meloidogyne incognita*" *Molecular Plant Pathology,* 5(3):217-222 (2004).
Hussey, at al, "Secrets in secretions: genes that control nematode parasitism of plants" *Molecular Plant-Microbe interactions,* 14(3):183-194 (2003).
Hussey, at al., "Secrets in secretions: genes that control nematode parasitism of plants", *Br. Jour. Plant Physiology,* 14(3):183-194 (2002).
Hussey, at al., Nematode Parasitism of Plants, The Physiology and Biochemistry of Free-living and Plant-Parasitic Nematodes, CAB International, Chapter 9:213-243, (1998).
Hussey, et al., Root-Knot Nematodes: *Meloidogyne* Species, Plant Resistance to Parasitic Nematodes., CAB International, Chapter 3:43-70 (2002).
Maeda, et al., "Large-scale analysis of gene function in *Caenorhabditis elegans* by high-throughput RNAi", *Curt Biol.,* 11(3)171-5 (2001).
McCarter, "Molecular approaches toward resistance to plant-parasitic nematodes", in *Plant Cell Monographs,* vol. 15/2009, Springer Publishing: Berlin/Heidelberg (2009). Epub. Dec. 2008.
NAQVI, et al., "The fascinating world of RNA interference", *Int. J. Biol. Sci.,* 5(2):97-117 (2009).
Opperman, at al., Advances in Molecular Plant Nematology, Bioengineering Resistance to Sedentary Endoparasitic Nematodes, In Advances in Molecular Plant Nematology, F. Lambert, C. de Giorgi and D.M. Bird eds. (New York Plenum Press), pp. 221-232, (1994).
Piano, et al., "RNAi analysis of genes expressed in the ovary of *Caenorhabditis etegans*", *Curr. Biol.,* 10(24):1619-22 (2000).
Puthoff, et al., "Arabidopsis gene expression changes during cyst nematode parasitism revealed by statistical analyses of microarray expression profiles", *The Plant Journal,* 33: 911-921 (2003).
Ray, et al., "Trans-splicing of a Meloidogyne incognita mRNA encoding a putative esophageal gland protein", *Mol. Biochem. Parasitol.,* 88:93-101 (1994).
Rosso, et al., "Application of RNA Interference to Root-Knot Nematode Genes Encoding Esophageal Gland Proteins," *Molecular Plant-Microbe Interactions,* 18(7):615-620 (2005).
Sim and Todd, "First field observation of the soybean cyst nematode in Kansas", *Plant Disease,* 70:603 (1986).
Smith, et al., "Total silencing by intron-spliced hairpin RNAs", *Nature,* 407(6802):319-20 (2000).
Thomas, et al., "Size constraints for targeting post-transcriptional gene silencing and for RNA-directed methylation in Nicotiana benthamiana using a potato virus X vector", *Plant J.,* 25(4):417-25 (2001).
Todd, et al., "Field response of soybean in maturity groups Ill-V to *Heterodera glycines*in Kansas" *Supplement to J. of Nematology,* 27:628-633 (1996).
Urwin, et al., "Ingestion of double-stranded RNA by preparasitic juvenile cyst nematodes leads to RNA interference" *Mol Plant Microbe interact.,* 15(8):747-52 (2002).
Wang, et al., "A parasitism Gene from a Plant-Parasitic Nematode with Function Similar to CLAVATA3/ESR (CLE) of *Arabidopsis Theliana*", *Molecular Plant Pathology,* 6:187-191 (2005).
Wang, et al., "Signal Peptide-Selection of cDNA Cloned Directly from the Esophageal Gland Cells of the Soybean Cyst Nematode *Heterodera Glycines*", *Molecular Plant-Microbe Interactactions,* 14:536-544, (2001).
Wesley, et al., "Construct design for efficient, effective and high-throughput gene silencing in plants", *Plant J.,* 27(6):581-590 (2001).
Williamson, et al., "Nematode Pathogenesis and Resistance in Plants", *Plant Cell ,* 8:1735-1745 (1996).
Wrather, et al., "Soybean Disease Loss Estimates for the Top 10 Soybean Producing Countries in 1994", *Plant Disease,* 81:107-110 (1997).
Young, "Managing soybean resistance to *Heterodera glycines*", *Supplement to the Journal of Nematology,* 30:525-529 (1998).

* cited by examiner

Figure 1A
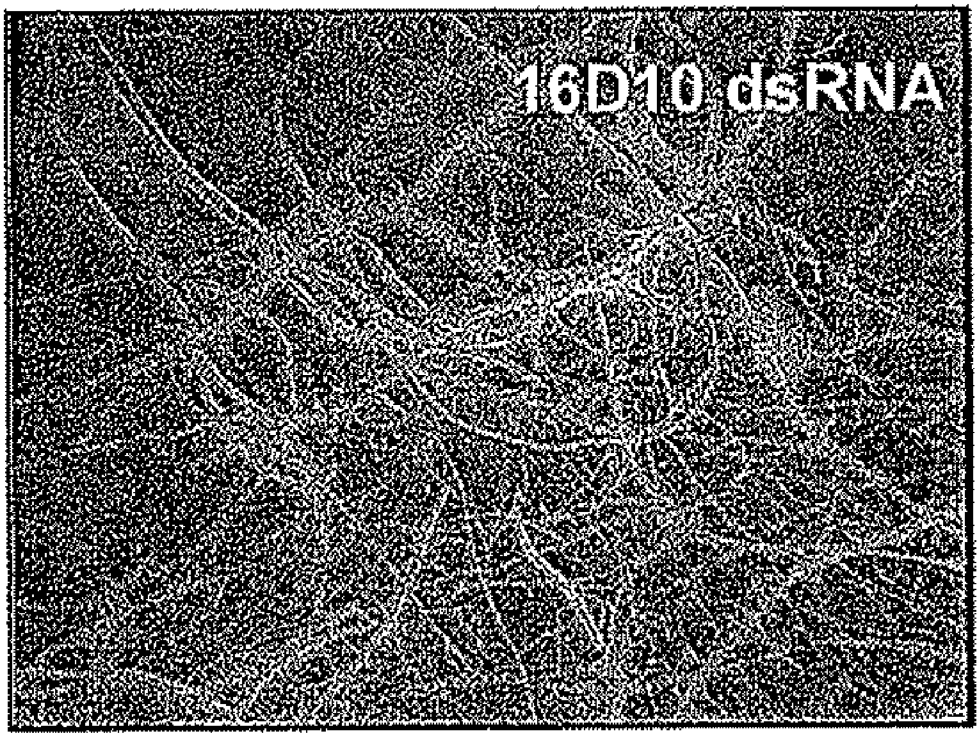
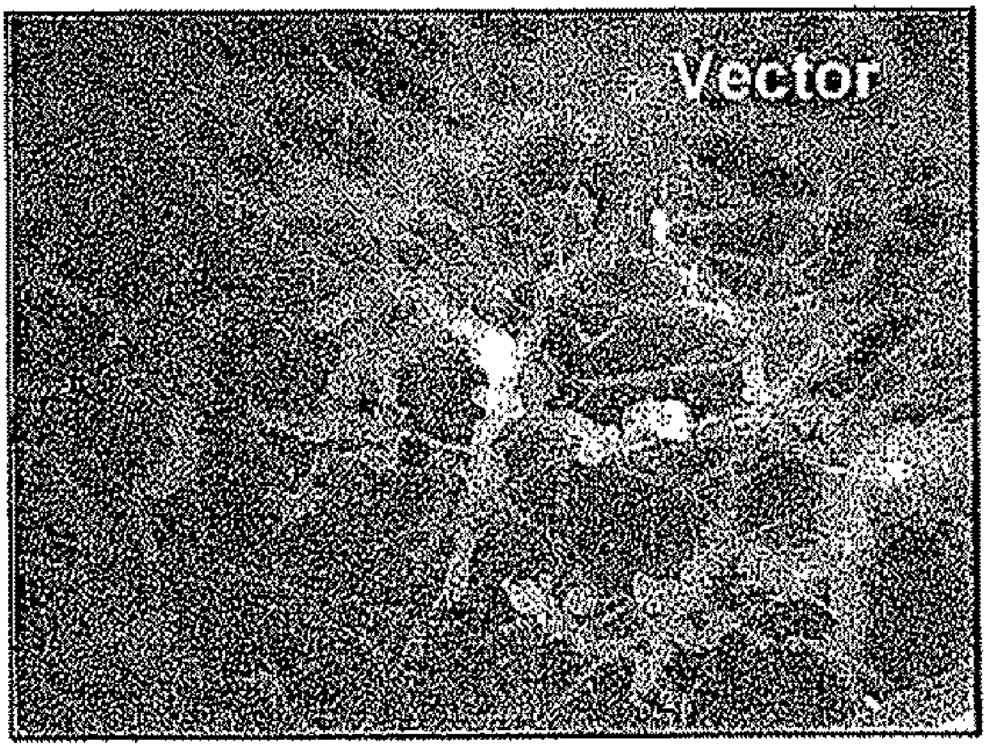
Figure 1B

*35S::16D10* Vector

SEQUENCE LISTING

<160> NUMBER OF SEQ ID NOS: 79

<210> SEQ ID NO 1
<211> LENGTH: 817
<212> TYPE: DNA
<213> ORGANISM: Meloidogyne incognita

<400> SEQUENCE: 1

```
gagaaaataa aatataaatt attcctcaaa aataccataa aggttagcca atattaattc     60
ttttgaaatt ttctttgctt ccataaatta aaaaaaattg tttttaagtg agggaatgtg    120
gattaagcat ctttcttatt tttaaaattt ttgatagagt gtagcgacag tcaatcaaaa    180
tattttgatt tttttaaagt taaaaattaa ggatgataaa gaagtttaaa atgtaggtgg    240
aaatataagt ataccgaaaa acatctttta tttttaagtt taaacaagca gtaaaacttt    300
gtctggtttt atcaccgggc aactgtaagg gaagctttaa taaaaatttt gtaagatacg    360
aaaatcattg tccccagtag cttgagtgat cgaagcgcct ggttgccatt aagttttttg    420
cttgagactt atataacaag tatatatcaa accggattat aaagttaaag aacagaaaaa    480
atttcacgga ataaatattg gctaaccact caatttattt aattattctt caatcaaaaa    540
atgtttacta attcaattaa aaatttaatt atttatttaa tgcctttaat ggttacttta    600
atgcttttgt ctgtctcatt tgtggatgca ggcaaaaagc ctagtgggcc aaatcctgga    660
ggaaataatt gaagaaaaat gattgaagaa aaacgtttaa attaaacgat aaatgggaaa    720
taatggaatt taaattaagc taattttgat ggtttccttt gttaatttca acataaaatt    780
aattgaattt actgaataaa attatatctg aaaaaaa                             817
```

<210> SEQ ID NO 2
<211> LENGTH: 364
<212> TYPE: DNA
<213> ORGANISM: Meloidogyne incognita

<400> SEQUENCE: 2

```
gagaaaataa aatataaatt attcctcaaa aataccataa agttaattat tcttcaatca     60
aaaaaatgtt tactaattca attaaaaatt taattattta tttaatgcct ttaatggtta    120
ctttaatgct tttgtctgtc tcatttgtgg atgcaggcaa aaagcctagt gggccaaatc    180
ctggaggaaa taattgaaga aaaatgattg aagaaaaacg tttaaattaa acgataaatg    240
ggaaataatg gaatttaaat taagctaatt ttgatggttt cctttgttaa tttcaacata    300
aaattaattg aatttactga ataaaattat atctgaaaaa aaaaaaaaaa aaaaaaaaaa    360
aaaa                                                                 364
```

<210> SEQ ID NO 3
<211> LENGTH: 108
<212> TYPE: DNA
<213> ORGANISM: artificial sequence
<220> FEATURE:
<223> OTHER INFORMATION: 16D10 plasmid

<400> SEQUENCE: 3

```
ctcgagggca aaaagcctag tgggccaaat cctggaggaa ataattgagg taccatcgat     60
tcaattattt cctccaggat ttggcccact aggctttttg cctctaga                 108
```

<210> SEQ ID NO 4
<211> LENGTH: 566
<212> TYPE: DNA
<213> ORGANISM: artificial sequence
<220> FEATURE:
<223> OTHER INFORMATION: 16D10 plasmid

<400> SEQUENCE: 4

```
ctcgagcctc aaaaatacca taaagttaat tattcttcaa tcaaaaaaat gtttactaat     60
tcaattaaaa atttaattat ttatttaatg cctttaatgg ttactttaat gcttttgtct    120
```

-continued

```
gtctcatttg tggatgcagg caaaaagcct agtgggccaa atcctggagg aaataattga    180

agaaaaatga ttgaagaaaa acgtttaaat taaacgataa atgggaaata atggaattta    240

aattaagcta attttgatgg tttcctttgt taatttcggt accatcgatg aaattaacaa    300

aggaaaccat caaaattagc ttaatttaaa ttccattatt tcccatttat cgtttaattt    360

aaacgttttt cttcaatcat ttttcttcaa ttatttcctc caggatttgg cccactaggc    420

tttttgcctg catccacaaa tgagacagac aaaagcatta aagtaaccat taaaggcatt    480

aaataaataa ttaaattttt aattgaatta gtaaacattt ttttgattga agaataatta    540

actttatggt atttttgagg tctaga                                         566


<210> SEQ ID NO 5
<211> LENGTH: 694
<212> TYPE: DNA
<213> ORGANISM: Meloidogyne incognita

<400> SEQUENCE: 5

gatcaaacaa tctcctcaac aactaaaaaa actcaaaaaa caccccaaaa ccaaactaaa     60

aaatcaaaaa tgtccatctt cctcacttct gctcttctaa tcatttcatt aatcgctatg    120

accgagggag caggcgatcg aagcgcttca acctctactg gttgtacaac ctattttgga    180

atgctagatc atgcggatac caaggaaaat aacaaaagaa aaactttcaa acccaacgat    240

aaaaccatat ccaacacttt gcaagtgatt ggtgggacaa agttcagcaa tacctcggtg    300

gcgttggttg tcggtgatga ggtgttatgt atggctaaga caggaggttc aggcgattgc    360

ggaatgcgct acgatgcgtt gactggatca atgaaattta tcatttctga taatattatt    420

gttgaggttc catttgaagg cgtttttttc ttcaccgaca acaagtgtgt catccagctt    480

gtaggctacg atattaaaac taatataact cttctcaaaa ttaatgatgt cgacttcaaa    540

attgtcccta ctgataagaa aatttccccg aaggcttgta ctatgaaaat gtgagggaaa    600

aaagtaaaga aaatgtgtaa atatggaagg ataaaaacta aacaaaaaag aatgtgaagt    660

aagaaaaaaa aaaaaaaaaa aaaaaaaaaa aaaa                                694


<210> SEQ ID NO 6
<211> LENGTH: 776
<212> TYPE: DNA
<213> ORGANISM: Meloidogyne incognita

<400> SEQUENCE: 6

ggatttaaaa aattaattta aaaaaagtga aaaattcaat taaaattaaa aaatattttt     60

caatgaattt attttctatt tttttatttt tatttccaat cgggtttatt tgggctgaat    120

gtagcggaga ttgttctata gagaaccaat ataattataa atgtgaggat agaagtgaat    180

tttgtgaaga atggggaaaa tactgcgaaa atgtctttct tcacaaatgt gtaagaaagg    240

cttgtccaaa gaaatgtaaa gtttgtcata gttctggtga agaacctaaa ccaaatccta    300

caactataac aacggcatca acaataacaa caccattagc aacaacacct caaaactcag    360

cagttacttc ggcaacctca aaaagtgcta ctccatcaaa aacttattca accgagacaa    420

ccgaatgtgc taacacaact actgaggaat atgaagcaac tattgaggaa tatcaaacaa    480

ctacagaaga atatgaagag gtaacaaccc ctataattac aaccaccaat ccaacaactt    540

atttattaat gactacaata gttgaagaaa ttagtgacga cgaattcaaa gacgcaaaga    600

agatgaaatg taaatcatgt aatgcaaaaa ggaagaaatt ggctgaaatt tatgacaaat    660

attatccgaa agttaagatt catgctaaat tgtaaattat gatggaaaat gtttttgaat    720
```

-continued tgtgaaaata aaaatttaat taacccaaaa aaaaaaaaaa aaaaaaaaaa aaaaaa 776

<210> SEQ ID NO 7
<211> LENGTH: 999
<212> TYPE: DNA
<213> ORGANISM: Meloidogyne incognita

<400> SEQUENCE: 7
gatagcacag atctattttt agattttttt agctttttag aaaattttaa tttaaaaatt 60
atgtttattc ttccaaaacc tttttatctt ttaattttac taattatttc aacaattttc 120
cttttatttt taattcttcg tttgccttca atttcttacc aaacaaatca atgtcaacat 180
ttatgggact cttccgagtg caaaaattta aataattctt taaattggca tccaataact 240
tgttttattg acggaaagca aaaaagagtt ccctgtcttc aacaaaatga tttaaaagaa 300
gtttatcttc cattcaattc atttttgaaa aaacaatttg atttgtatgg agagactgac 360
aaaagcattt ttttaatttt aaaatttatt tttaacaaaa tttgcggaca gataaaattt 420
gtccgcaaaa tatttgcgga caaataattt tttttgttgt taggcttttt tagggtattt 480
ttttctacaa ttttttggag ttttttttcta caattttttg gagttaattc taaattataa 540
ttttattata tattttataa ttttaaaatt tttttctttt taagaaaaca attcttttga 600
ttattttact tcaaacattc ctccacgtct ttttaaaaat aaaaataaaa tggtggctgc 660
aaatccaatt gaacaattta gcaatgtggc tattcgtcaa agaataaaat gtttaaaacc 720
tgaaaatgga ttaccaatga gcgttcaatg gagtccaatt ccctacttct atcctgttca 780
aatactccaa tttggctttg attattttat gagaaatcga acagaacaga ggaaattaat 840
tgaaagaagg ttatcaaaca aagatgattt cttggtacta aaaagtggag agaaagttag 900
cgaattttca actttttttct gatttgccat tttacctttt ctgcaaaatt gaatcaatgg 960
atgcttcctt gtaatatttt tgagaagatt gggggaatt 999

<210> SEQ ID NO 8
<211> LENGTH: 785
<212> TYPE: DNA
<213> ORGANISM: Meloidogyne incognita

<400> SEQUENCE: 8
gacaataaac gatccaattt cctaaaattt ttttaaaaatt tttaaaattt attttatgcc 60
cctttttgtt tatttaaaca aatttgcttg attattaatg ccaaaattaa ttttattatt 120
ttatttaatt atttatggaa ttttattgtt aataagttta agtgaagcat ttgggtttgg 180
tggaggatgt ggatgccctt gtatgccgca accatgtatt ccacaaccac ctccaattgc 240
tttaccttct ctatgtttcc ctcaaatcca attgccctgt ccccctccat cttgtggatg 300
ttgtggtaga agaaaaagag aaagtggagc ttcagcatta ttaacagcag tttcaacaaa 360
gtcgggaatt aaaagaattg gagaagaaaa aaatcattgt aataatccac acattaaaag 420
aattatttta aagaatttaa ttattggaga ttgggttggt acaagaaatg caatatattc 480
agaattaaga gctaaattag gggggaatta tataattaat tgtgctcatg ccccctcatt 540
tgcgtattct ggtgattctg tgattgatta ttgtgtggat ggacatcagg caataacttg 600
tgcagtcttc aaaattcaat gagaataaaa tcagaatgaa ttctattttt ttaataaata 660
taaaaatttt tataatatat tttgagcatt ataaatattt ataaattagt tttttttgat 720
aaattaattt gaaaatgtat aaattagttt ttactcaaaa aaaaaaaaaa aaaaaaaaaa 780
aaaaa 785

-continued

<210> SEQ ID NO 9
<211> LENGTH: 864
<212> TYPE: DNA
<213> ORGANISM: Meloidogyne incognita

<400> SEQUENCE: 9
gacgcaattc cattttgcgt tcaatcaatt tagaaaaagg ctggaaataa tgattcatca 60
acaactttat tattagcgct tagtgttccg ggctttcatt tcaacagaga aatttcaaat 120
tcacctattt ggagcttgga tcagttcttc tatcgacttg tagtcctaac ctatactaaa 180
aattttttaa attaaccaca atggaacttg ctattaacag tcgattgtta tcatttttgt 240
ctttattcct attcatattt cctttaaatg ttgttgctca acggcatcgt tacccacaca 300
atcaaggaaa ttatttcagc agacaaaagc tgcaagaaat acagaaggag gaaaatgagg 360
ctgaaaattc tttaccaaaa atcttttgcg cgcatggagc ttcagtagcc ggccgttgcg 420
tatgtgatca tggttgggcc ggtactaatt gccagcggga aatgcattgt gctacttttg 480
agcgaaatgc taatggaagc tgcccagtct gtcagcccaa ttttcaaggg gataagtgcg 540
aatatattga atgccaaaat ggaggccaag aatcattgga aactcagaat tgtaactgcc 600
caaagcctta ttctggccgt ttttgtgatg aattactcac aggaaatgtc tactactact 660
ataactctaa agtagcaacc cttggtcctc ttggacttat ttctgttata ccaatgattt 720
gtctttatgt tttatgtgaa aagatttgca aggaaaagac aagtgagacg gattgagaaa 780
acttggaatt tacagagcag taaaactgtg aatcctgctc atattgaatt tctattaagg 840
gaaaaaaaaa aaaaaaaaaa aaaa 864

<210> SEQ ID NO 10
<211> LENGTH: 977
<212> TYPE: DNA
<213> ORGANISM: Meloidogyne incognita

<400> SEQUENCE: 10
gaccttaatc aataaaaaat attttttaca taaaaatgtt ttatttattt tattttaaat 60
tatttttatt ttccttaatt tctttaaata aagttaatgg attttgtatg aagactattt 120
gttctgcgga caccgattct cgacaccctg taaatcgagt aatcggtatt ggttctgatg 180
gaattagtgg ggaatataaa gctttgagac gaaatgatca aattgttgaa gctgtagatt 240
taagttgtag agaaggaagt tttgtttatt ctccctttga aggggaaatt tctgcttgga 300 gacctttga tggaaatggg caagatgaaa ttagaacgga tgaaaataag aagaatacag 360
atggatgcag acctgaccga ggagttagaa ttgatggaaa aggacaatgg cagggatatc 420
acgtccttat tggctctgtt cgtttattcc gttacagtgg acatgttaat gctggacaaa 480
aaattggtgt atctttggat attgaatgtg aattgaaatt aaataaacaa aagatgaata 540
aacgtcctcg aaaagaagaa aattttgtca gagtttattt acacaaggaa ggacgtccaa 600
ttgatccaac acatcattta attgattgta tgtgtataaa ccaagtctgt gagacaaaca 660
gaattaatgc tttggaagga ccgttattta aatttgacag tcgttttaac ggtgttagag 720
gatgggaaat taaatgtcca gatattcaac aaattgaaga agaaaattct tcagaagaag 780
aggaagaaaa gaaaaaagaa gaaaataatt taaatgaaga atggggaact ccaaaattta 840
ttcacctata gaaggggaat tggttggaag aattagagtt aatagtgaac ctggggcaca 900
gacttatact ggatgtacta atgaaggaat atttatggtt ggggctggaa agtggaatga 960
ttatgaagtt cgaattt 977

<210> SEQ ID NO 11
<211> LENGTH: 1339
<212> TYPE: DNA
<213> ORGANISM: Meloidogyne incognita

<400> SEQUENCE: 11
gttcatttaa aaatttttc ctaaaaaact tcaaaaaagc aacttttatt gcgtaaatga 60
aagaaaatct gtttaaaaag agccttatag gcctattttt gttgttagca ttcaatttta 120
ctgaagctaa ggactctgga gagaatacta gtcttgaagc tagtttgaaa ccaactaaaa 180
gtattgaaaa tgcttcccta gaagaaaaga atcaaaaaga agaaaatgga gtaacattcc 240
cggcagaagg tcatgaaatt gtcgaaacaa aaaaagaaat caactcacca gaagaggtga 300
cagattcaac taaaggacag gaaaattccg aggatcgtaa agtgacaatg aatggtgatg 360
agtctgaggc cgataaatta aacaatgaaa atgttgaggg tgaagaaaag aaagcaactg 420
aaaacaagaa tgaagttgag gaaaaagaag ttttagagga tgagaagaca aaagaagagg 480
aagataaaat tagcgatgag cctgtgaaga caaaggaaat gaaatcaaca aacaatgata 540
aggaagttga agatttgaaa gaagaggaag agaaagtcga ggtaaaaggt aacaaggatg 600
aagaagaaaa taaggaagag aagaaggaag ataagaagac aaaggatgaa aaaaaggttc 660
cagaggttat tgagggagag aagaaaacac ccaaggaaaa ggaacacaaa agccattggt 720
ttatggacaa atttaaacat gctttctgtt tcataactca ttacttcttt tgtccatcta 780
actctgcaga aaaaggcaaa gaatcccatc atgaaggaaa agaatcacac cgtggaaagc 840
gtcttaactc tgattttagt tctttaagca gtgatgagga aatgattgag aattttgaaa 900
atgcccacga atttagtgaa gaaattgaag aaaatgggga atttaaagct aaaatgaatg 960
ttggtgcaac atacttcaaa gctgagacag ataattctgg aaagatgcgc ggcaaaattg 1020
aaaaatttaa tgctgaaatg cataattgaa aagattgtaa ggatggtggg tgtgctgatg 1080
agtaaaacaa aaaaaagcaa tccgatttta ttctaaattt tattttttaa agtgattcca 1140
acaagtgatt ccattaaccc ctcaaattta tttaaaaaaa cgaaatttta aaagttctgg 1200
atttatgtcc caaaaattgt acaaattatt caaacaaact caatggtttt ggacattata 1260
ttttttttatt attttctaac aatttttatt aatgttgaag taaaagatta attcaaaaaa 1320
aaaaaaaaaa aaaaaaaaa 1339

<210> SEQ ID NO 12
<211> LENGTH: 762
<212> TYPE: DNA
<213> ORGANISM: Meloidogyne incognita

<400> SEQUENCE: 12
attcttaatt tatttaaaga atttattctg catgatgaaa ttaattaata ttttattttt 60
attttttgtt attttactga attctatggc tttcggaagg ttttctttat ttttggaaaa 120
atcaaaattt caattgaata ttttgttttc attccaagat tttctcacac agatcccgct 180
tagtgtgaga tatcggataa agcttcataa cctctacaat tttaagatat ccacattact 240
ccgtccaaat tcccttatat ctcctttgat ccctacaaat ctaccgatat cccctccacc 300
gatattttcc ttttccgaac cttaacttcc gatcaatccg ctatctggac aaatcgttat 360
tcctctaaac aagaatttat gcttttaaat gtataaaacc aatctttaat attcttcaaa 420
aaaattttca gtccttctct caattcagtg cgtgctaaac gtcaaggctg gggaggatgg 480
ggttggaacc ctcaagttca aacagatatt gatcgtcttc gtattgataa agacaaactg 540
cgattagata tggaccgttt aagactagat caggatagct cttggggatg gggaaaatga 600
gagaatcaaa cgactaattt aagtgtaacg atttttaatt aacgatttat aaattaataa 660
atacttgatt gatacacaat ttagataatt taaaataaat tttattaaat gataaaatta 720
aattgccgtt ttaaaaaaaa aaaaaaaaaa aaaaaaaaaa aa 762

<210> SEQ ID NO 13
<211> LENGTH: 778
<212> TYPE: DNA
<213> ORGANISM: Meloidogyne incognita

<400> SEQUENCE: 13
gaccatcaaa tcatctcctc atcaactaaa aatccctaaa aacaccccaa aacatccata 60
aaaacaacca cgaaaatggc caccttttc actttaccc ttctaatcat ttcaattatt 120
gccacaactg agggaatgaa tactaatcga agtgcttcaa cctccgattc tctcaaagcc 180
caaaaggatt gtaaagtgat atatggcatg tttgtgcctg tagcagggtc aaaaatgcat 240
ggagacgcca aaagcgcaat gaagccaaac aatccaagtc tctccaataa attaattgta 300
tcaggtggca actcaaaata ttcagtgact ttacaggttg aaaaccagcc gaagtgtgtt 360
gcccaaaatg acggaaaccc tgtagaatgc caaattcaag gagacaaact ttcaggaaaa 420
ttgatttatg atattgaaaa cggcccttct gtcaacgttc ccttcaaaga caccccaatc 480
tttgttggaa ataaatgcga aattgttttt gtagactacg ataaggacca caaattaact 540
cttcttatga ataaagtaaa gctgatgatt gagccgactg aaaagcaaat tgtaaaggct 600
tgtggagtga aaaattagat ggaaaaatga tatatgaatg aatgaatgtg agagggaggg 660
aaagaaaaat atttttaaaa ttgaagaaag cattcaaaaa aattaaaaaa aaacaattct 720
tcaaataata taaccttaaa atttctgata aattatgttt ttacaaaaaa aaaaaaaa 778

<210> SEQ ID NO 14
<211> LENGTH: 757
<212> TYPE: DNA
<213> ORGANISM: Meloidogyne incognita

<400> SEQUENCE: 14
gccatcaaat aatctcctca acaactaaaa aactcaaaaa aacaccccaa aacaactcta 60
aaatggcggc tctcctcttc acttctaccc ttctaatcat ttcattggct tttattgcca 120
tagctgaggg agcaggcgat cgaaatgcat cagcttcaag ccctggttgt atgcaggttg 180
caacccttat tcatataggg gaaattcgcc cagcaaaagc aaacaaacca ggtgtacaaa 240
atactctaaa aatgtctgga aatgttcaaa cattcaaaac tactcaagtg acattacaag 300
tagctgggca agagccttgt accgttaaaa ttaataatgg cgaaaccaaa tgtaaaataa 360
ccggagatga attaaatgga aaattaattt tcaaaactga aaaaggaact gaaatttctg 420
cttatttcga actggttcca ttattttctg aaaataagtg tgttattgaa cttgacactt 480
ataacaagga aacccatgaa actaaactta aaattaatgg aaataatttt atgattaaaa 540
agaaggaagg taatgtgtca attaagtgtg gtggaagagc taatactgtt taaattttaa 600
aagtgtgaat tgaaagagga agagaataaa caaatgtgaa gatgagaaaa aaatattttg 660
aagaaagcat tataaaaata ttaaaaaaaa ttaattcttc aaatttttat ttgatttttg 720
aataaattat tttattaaaa aaaaaaaaaa aaaaaaa 757

<210> SEQ ID NO 15
<211> LENGTH: 1091
<212> TYPE: DNA

<213> ORGANISM: Meloidogyne incognita

<400> SEQUENCE: 15
gctcattaat tagttaaaaa atttaaaaaa taatttaaaa aatgaaaatt tattttaatt 60
taattgtttt tctatttatt ttaaattttt attttgtcga attggcaaaa aggaaggcaa 120
cggatactga gattcctgag caaaataaaa agcaaaatac aagcaaccat gcccatcaac 180
aattaactcc ttcttcttca aatgctgata atgagaagca aggaaatctt tcctctgaag 240
cttcaaatat tcgaggaaaa aatattctgc atgatcagtc tgctattaaa aacaattcgt 300
taactaatca acaattagga gcctcctctt ctaatgctgg gcaacagaga aataataatt 360
cggatctttt aaaattaaca attataaatc atttgttatc ccatcgccaa tttaatgcct 420
cttcttcaaa tgctggtcaa cacaaaaata ttccctccga aaatctaaat tttcatcaaa 480
aaactattcc aattgctact aaaaataatt tgttccccaa tcagcaattt attgcatctt 540
cttcaaatga tcttgatttt caacaaaaaa atattccata tggaactaaa aagaaggtgt 600
tacatcaatt tatgccatct tcttccaatg ctaataaacg caaaaatagt tccacggaat 660
atttaaaata tgcaattaaa aatagatttt tatctaatca gccatttgat gacgacattt 720
atggtaaaaa gaaaaatgtt tccccggaat atcaaaatat tcaacaaaaa aatcttccat 780
atgtccaata tgctattgat aataatttga aattgccaat tccaaaaaat cctaaagcac 840
ttccatatga tttgtctaaa tacgcattta acttccccaa tatgaacaag aaaaatattt 900
atgaaggagc atatgatcct tattatatta attttcaaca ataacagatt tggctaataa 960
aacgttggaa aacgactaag aagttataca tttgacataa attaaataaa taaaattaaa 1020
ttactattat aaaattgtta attatcgtaa taaaattttt taactcaaaa aaaaaaaaaa 1080
aaaaaaaaaa a 1091

<210> SEQ ID NO 16
<211> LENGTH: 1282
<212> TYPE: DNA
<213> ORGANISM: Meloidogyne incognita

<400> SEQUENCE: 16
ctagtcagtc atttaaaata atttaatatt cctctaaaaa tccctaaatt aatttaaata 60
tttctttaat caatttttct tcaaaaaatt taaagaagga aatgttttta caaaaacaat 120
tattgttttt ggttgttctt ctattagcct tttctcttgt aaagggagta accgagaata 180
agaataaaag cgaaataaaa aatgaaacaa ccacaaaagt aattcaaaca tcaactggag 240
gttatgatga taacgaaaaa gcagactatg gcgatttggc tgcagaattg gctaaacttg 300
ttgaggagga agatgaatta aataaaaaga agaatgcttt gagttcggag aatggaaata 360
aaaatagcac aggaaagcct tatattcaaa aagataaaag taaaaaatat ttggaagaag 420
ataaaggaaa atatgaggaa agaaattcta gaaataaata tgaaaactcg gatgaaaccc 480
atgaaagtga atcaggttca agttcggatg aggatttaga tgaagataat ttagaaagat 540
tgccagggcc ttcgccacac aatgaaggaa tttctaggcg aagagttgaa aaggaaaaag 600
gtggagaaga tgaggaggag gaagaaaaag agcaagaaaa ttctaatgat aaagaagaaa 660
gaaagaagaa aaggaacacc aaatataatc caaaagatga gagtgaggaa gatatttctt 720
ttgatggtca aatacctaaa agtgtacgta aattacttaa acaattagca gctggtggaa 780
agaatcctgt aattatacct ttaattataa ataacaacaa tataccgaat cgaagagaag 840
atgagtctga ggaatggaat aaaaaaagac atgggagacc tcatagatta aatgattgga 900

```
ataatccgtt tcctccattc tttcaatctt caatgtttca accaccaatg tttcaaccac    960

ctatgtttcc accacaacag ccaccttttg gtggccctcc aacatttgct cagcacttaa   1020

tcttcctgga gggcctctcg gaggaggtct tgctggcagt cttcccaaca caaatccatt   1080

tttatcacaa ctaaatcgtg gtgtaagtcc taatcaattt cccaatcctc cctctaatca   1140

cgttccacct tttgggcaac aaaatcaatt ctatcctcct caacaacaac aacaaaatca   1200

agtcaaccca cagggagcag atggcaatga tgtgaaaaaa gtgaattaaa caaaaaaaaa   1260

aaaaaaaaaa aaaaaaaaaa aa                                            1282
```

<210> SEQ ID NO 17
<211> LENGTH: 1228
<212> TYPE: DNA
<213> ORGANISM: Meloidogyne incognita

<400> SEQUENCE: 17

```
gatcgtcatt cttgtaaact aaaaatcttc aaacttcaaa aaatattcct taaacttctt     60

cacaaaaaga attgaaaaat gttattaaaa ttctttctcc cattattgct tttggttacc    120

cttatctatt tggggtgttc tgaggaggat aaggaagaca ttgcaaatgg tcctcaggaa    180

tctgagaatc aggttgatca agaattggtt agattgaaaa gagatgatga agaagaggag    240

ggagagaagg ctgaagatga agagaagcct gaagaggagg gagaaaaggc cgaagatgct    300

gagaatgcag aaggagatgc tgataaagga gatgctgatg aggaagaaaa aaaagaaagt    360

gaagatgaag agaaaaagag tgaaggtgaa gaagaaaaag cggaaggtga agaggaagaa    420

aaaaaggatg gaattgagga agaaaagaag gatgaagatg aagaagagaa gaaagatgat    480

gatgaagaaa aaaacgagga agaaggaaaa aaggatgatg aagaagaaaa cgtagacaaa    540

gaagaaaaga aagatgatac ggaagagaaa gaggataaac attcaaagga taaaagtaag    600

aaggatagta agtccgttca aaaggataaa aaggaggaga aggagaaaaa ggataaaagt    660

tcaagtggtg ataattctaa aacagataaa tcagataaat cacatagtaa tcaaaaacaa    720

gacagcaaag aaccatgtaa tggggatact gcttacaact gtcctaaact atcaggtctt    780

tgtgaatcaa aaattcaagt acaacaagac ttcatgggtg aaaaatgttg tgctacatgc    840

aaaaattcgg ttcctgtcgc gaagaaagat ataccccttat gcactgattt ggctgataat    900

tgtgatcaaa tagcatccac ctgtggggaa gaggcgtggc aaccgactat gatttctgat    960

tgtgctcaga catgcgataa gtgtgaatta cattttcaaa tgttggaaaa gaaacttgca   1020

gcagctgctg cttaaaaatt ttgaaaggaa aagaattttt atcaaaaata tatgtatcaa   1080

aaatatattt tctttgattt tcacaccctt aatactaaaa tttcaattta ttcatcagtg   1140

tttctcgtaa ttatatttta ttaatttgtt tcgagattta gtaaagatgc tttaaaccaa   1200

aaaaaaaaaa aaaaaaaaaa aaaaaaaa                                      1228
```

<210> SEQ ID NO 18
<211> LENGTH: 737
<212> TYPE: DNA
<213> ORGANISM: Meloidogyne incognita

<400> SEQUENCE: 18

```
ggaatttttc aaaaaaagta ggctggagaa taaatttatt gaaaaaccag aattcttaaa     60

gtttcaacca tttaaaaaat gtcaaacaat tttaaaactt gcccagcttt attatattta    120

ttgcttctgt tgggaaaagc aagttgcaat tattttgaat cagaattaag cttagctaat    180

gacaaaactt ctatagttcg caaatgttgt cctaaggaga agattagaca ccatcggaga    240
```

-continued

```
ccgttgcatt gctgccagga tgggttattc cgtgatgaag ttgatggtta tttattaaaa    300

gaatgtgcag atcaaggtga ttccatagtc aaaacaatta gatgtgctca acaagaaata    360

catggtgaaa atgcagtgga gatttgcaaa gcctattgct gcgaattatt cagagataat    420

aattgttcca aaatatgcct aacaaacatt accaaagtaa acatgtctat tgaaatatta    480

tttgagctgt taaaaaaatg caggaatcat gagaattatg gggaagtcca tgactgtatc    540

cattcaaaaa gaccaaaaaa catggatgcc gcagagttgg aaatttattg taaaagggct    600

attaatatgg tttaaatctg gaatttattt tttaatttat tctactcgat ctccttttat    660

ctatttaatt attaatttat ttttggcaat aaaatttaat aaaaaatgta aaaaaaaaaa    720

aaaaaaaaaa aaaaaaa                                                   737
```

<210> SEQ ID NO 19
<211> LENGTH: 656
<212> TYPE: DNA
<213> ORGANISM: Meloidogyne incognita

<400> SEQUENCE: 19

```
ggtcgtcatt cttgtaaact aaaaatcttc aaacttcaca aaaatattcc ttaaacttct     60

tcacaaaaag aattgaaaaa tgttattaaa attctttctc ccattattgc ttttggttac    120

ccttatctat ttggggtgtt ctgaggagga taaggaagac attgcaaatg gtcctcagga    180

atctgagaat caggttgatc aagaattggt tagattgaaa agagatgatg aagaagagga    240

gggagagaag gctgaagatg aagagaagcc tgaagaggag ggagaaaagg ccgaagatgc    300

tgagaatgca gaaggagatg ctgataaagg agatgctgat gaggaagaaa aaaaagaaag    360

tgaagatgaa gagaaaaaga gtgaaggtga agaagaaaaa gcggaaggtg aagaggaaga    420

aaaaaaggat ggaattgagg aagaaaagaa ggatgaagat gaagaagaga agaaaggtga    480

tgatgaagaa aaaaacgagg aagaaggaaa aaaggatgat gaagaagaaa acgtagacaa    540

agaagaaaag aaagatgata cggaagagaa agaggaataa acattcaaag gataaaagta    600

agaaggatag taagtccgtt caaaaggaca aaaaaaaaaa aaaaaaaaaa aaaaaa        656
```

<210> SEQ ID NO 20
<211> LENGTH: 1499
<212> TYPE: DNA
<213> ORGANISM: Meloidogyne incognita

<400> SEQUENCE: 20

```
atatttattt tttaatttaa caaaaatatt tttaattaaa attatttatt taatgtttaa     60

attgttgttt ttcattttgt ttgccttatt aaattctgtt gattgtcttt taaaattacg    120

aacactggat aaagaacatc ttctggttga ggagagatat gccaaggaag atacgcttta    180

tctttttgtt tttcctagaa catcaaatgc cccatatttt ggagcaatgt gtctttatgt    240

tgaagctgtt ttaacttgga aaggaattcc ttttcataga ataagtaacc aattctttct    300

tggttcaaaa actgatggag caattccttt tgctatttat aacgggaaat atttggatgg    360

agcagaaaaa ataattgaag aagttagaaa aaagggaaat aaaaaattga gtgatgaaca    420

tgatgataat attagaaaat ttgcaactag aaccttgcta aagactctaa ttgctgatag    480

aacatttcgg agagatcttc cccatgcaac aattccaaaa aataattccg aaacacaaat    540

agcctcttct tcattatcaa atagtgcacc agcaactccc aagggtggaa tccctacaag    600

aaagagattt agtccaattg atattaaaat ccctcatact aaaaatgaag aaataataat    660

ggcaaaatct gaggggcatt ctcctggaag ttctttcttt tctagaacta ttgctcattt    720
```

-continued

```
aaaattacat aataataatt ctccaaagaa aggtccgggt ggtcttgatt ggatgttaaa    780

agatgaagga gttcgtgaac aattaattcc agttattcca gaggcttttt tagaagaaag    840

tatgagtgat gaatattttg attccccggt aaaagataaa aatgaaaaga aatcaaaaag    900

agaggaggaa gatgaaagtg atgaaacaaa aatatctaaa attaaatatt ccattaaatt    960

gacgttaagt ccagaattgt ggaaagatta ttttaatatt ttaaataaaa taaaaataaa   1020

tggaagggaa aatagagaag aaattaattt attgaaaata aattttcttc aagaatattt   1080

cggattctta gcaagaattg atgatgattg ggaacgtgta aattctattc tgaaaaatac   1140

aattaacgat attttaaaga aattaattgt tgatagccaa atacctttt gttgggaaaa    1200

aaggttgaga gagattaatg ggaaaaatat taatgaagtt gaagtattta atgaatttaa   1260

agataaaata aaatcgttgg gtataataaa aagttgactg aggcagagac taaaaataat   1320

tttttgcatg gaaataatcc aactttggct gattttgccc tttttgcttt tctcaatcaa   1380

ttttttgaat ttcctttaaa tattccagaa tttaaagaat tatttacccc agaaaagctc   1440

agtaatgagg aaaaagaatt aattgcgaaa aaaaaaaaaa aaaaaaaaaa aaaaaaaaa    1499


<210> SEQ ID NO 21
<211> LENGTH: 1266
<212> TYPE: DNA
<213> ORGANISM: Meloidogyne incognita

<400> SEQUENCE: 21

ggcatcaaac aatctcctca acaactaata aactcaaaaa acaccccaaa acaaccctaa     60

aaacaaccca aaaatgtcca tcttccctac ttctgctctt ctagtcattt caataatcgc    120

tatgaccgag ggtgcaggcg atcgaagcgc ttcaacctct actggttgta caacctattt    180

tggcatgctt gatcatgcgg ataccaagga aaataacaaa agaaaaactt tcaaacccaa    240

cgataaaacc aaatccaaca ccttgcaagt gactggtggg gcaatgttca gcaatacctc    300

ggtggcgttg gttgtcggtg ataaggcgtt atgtatggct aagacaggaa gttcagacga    360

ttgcggaatg cgctacgatg ctttgactgg aacaatgaaa tttatcattt ctgataatat    420

tactgttgaa gtgggtgtgg gtttatataa ttggtgccag acaaatggaa aggcccctgt    480

cactaacata ccatccggag cgttcatgtt gccccggaag taactggtgg cccacaaaag    540

ggcaatcact attgattaca acccaaatat ctataggatt ttgacatttt ctggcataat    600

ttaggtattt tctgacattt ttctgacatt tttaactaga attaattcaa ttgaaaacaa    660

aataatagga ttgacctaaa tgagcgtttc ttggatatcc ttttaacagg agcagtctct    720

aattttgtaa gagctcctaa tgtttaccct cctccatctc cctccccctc tatgctccta    780

ccaatgactg attaagttaa aaatcgtaca taaaatggag agtgtataaa tctgggtgta    840

tatacaatca ggattcgact ttataacatt tgaaggttcc atttgaagac gttttttct     900

tcaccgacaa caagtgtgtc atccagcttg taagctacga taataaaact aataaaactc    960

ttctcaaaat taatgatgtc gacttcaaaa ttatccctac tgataagaaa atttccccga   1020

aggcttgtac tatgaaaatg tgagcttgta ctatgaaaat gtgagggaaa aaagtaaaga   1080

aaagaataac aaaaagtgta aatatggaag gataaaaacg aaacaaaaat gaatgtgaag   1140

taaaaaataa aaagaaattc aagtagattt aaaaaaaatg ttaagcttca caatatctgt   1200

ctccttttgt ttatgttttt cgaataaatc gcattaccaa aaaaaaaaaa aaaaaaaaaa   1260

aaaaaa                                                              1266


<210> SEQ ID NO 22
```

-continued

<211> LENGTH: 723
<212> TYPE: DNA
<213> ORGANISM: Meloidogyne incognita

<400> SEQUENCE: 22
gaatcacaaa aatggccacc tttttcactt ttacccttct aatcatttca attattgcca 60
caactgaggg aatgaatact aatcgaagtg cttcaacctc cgattctctc aaagaccaaa 120
aggattgtaa agtgatatat ggcatgtttg tgcctgtagc agggtcaaaa atgcatggag 180
acgccaaaag cgcaatgaag ccaaacaatc caagtctccc caataaatta attgtatcag 240
gtggcaactc aaaatattca gtgactttac aggttgaaaa ccagccgaag tgtgttgccc 300
aaaatgacgg aaaccctgta gaatgccaaa ttcaaggaga caaactttca ggaaaattga 360
tttatgatat tgaaaacggc ccttctgtca acgttccctt caaagacacc ccaatctttg 420
ttggaaataa atgcgaaatt gtttttgtag cctacgataa ggaccacaaa ttaactcttc 480
ttatgaataa agtaaagctg atgattgagc cgacaaataa gcaaattgta aaggcttgtg 540
gagcgaaaaa ttatatggaa aaatgatgaa tgaatgaatg tgggagggaa ggaaatgaaa 600
aatattttta aaattgaaga aagcattcaa aatttaaaaa aaaaacaatt cttcaaataa 660
tatataactt taatattttt gataaatttt atttcataaa aaaaaaaaaa aaaaaaaaaa 720
aaa 723

<210> SEQ ID NO 23
<211> LENGTH: 824
<212> TYPE: DNA
<213> ORGANISM: Meloidogyne incognita

<400> SEQUENCE: 23
ggcatcaaac aatctcctca acaactaata aactcaaaaa acaccccaaa acaaccctaa 60
aaacaaccca aaaatgtcca tcttccttac ttctgctctt ctaatcattt caataatcgc 120
tatgaccgag ggtgcaggcg atcgaagcgc ttcaacctct actggttgta caacctattt 180
tggcatgctt gatcatgcgg ataccaagga aaataacaaa agaaaaactt tcaaacccaa 240
cgataaaacc aaatccaaca ccttgcaagt gactggtggg gcaatgttca gcaatacctc 300
ggtggcgttg gttgtcggtg ataaggcgtt atgtatggct aagacaggaa gtccagacga 360
ttgcggaatg cgctacgatg ctttgactgg aacaatgaaa tttatcattt ctgataatat 420
tactgttgaa gttccatttg aagacgtttt tttcttcacc gacaacaagt gtgtcatcca 480
gcttgtaagc tacgataata aaactaataa aactcttctc aaaattaatg atgtcgactt 540
caaaattatc cctactgata agaaaatttc cccgaaggct tgtactatga aaatgtgagc 600
ttgtactatg aaaatgtgag ggaaaaaagt aaagaaaaga ataacaaaaa gtgtaaatat 660
ggaaggataa aaacgaaaca aaaatgaatg tgaagtaaaa aataaaaaga aattcaagta 720
gatttaaaaa aaatgttaag cttcacaata tctgtctcct tttgtttatg tttttcgaat 780
aaatcgcatt agcagcaaaa aaaaaaaaaa aaaaaaaaaa aaaa 824

<210> SEQ ID NO 24
<211> LENGTH: 696
<212> TYPE: DNA
<213> ORGANISM: Meloidogyne incognita

<400> SEQUENCE: 24
gaaataatct cctcaacaac taaaaaaact caaaaaaaca ctccaaaaca actctaaatg 60
gctttcctct tcacttctac ccttctaatc atttcattgg cttttattgc catagctgag 120

-continued

```
ggagcaggcg atcgaaatgc atcagcttca agccctggtt gtatgcaggt tgcaaccctt    180

attcatatag gggaaattcg cccagcaaaa gcaaacaaac caggtgtaca aaatactcta    240

aaaatgtctg gaaatgttca aacattcaaa actactcaag tgacattaca agtagctggg    300

caagagcctt gtaccgttaa aattaataat ggcgaaacca aatgtaaaat aaccggagat    360

gaattaaatg gaaaattaat tttcaaaact gaaaaaggaa ctgaaatttc tgcttatttc    420

gaactggttc cattattttc tgaaaataag tgtgttattg aacttgacac ttataacaag    480

gaaacccatg aaactaaact tataattaat ggaaataatt ttatgattaa aaagaaggaa    540

ggtagtgttt caactaagtg tggtggaaga gctaatactg tttaaatttt aaaagtgtga    600

attgaaagag gaagagaata taaacaaatg tgaggatgag aaaaaaatat ttttgaagaa    660

agcattacaa aaaaaaaaaa aaaaaaaaaa aaaaaa                              696
```

<210> SEQ ID NO 25
<211> LENGTH: 1687
<212> TYPE: DNA
<213> ORGANISM: Meloidogyne incognita

<400> SEQUENCE: 25

```
gattcaaaaa atattattta aaaattcttt accatttaat taacaaattg taataaaaga     60

aagacaatta aaaaatgagt ccttcctcat tcaccttaac ggcagtactt cttgaggcga    120

ttgtttttct ttacaaccgt caagtagcgg caatgctttc catgcatccg agctgttctg    180

gccgttcatc aaccattgag aataaattga aaatgagcgg gggtggtaac ggcatcaata    240

aatttacacc gggaaatgtt tcattcccgg tagcatgcca ataccattca aagaatctca    300

aagcaacaaa taaaaaggaa tataaaatct cagaagattt gcctatgaat caagaaaagc    360

ttacaaacag taaggaagat gatctcattc ataaggtaaa aaagatagat aagggcaatg    420

gagctgctgt tccttataaa acaaacaaga acaatgaaat tggagatgga gccgagaatg    480

gaaaagctgt caaaattaga gaaattattt ttactgaaga gcaaaagaaa atgactagcg    540

aagaatttga gcattatttg tatagtgttc catatgacaa aaacaagaaa aacaaaattg    600

gaaaaaacga aaatggtgaa aaagttgata aaccaagcaa agaaggagga gatacaatgt    660

tttattcaaa agctgggata attgctaaaa agataaaaga atatgtcccc actaatggcg    720

aattcaagat ccagactgga cttgtatatc gtaacaatag ttttaatgct tcccaagatg    780

atagtaaaaa tttactaaat atttcgcata ttttaatggc tttaaatgaa aatgagaggg    840

attctcaaga aaatttgaga aatgctgctg atttgtttgt ggcacttcat gagtgttacc    900

aactcttttc ggcaattcct ctagtttttg aagtagaaat ggttttgaaa aaacttgagg    960

aagagggaaa caaagacgat ccaataaaat tactcgaata tttccgtttg ccaacaatta   1020

aatatccatt attggatttg attaaaattg agaactcaac tgtgtctcca gatgagttga   1080

ttgaaaacgt cactaaaact attcacaaag cagacaattt tattgctaaa aacatccatg   1140

cattcttcat aaatgacaac gaaacatttt ttaatgaaat aatttctcgt cttgaaacag   1200

ctgatatggt tttggccagt atcaaaaaaa ttcttaaaat gttcaataac tttaatgaga   1260

aaattcccga aaacttttcg atgctaaaac gtttaaaacc aattgaaatg cacgatttat   1320

tcgaaaattc taaactgctt caaaagcttc atgcagcaat tttgcctgga gatgaaatga   1380

aattttgaaa tgagagttaa atatttttaa aaaaatttttg cgaacacaaa aacaacaaca   1440

aattagaaga atattaaaat tattaatgaa acaagagttg ccgcggctga tcggaaatat   1500

taattaaatc caatttagct gacgttgcct gctcaatcac caaataaatc aatttatgat   1560
```

```
tttgcccatt ctctatcatt accttatttc ctatttgtac attttttttt ctttttttaaa   1620

aattattttt agttttgttc ttgaatgttc gcttaaataa attctaaaaa aaaaaaaaaa   1680

aaaaaaa                                                              1687


<210> SEQ ID NO 26
<211> LENGTH: 783
<212> TYPE: DNA
<213> ORGANISM: Meloidogyne incognita

<400> SEQUENCE: 26

gatcaaacaa tctccttaac cactaaaaaa ctcaaaaaac cccctaaaag cagcccaaaa     60

aatacccaaa aatggccatc ctctttactt ctacccttct aatcatttcc cttttgggaa    120

ttaccgaggg agtgaataca ggcattccga gcggatcttc tccaccctct tctgcttgtg    180

agacttacaa gggcaaaatt gagcacatgc cagaaaccgc cagaaaaatt gaatggaagg    240

aaaatactcc cggaggaaag catttaatcc ttaaaaagtc tattcaaggt ctagacaaag    300

taaccctcaa aattgaaggc aaagaatgta gtgcttccct caacaaccct ggaacatgtc    360

aagtcgatgg acagtcccat gccggtcaat tagtctttgt aacttcaaag gctaaaattg    420

aggttgactt tggggaagct caaatcttct ctgggaacaa gtgcgagatt gaaattgaga    480

agtatgaccg tgctacctac gtaactctaa tcaaaattaa tgggggtgac ttcaaaatta    540

cgcctgattc gccacctatg ccgatgccat gcaaaaatat gatgaactaa aaagtgagga    600

ggagggaagg aaaagtgaag gaagagacca tgtaaaattg aaatattgaa gaaagcattc    660

aaaaatttaa tttttaaaaa atctgtttgt ttagtaacta aatatagctt tctattgttc    720

ttatattttg tttatcttta tcaaattaaa atgaaaaact caaaaaaaaa aaaaaaaaaa    780

aaa                                                                  783


<210> SEQ ID NO 27
<211> LENGTH: 798
<212> TYPE: DNA
<213> ORGANISM: Meloidogyne incognita

<400> SEQUENCE: 27

gacattcatt taaacattca ttaattacct aaaattgttt ttcaaattgt ttgcctctga     60

gttttgctca actgagaaga aaaatgcttc cttactcaat tctatttcaa ttgggaatag    120

tttcgttgct tctacctcat gcaaatggaa tgcagtctgg cagtagcaaa attatgaaca    180

aagcatctga aaagaaatat gctttggttg ttgctccaaa ctttcttaaa gttcatttta    240

aaatgaacag tgtctttgcc aatgcgttga ccaaaaagtt ttttgtgcac tttctaattc    300

tgaacaccaa aaatgaagaa attggagata atttcgacta tggaattgat ctcgaaaaat    360

ttgaagaagg aacgggaaat acatatcaag ttgtaaattt tccagatgat tatcccgaaa    420

aattgaacga aggcgtgaag aatttagaga acaaattcat taagagaggt tacgaacaga    480

gtagtcaaat tctgaaaaat gaagctttca ccgtttataa agatttattt gaaaacaatg    540

gagctattgt tcattacttg aaggaggcaa agtttgattt aggggttttt gacacttggg    600

acactggagc tctcttcatt ctccatgcag caggaattaa aaatgttttt ggcattaaca    660

acattcaact taatgcttat caatttaaat atgctgggaa agaatttcca aaaaatattc    720

cagaaattta attcggcaca aacaggcgat aatgaattat caccaacaaa ggaaaaaaaa    780

aaaaaaaaaa aaaaaaaa                                                  798


<210> SEQ ID NO 28
```

-continued

<211> LENGTH: 704
<212> TYPE: DNA
<213> ORGANISM: Meloidogyne incognita

<400> SEQUENCE: 28
ggcatcaaac aatctcctct cctcaacaac taaaaaactc aaaaaacacc ccaaaacaac 60
tctaaaatgt cggctctcct cttcacttct acccttctaa tcatatcatt ggcttttatt 120
gccatagctg agggaacagg cgatcgaaat gcatcagctt caagccctgg ttgtatgcag 180
gttgcaaccc ttattcatat aggggaaatt cgcccagcaa aagcaaacaa accaggtgta 240
caaaatactc ttaaaatgtc tggaaatgct caaatattca aaactactca agtgacatta 300
caagtagctg ggcaagagcc ttgtaccgtt aaaattaata atggtgaaac caaatgtaaa 360
ataaccggag atgaattaaa tggaaaatta attttcaaaa ctgaaaaagg aactgaaatt 420
tctgcttctt tcgaacaggc taaattgttt tctgaaaata agtgtgttat tgaacttgac 480
acttataaca aggaaaccca tgaaactaaa cttaaaatta atggaaataa ttttatgatt 540
aaaaagaagg aaggtagtgt gtcaataaag tgtggtggaa gagctaatac tgtttaaatt 600
ttaaaaatgt gaattgaaag aggaagagaa tataaacaaa tgtgaagatg tgaaaaaata 660
ttttgaagaa agcattccaa aaaaaaaaaa aaaaaaaaaa aaaa 704

<210> SEQ ID NO 29
<211> LENGTH: 414
<212> TYPE: DNA
<213> ORGANISM: Meloidogyne incognita

<400> SEQUENCE: 29
gacattcatt taaacattca ttaattacct aaaattgttt ttcaaattgt gattttattt 60
atttctattt aatatcttta aatgcggagt gctttaaaaa ctttaattgt tttgtggcct 120
cctttgcttg gacattttat tttgttaatt cctagtggag tagcttttgt agttaaagag 180
aatgttcaag aagtatcgcc tgttattcct gataaacccg gagtaattgg aggtgatgtt 240
attgataaaa gcgcaaaaac tagtcaacta aaaaagggaa gtgaaagtct gatttctgga 300
attgaacgta gccatgttga ggaattaaag gaggaaatta aaggagaagg taagaaagta 360
cccaaaatga atggacagga taatgaaagc cttgaaacta aaattgttga aaag 414

<210> SEQ ID NO 30
<211> LENGTH: 748
<212> TYPE: DNA
<213> ORGANISM: Meloidogyne incognita

<400> SEQUENCE: 30
gatcaaccaa tcccctcaac aactaaaaga ctcaaaaaca ccccaaaaca actctaatat 60
ggctctcctc ttcagttcta cccttctaat catttcattt attgccatag ctgagggagc 120
aggcgatcga aatgcatcag cttcaagccc tggttgtatg caggttgcaa cccttattca 180
tataggggaa attcgcccag caaaagcaaa caaaccaggt gtacaaaata ctctaaaaat 240
gtctggaaat gctcaaatat tcaaaactac tcaagtgaca ttacaagtag ctgggcaaga 300
gccttgtacc gttaaaatta ataatggcga aaccaaatgt aaaataaccg gagatgaatt 360
aaatggaaaa ttaattttca aaactgaaaa gggaactgaa atttctgctt ctttcgaaca 420
ggctaaattg ttttctgaaa ataagtgtgt tattgaactt gacacttata acaaggaaac 480
ccatgaaact aaacttaaaa ttaatggaaa taattttatg attaaaaaga aggaaggtaa 540
tgtgtcaatt aagtgtggtg gaagagctaa tactgtttaa attttaaaag agtgaattga 600

-continued

```
aagaggaaga aaatataaac aaatgtgaag atgagaaaaa aatattttga agaaagcatt    660

ccaaaaaata aaaaaaaatt aattcttcaa atccatttat tttttgaata aaacatttta    720

ctaaaaaaaa aaaaaaaaaa aaaaaaaa                                       748
```

<210> SEQ ID NO 31
<211> LENGTH: 1511
<212> TYPE: DNA
<213> ORGANISM: Meloidogyne incognita

<400> SEQUENCE: 31

```
gatttttatt aattttaaaa attattaact ctccaaaatg aagtgtttgc tccccttctt     60

ttggatttta ttaacaattt ttgtttcttg cactaatggc acttcaaatg agtatagtga    120

acttgttttg gttcaagctt tgtggagaca cggtgatcgt tcacccacaa aaaccttcaa    180

aacggataaa tatcaagaaa aggattggcc tcaaggatgg gggcaattaa cacctacagg    240

aatggctcaa catgtagagt tgggaagacg actaagacag cgatatatag aggaattgaa    300

atttgttggt cctcggtata atagccatga aatttatgtt agaagtactg actggaatag    360

aacattaact agtgctatat cgaattttat tggcttctac ggccccggaa atgatgatga    420

atacccaaag gatttgggcg caaacaaatg gccaggatgg tttttcccaa tagcgataca    480

ttcactccct ggaaacgaag attttatggc tcctggagaa tcggaatgta aacgatttga    540

acaaataaaa gaacggataa ctttaacaga agaatacaac tcgactttga ttaaatacaa    600

atggctactc gatttttga gtgaaaagac gggacagaat gtcgacccttt tcgatatgtg    660

gatgattaac gatgcttttt atattgagaa attaaaaggc aaaaaattgg tagactgggc    720

agaggggaac caaacacttt tggatacgat tgctgaactt gacaatttac aagaaagatg    780

gatggttggg ttagatttaa aacctctggg tgatgccaac tttcgcgaag aacttccaaa    840

aattttgggc gggccaatct tatggaaatt tataacaaat atgcaggaga agttggcttg    900

ttcaaagcga atgaattctg taaaagaaat tgacagggaa atagagggaa gaaaatcgcc    960

aatggggacg cccttgtgta aatggatgaa caaaatgcgc tattttgcgt actctgcgca   1020

cgacagcaca attattgcaa tttttgcagc tttgggttta aacaaaacga attatgacga   1080

ggatggttac ccgaagtatt ctacttgtgt aacttttgaa ttgtggaggg agaagaatac   1140

tggtcaattt gatgttaagg tatttttatg gagacctaac accaacgaga cttcccctaa   1200

agaaataacg acagatattg aaggctgtca aagcaattca actctagaac aatttgttga   1260

aagatcaaaa aattatcaaa tgctgccttc acccaaagac tattgttcac aacttctaca   1320

acccctaaat aatgctgcac gtatgttaat tcagtggaaa ttggaaatgc ttattctaat   1380

gggaattcct tcaattgttg ctaatgttgt atagagaatt tttttgtttt tggaaattat   1440

ttagttgcac ctattcatca aaagaagggc aaaataaatt tttatcccct aaaaaaaaaa   1500

aaaaaaaaaa a                                                        1511
```

<210> SEQ ID NO 32
<211> LENGTH: 994
<212> TYPE: DNA
<213> ORGANISM: Meloidogyne incognita

<400> SEQUENCE: 32

```
gatgcttcaa ttgacattta aaattaaaaa gacccaggtt tcttaattaa agaatgtttt     60

taaaaatttt aactttcctt ttaattataa acaaaattat tgcggatgat tctaatagcg    120

gagatagtgg caatgaaaat tctaatagta agcccagtga tgagcttgcc gactctgttg    180
```

atgttcgaga gcatgataat gagcaacatc catccaattc gatcgacaag caaaatcttc 240
aagacccaca atttattaaa gaagatgtta caaatgtatt gccactatta aataacgatg 300
agaataatct cattgatgaa tacacaacag aaaaaattaa agaagatgag gaagaccaac 360
taaataatga aggatctggt atagacaatg aatttcctga ggaagataat gatgtaaatg 420
gattggatat taatacaact gcaaaatatg ctaatgatgt agatgataat aataacaatg 480
aaggtgatgg tcaatcatgc gtttatgagg atggtgtaat taacgataat ggtgacgaac 540
gcacacctac atatgaagaa caacaacaaa ttgaagaata tcttcaagaa atgcgtgaat 600
ttgaagagca aatggtcaaa gacagcgcta attttatgag aaatttggca caatttgtga 660
tgagtcaatt cgaaaacatt tttggttctt ctacctcgtc tctatcaggt aacaataata 720
atttgttgga gaaaaaacct ttagaagcac caacacctcc ttgtttatgc aaaaaatgtg 780
acagtatgac atttatacaa aataagcaaa ccaaatatct taaaaatttt gctaattaat 840
taacaaaaat ttgaagaata atttaaataa tgtttatctc tttcttgaga ttttcaaatt 900
atttaatcca tttatatata aatttaaatt cattttcttt tacaaaaagc tgaagagatt 960
aaattttaat gtttgaaaaa aaaaaaaaaa aaaa 994

<210> SEQ ID NO 33
<211> LENGTH: 362
<212> TYPE: DNA
<213> ORGANISM: Meloidogyne incognita

<400> SEQUENCE: 33
ggaataaaaa gcggcgaaat tttactttat tcatcaaagt actttaaaat attctataat 60
ctaaaatgaa attcagccaa ttatttgttc tcttaataat tgctttacaa tttgtggttg 120
ctcaagggtt gatttacgat gcgaaagcaa tagccaaagg aaaaggaaaa ccgttcaggg 180
cgctgaatat ttggtatttg tcttgggcaa ctatgtaatg aagaaacgat atctttatgt 240
aattgataaa taaaaataac ctaagtatca aaaaatgttt atgggaaata aaagatttat 300
cttcatttaa aatctaataa atttgtcaat cccaaaaaaa aaaaaaaaaa aaaaaaaaaa 360
aa 362

<210> SEQ ID NO 34
<211> LENGTH: 1124
<212> TYPE: DNA
<213> ORGANISM: Meloidogyne incognita

<400> SEQUENCE: 34
ggtttaatta cccaagttta aggggtaaaa aatgttttca agcaaaacta gcttcaattt 60
ccttcttcta atttcttcat ttgctttatg taaggccgac ttttggccta aagcaagaaa 120
taatattacg gtatccgaaa caatacaaat tactaaccgt gactgtaatt ttgatcgtta 180
tattcccgat ccgagtaaac ttggaaacgg aggtcagaac gagcatcaag gctacgtttt 240
tgaaataaaa aatggtggtt ctttatctaa ttgtataatt ggtgctaggc ctgggactaa 300
aggctctgct catggagttc tttgtgatgg agattgcgat ataaacaatg tttggtttga 360
ggatgttggg gaagatgcta ttaattttaa tggagattct gatggttgtg tttataatgt 420
taatggtggt ggtgctaaga atggagaaga caaagttatg caatttgacg gaaaggggac 480
actgaatgtt aacaactatt atgtagacaa ttatgtccgt ttttgtcgct cctgtggcga 540
ctgcggtgac caacatcaac gccatatcgt gattactaat ctgacagcgg ttcatggcca 600
agctggtcaa ttcgtttgtg gagtaaatag caattatcag gatacgtgta ccttgcatga 660

-continued tataaaaatg gagaagggta ttcacccctg caaggttttt gatggcaatt ctgatggatc 720
tgagccaact tcgaataacg acgaagagga ccacggagac gggaaatttt gtatttataa 780
gaagggcgat attaaatata ttggatccaa accaaagccg aaaagcaaaa agagcgcaaa 840
gaattaagtg ccggaagtta aaaagccttg aagttaaaaa cgtttaaagg gataaattgt 900
agggttgtcg gttctgaacc gaaccgagcc gaagaaccga tgatttttcg gttcggttcc 960
ggatatccaa agattttcca agagccgaca accctagtag tatgagtaga atctattatt 1020
atttggaata ctaatttaat tttgtgaaat ttctttttac tatattaatc ctgtccaata 1080
aaattatgaa atcgaaaaaa aaaaaaaaaa aaaaaaaaaa aaaa 1124

<210> SEQ ID NO 35
<211> LENGTH: 782
<212> TYPE: DNA
<213> ORGANISM: Meloidogyne incognita

<400> SEQUENCE: 35
ggcatcaaac aatctactca acaaataaaa atccctaaaa acaccccaaa acaaccctaa 60
aagcatacca aaaatggcca cctttttcac atttaccctt ctaatcattt caattattgc 120
cacaactgag ggaatgcata ctaatcgaag tgcttcaacc tccgattctc tcaaagccca 180
aaaggattgt aaagtgatat atggaatgtt tgtgcctgta gcagggtcag aaatgcatgg 240
agacgccaaa agcgcaatga agccaaacaa tccaagtgtc cccaataaat taactgtatc 300
aggtggcaac tcaaaatatt cagtgacttt acaggttgaa aaccagccga agtgtgttgc 360
ccaaaatgac ggaaaccctg tagaatgcca aattcaagga gacaaacttt caggaaaatt 420
gatttatgat attgaaaacg gcccttctgt caacgttccc ttcaaagaca ctccaatctt 480
tgttggaaat aaatgcgaaa ttgtttttgt agactacgat aaggaccaca aattaactct 540
tttcatgaat aaagtaaagc ttatgatttc cccgactgat aagcaaattg taaaggcttg 600
tggggtgaaa aattagaaag aaaaatgatg aatgaatgaa ggtgagaggg aaggaaagaa 660
aaaatatttt taaaattgaa gaaagcattc aaaaattaaa aaaaacaatt cttcaagata 720
atatataacg tttaactctt tttgataaat tttatttcaa aaaaaaaaaa aaaaaaaaaa 780
aa 782

<210> SEQ ID NO 36
<211> LENGTH: 801
<212> TYPE: DNA
<213> ORGANISM: Meloidogyne incognita

<400> SEQUENCE: 36
attgaagaag atgatacatt caatgttcct gtcatgggag aagaaaatca tagagatatt 60
cctgtcgaag aagctaatta tcaagttcct ccttctgctg atttcacttt tacaagctct 120
gagcatggaa gacgtacatc atttacagtt ggaacaccgc atcatcgata catgcaacca 180
ggcactcgag aagcatattt attgccccat ccaggagggg aaggtgcaac gcttatacgc 240
aatgaagttc gtcgagatgg aacgcaaatt tcccaacaag acacacttca aaacattgaa 300
ggagggagag gttatgttta ttcttcatcg tcccacactc aaaacgaatc aagtagtagt 360
tcaagaataa cttcgagaat tcgttttggg aataatgaaa gacatgggaa aaaatgagga 420
ataaagggaa gatttaggaa gacatggaaa aaagtgagga atggaggaag agatttatac 480
taattataaa atgatagaaa aattgaagag atattctctt attctttcct atatctttac 540
tttcacatac aaaattctat aatggcaatt tatgatttaa cattaaaatt gaatttagaa 600

```
atatttttta aaattatttt agttttcatt tttatcaatt ttttgatatt taaatacgtc    660

ttgtatttat cttcatataa ttgttgatta aacttttctt tatcattctt ttgtaggtat    720

tctaaaatta aataattata tgtaatattt tttaattttc aatttgaata aaattttctg    780

caaaaaaaaa aaaaaaaaaa a                                              801
```

<210> SEQ ID NO 37
<211> LENGTH: 2210
<212> TYPE: DNA
<213> ORGANISM: Meloidogyne incognita

<400> SEQUENCE: 37

```
gacattcctc agcttcatta cccatccatt tttcatagac aacatccccc ttgccaaaca     60

ttaaaaattg agtaacgctg aatgaagctt tttgtcctgt taattggagt tttagccttc    120

acggttctaa atgtccatgg aggagtcagc cattcgacat tgactcacag aaacccgcga    180

agcaacgaaa tcgaacaatt aactgatgtg tcgttggacg ataccccatc ctcgcctcct    240

caagctgtgt tggacattgg aatgtcagga cagcgaaatt tgcaacgtcg agaagctcca    300

atgtcgattg ggaaaaaagt ggtggctgta atttttttat ttcttctgtc ttttacatcg    360

ttatatctat tggccgtgcc aaaacaacaa attcaacaag ttgaatacaa acaatttcca    420

caaccctata aatttgttcc gattagtaac attgtcaagt gcgacagaaa aacacggcaa    480

tgttcaataa agttagagaa tttggatccg acaaacaact atagcctcta tactgcaaag    540

aatgacaagg ggagaggaga taaagtaaag ttaactaaag ttgcagatat agatttggac    600

aaatgtcaac tcgacaagaa tgtaaaacca gaagtaaatg ggaagaaat ttgtaatcag     660

attgtcaaag gaattgatga taacgcaaaa gccgaaacta ttgaggttaa cagtggagaa    720

atagaatttg gttcggaatt agaaggaacg gaggattatg cgatagttga aaaagcaatg    780

aatgagaaga atgaacataa aaatcaacaa gcggttgagc atgttcatat ccctgggcca    840

ggggaacaac cagttgaaca caatcagccg acaatagaat atccaacaaa ttccaaacaa    900

gttcatccag ctgacaaata tcaacataaa ctagaagagc gcgccaaaaa atttgggctt    960

agcgacttca aacatggaga tttatatgag gattatcgcc aacaaaaaac ggtccaagaa   1020

gatgaaaagg ataaacgata tcaaaaggtt ctaggaacac taggagacca taaacatcca   1080

tcgctagttg atcaatataa cgaagataaa ggaaaattca atcaacgtgt taaaagtgac   1140

cccacaggca ataaagttga aaaggcaaaa aattctgatt ctaatggact tgaacaaaaa   1200

ttagaaaaac tggcactgag tgacttcaaa catggagatt tatataaaga ttatcagcaa   1260

caaatcacgg tcagagatga tgaaaaggat aaacgatatc aaaaggttct aggaacacta   1320

ggagaccata aacatccatc gctagttgaa caatataaca gagataaagg aaaattcaat   1380

caacgcgtta aaagtgaccc cactagcaat tggcatgaag atttattcgg aaaggattac   1440

cgacgtgcta tgagcgattt cgatcattta aaggctaaac aacgtgaaaa gatccttgga   1500

acactagaag atcataagca tccatcgcta attgatcaat ataacaaagg aagcttaaat   1560

caacgcgcta aaagtgaccc cacaggcaat aatattggaa aggcaaaaaa ttctaatttt   1620

aatgggtctg aacaaaaatt agaaaaactg gcactgagtg acttcaaaca tggagattta   1680

ttaggtcgaa aaggaggaat taaacaacgc actataaatg ttctcgctgg caaaaaaata   1740

gaacatgaaa aaggaagtga ttttaatgca aacgttgaag aaatgatagg ggcagaaaac   1800

ggcaaggcta atcaagtgaa tcccaaatta actggacgca aactagctga atttaatcat   1860

attccagctg ttgacagaat tcttggtttt aaacgtggag gtcatgcgct agaggagcct   1920
```

-continued cataaaaatt gagatatttt gcctgaagag ttggattgaa cgatgtatat aagatttttt 1980
aaccatgtaa atatttttaa aaaagatttt attagagcca ggaaattacg atactgaatc 2040
ccgaaaaata tcgtaatggc tcttaatttt ttatttttta acttttccat tgcaaagatt 2100
tttttaaaat ttttcccgat tgtctggtaa acttgtgatg agataaactg attttgattg 2160
ataataatcg tccattttcc aaaaaaaaaa aaaaaaaaaa aaaaaaaaaa 2210

<210> SEQ ID NO 38
<211> LENGTH: 836
<212> TYPE: DNA
<213> ORGANISM: Meloidogyne incognita

<400> SEQUENCE: 38
tacctaaaat tgtttttaaa ttgtttgcct ctgagttttg ctcaactgag aagaaaaatg 60
cttccttact caattctatt tcaattggga atagtttcgt tgcttctacc tcatgcaaat 120
ggaatgcagt ctggcagtag caaaattatg aacaaagcat ctgaaaagaa atatgctttg 180
gttgttgctc caaactttct taaagttcat tttaaaatga acagtgtctt tgccaatgcg 240
ttgaccaaaa agttttttgt gcactttcta attctgaaca ccaaaaatga agaaattgga 300
gataatttcg actatggaat tgatctcgaa aaatttgaag aaggaacggg aaatacatat 360
caagttgtaa attttccaga tgattatccc gaaaaattga acgaaggcgt gaagaattta 420
gagaacaaat tcattaagag aggttacgaa cagagtagtc aaattctgaa aaatgaagct 480
ttcaccgttt ataaaggtta aaatccaaaa tattttgcct tctaaaattg ttatttgatt 540
aataatatat aaaatattta agatttattt gaaaacaatg gagctattgt tcattacttg 600
aaggaggcaa agtttgattt aggggttttt gacacttggg acactggagc tctcttcatt 660
ctccatgcag caggaattaa aaatgttttt ggcattaaca acattcaact taatgcttat 720
caatttaaat atgctgggaa agaatttcca aaaaatattc cagaaattta ttcggcacaa 780
acaggcgata atgaattatc accaccaagg gaaaaaaaaa aaaaaaaaaa aaaaaa 836

<210> SEQ ID NO 39
<211> LENGTH: 398
<212> TYPE: DNA
<213> ORGANISM: Meloidogyne incognita

<400> SEQUENCE: 39
gacatttaat tttttaaatt tcttaacatt aaataaattc aaaaagaaaa ttgagaaaaa 60
aaatctttta atttaaaaaa aaagaaaaaa gaaaaatgta tccttggaca atttttcttt 120
tattaattat tttgttggct atggccattg aaataattgg aggaaaaggt cgaaagttaa 180
ggaagagaga caaagaggaa aaaggtcatg cctcaatttt ctgttgggca ttcatctagg 240
gaaggtttcg aggaaaagct tgatgaaatg gttgaatcaa cttcaaatat gttaataaat 300
cttggtaaaa aagtaaagaa aggagggaag aaagttgtaa aaggagttgt agaaactgcg 360
cagctgatca aaaaaaaaaa aaaaaaaaaa aaaaaaaa 398

<210> SEQ ID NO 40
<211> LENGTH: 860
<212> TYPE: DNA
<213> ORGANISM: Meloidogyne incognita

<400> SEQUENCE: 40
caagtttgag cgtcagcaat tttaaattaa aaaaagacaa actataaaat ctctcttatt 60
taaaataagc agtataccct tcaatctatc cacaatccaa taaaactttc taataaaaat 120
cctccactaa aatggcatcc ttttttttatt tcttatttat ttctgttagt cttttgattc 180
tagctaatgc tgatgatgct ggtagatatc cttcaggaga tgatttagtt gaaggtacta 240
ctgctgctcg gcttcattcg tcttctgacc taccagacga tgatgaagaa gaatgcgagt 300
gcgaagatga cgacgagaca acagtcgcaa ctcacatttc tacacgcagc aatggttacc 360
cttctaataa cggagccccc actagcacta aacgcccttc aaacaacgga agctcaaaca 420
atggaggctc aagctctgtc acaggatctg ttatattgag agataaatgg gtaaatggcg 480
ccaattgtat tttagctttc aagaataatg gaaacgctag agcatgtggt gtcaagttcg 540
agctgactct cggtgataat caaagaatcc aaagcatttg gaacgttgag aaagtcggag 600
ataaagttta cagaattccg gactacatcc aacttggtcc aggagtcgaa aacagagata 660
ttggagttgt ttacaatgat gtgccagaac tcttccacaa tcaaggtctt ggacaagaag 720
aaggatgcaa cattattgaa taaaaaatat ggatataaaa atatttaaaa aagattaaat 780
aagtattatt aaagcttgtg aatataaact ttttcgaaaa ttaaaataat ggcagaaaaa 840
aaaaaaaaaa aaaaaaaaaa 860

<210> SEQ ID NO 41
<211> LENGTH: 617
<212> TYPE: DNA
<213> ORGANISM: Meloidogyne incognita

<400> SEQUENCE: 41
tattaaaaaa ataacaattt cttttaaaaa taaaatgtat tcccgttcat ctttaatttc 60
tttttttctt ttaattaatt taattttgac tccaatgatt ttggctacta ataatgatgg 120
tgttgctgct ccggttgttg ctaataaaga tgctgggaaa gttagagcga cggaaattat 180
aagagcactc cgtggatttt ggaaaggagt ggcaggtgga gcattggtag gaggaggtgc 240
tgttttagct gcacggatat ttcggaacgc tggccggcgc ggatcgcccc gacccatctg 300
gatgaggtcc atctggataa tggagatgca gcatgagcgg tcctcacaga ctttcctcgg 360
tcgaactgga cgccgcgacg ctgccggcgg cgaccgcaga gatcgagcat gagcgccgcg 420
tggccatctt cgatctggtc gaaaagaaca gtttcgagcc ggtcggcgcc gagggcggcc 480
cgtatcagct gaagctgtcg ctgcaggaca accggctggt gtccggctaa attcgcattt 540
aaggaaattc gatgttttta ataatttaat ttaataaatt tgttttatct ttaaaaaaaa 600
aaaaaaaaaa aaaaaaa 617

<210> SEQ ID NO 42
<211> LENGTH: 1668
<212> TYPE: DNA
<213> ORGANISM: Meloidogyne incognita

<400> SEQUENCE: 42
attaatttta aaaatctaat taaaaatgaa ttctctctta ttaatagcat ttttatccct 60
ctcattttgt gttccaataa aggctgctcc tccatatggg caattatctg tgaaaggaag 120
tcaattagtg ggcagtaatg gacaaccagt tcaacttgtt ggaatgtcac ttttctggtc 180
gagttgtggt gaaggagaag ttttttataa taaagcaaca gtaaatagtc ttaaatgctc 240
ttggaattca aatgtagtta gggctgcaat gggtgtagag tattcagggt gccaacgacc 300
aggttatttg gatgccccaa atgttgagct gggcaaggtt gaagctgttg ttaaggccgc 360
aatagagttg gatatgtatg ttatccttga ctttcacgac cacaatgctc aacaacatgt 420
gaaacaagct atcgaattct tcacatattt tgcccaaaac tacggatcta aatacccctaa 480

```
cataatctat gagactttca atgagccact acaagtagac tggagtggtg taaagtcata    540
tcatgagcaa gttgttgcag aaattagaaa atatgacaca aagaatgtca tcgttctcgg    600
tacaacaaca tggtctcagg atgtcgatac tgctgctaac aatcctgtaa gcggcacaaa    660
cctttgctac actctacact tctacgcagc aactcataaa caaaacataa gagacaaggc    720
gcaagctgca atgaataaag gagcttgtat ctttgtaact gaatacggaa ctgttgatgc    780
aagtggaggt ggtggagtgg atgaaggttc gacaaaagaa tggtataact tcatggatag    840
taacaagatt tctaacctca actgggctat ctcaaacaag gcagaaggtg cttcagcact    900
cacatctgga acgagtgctt ctcaagttgg caatgatgac cgattgactg cctccggtgt    960
tctagtgaag aagtatatta aatcaaagaa tactggtgtc agttgcaatg gtgcatcacc   1020
aggcagtggt tcaggaagta acccctcagg aaataaaccg agcaactcac aaaccagcac   1080
tgccaaaaca tcaagcaatt caggaaataa aggcggtaat tctaacacag ggaataatgc   1140
aaataactca ggaagtaaac cgggcaactc cggaagtaat acaggaaata cgggtagcaa   1200
tgccggagcc agttcaggaa atacggggac cagtacaagc ggtagttctg ttacagcttc   1260
agtacaagtt cccgataaat gggataatgg cgcaagattc caattagtat ttaaaaacaa   1320
tgcaagtaca aaaaagtgtg cagtgaaatt ttcattgact tttgcctctg gacaacaaat   1380
tactggcatt tggaacgttc aaaatgtaac aggaaatagt tttgttcttc cagactacgt   1440
tacaattgag gcagggaaac aatatacaga tgcaggaatg aatataaatg ggccagcaac   1500
tcctccacaa attaaggtgc tcggcgatgg aaaatgcgtt ttttgaaatt aaagactccg   1560
tcttaattgt tgaattattt taatcttatg attgtttaaa ttggaaaaaa atatatgtat   1620
aatttgcttc tgttaatttt gtttatttta aatatacgat aaaaatta                1668
```

<210> SEQ ID NO 43
<211> LENGTH: 547
<212> TYPE: DNA
<213> ORGANISM: Meloidogyne incognita

<400> SEQUENCE: 43

```
taaaaaatga tttttatttc cttaattatc ctcgtattgg ctgctgaatc taatgaagca     60
agcacaaact gcaaggatgg tgaaggcgcg gtaaccttct tgtccaacca gctcggtaac    120
atacagggaa taaaaggaaa tagttattat aacaaaactt gttccaacaa aaatactgca    180
aaacgttgct acccaaatga tgaatcaaat attagcgttt ttaaaattgt ttgccccaca    240
aatatttgta tttgtggtaa tgttgataat caatgttact ctgcaaaaac agttaatcct    300
ggagatttag actatatgtt ctattctcat agtggcagca tgtttgttaa cccaaatgtt    360
ggttcaattt cattatcgtc acctgataat cattattttg atccaaagac tagtgcccca    420
aaattcatgg aattaacccc aggcacaaaa tcatatctta atgggaatga gctttctgtt    480
gcttgtacat cttgtgctaa ctttaagcag ctaacgtgtt gaacaataaa aaaaaaaaaa    540
aaaaaaa                                                              547
```

<210> SEQ ID NO 44
<211> LENGTH: 963
<212> TYPE: DNA
<213> ORGANISM: Meloidogyne incognita

<400> SEQUENCE: 44

```
gaaaataaat tattcttttt aaaattatca aaaaatgcca catttttatt taaaattttt     60
aattaattta attttattaa atttattccc attacttata aaaagcgatt tgtgtaaatt    120
```

```
tccaacggct aaggggaacc aaactgttga tgaaacaata ccattaaata aagataaaga    180

ttttgggttt attcgtctga tagcttctcc aaagttggga agttgtacaa ttgactttag    240

taagaaaatg tcgccaatat tatggttatc cgatggggtg actgttagta atttaattat    300

tggaactgaa tcttcttcag gcatttggtg tagtggaagt tgtaccttga agaatgtcta    360

ttttgaacgt gtttgtactc acgccgcagc ttttaatgca acaacagact ttacaaaaac    420

tgatagacgt tcatttacat atacagttga ggggggcgct ggactccatg ctttagataa    480

aatgtttgta caatctggcc ccggaaagac aataattaat aatttttgtg gggatggatt    540

ccaaaaagtt tggcgatcgt gtgggacgtg taatgatgaa gtgagtcaaa attctaaaca    600

aagaactgtt actataacaa attcaaattt tactggcaaa ggacatgtaa ttgcatctgg    660

aaatgcccct tataaagaca aagtttcctt caataatgtc aaaatatttg gttataaaaa    720

tcgttcaaca agagttgttt atgcctgtgg ggaagttaaa ccagaaataa gtgaagatca    780

tttagataca ggagcttcaa attggtatat acctggacgt gctggtactg gaactgtttg    840

taattatccc gcttcagcag ttaaaattgt taattaaaca ttaaaagctt gatatttaga    900

aaatagtaat aataaatgtt atttattgtg aataaagttt tataattaaa aaaaaaaaaa    960

aaa                                                                  963
```

```
<210> SEQ ID NO 45
<211> LENGTH: 720
<212> TYPE: DNA
<213> ORGANISM: Meloidogyne incognita

<400> SEQUENCE: 45

ggtttaatta cccaagttta agacaataaa ctttttaata aaaatattta attttgaatg     60

tctttgaatt ggctttattg caatttattt attgtaatac tccttttcaa cattgtaaag    120

agtgataccg atactaatgc tgatattgat cgatttgttg aaattgcaga cgatcgttta    180

actctttctg attatgttgc tttatataaa attgttaata acaaaagtat tactgatcca    240

aaacgagaag aaaaactttt gaacgatatg agaagtaagg gaaagaatct ttcgttaaat    300

gaggattatg ttactttaat attccaagac caaataaatg ctagtaaata ttttcagaat    360

tatttggtta atttatggaa tcaatcaggc attccaccta ttaaagttcg agatttaaat    420

acagacttac gcccagcaat tgatcaaata aatacagaaa tgctgcaatt gctagttaaa    480

atacaaaaac ttccctccaa agattgttta aaaaaagtag ataagtctgt aaataatttt    540

attatgagag ttaatcaaat tgatgaacaa aatgatgctt tgaaaatggc tgtgaaaggc    600

aaagacctct gccctgcatg taaacataat taacgtttag ttaattataa agggaaaaga    660

aattataatt ttgaaaaaat tttgggtttc accaaaaaaa aaaaaaaaaa aaaaaaaaaa    720
```

```
<210> SEQ ID NO 46
<211> LENGTH: 763
<212> TYPE: DNA
<213> ORGANISM: Meloidogyne incognita

<400> SEQUENCE: 46

aatacacaaa aactatttta aaaaaggcac taacttaaat aatgacttgt agtattaata     60

tttttattat tttatttatt acattaatta ttggaatatg cacggaggca aaaatccgta    120

aacaatttgt tgactctcca caggaaccac aagctaaatc ggttgatttg aatttgcaag    180

ttttaatctt tataaaaaga tgcaaatcac aattatgggc agttgggtta aataattata    240

aaacacaatt tccaaactgc tcattaattg aggaaatata ttctcgtcat tatccttttg    300
```

-continued

```
gaatgttaaa aactacacaa tggttattac aaacacttct tttattttct gcaatgtatt    360

ttccatattt tgaagttcat gatatatctt tggttgtttt tttcaccctg caattttcag    420

ttttattcac tggcttttat attattgcgc agttcatgaa agtcaaaata atccaaaacc    480

aattaatttg tctactctct tcttttctga tataatcatt tcatattgct tcactatatt    540

atttattgta cagtttatat catcaggaag atatggggca tatttgtttc tctttggatt    600

aattttgtat ggtggttatt ctttaatttt aacttttgtt tatttacgta ataatgaaga    660

tggatccttt aaattcccaa tttcaataaa aataaatgtt gaaattattc aaaaatcgga    720

taaagaatta aaacaggaaa aaaaaaaaaa aaaaaaaaaa aaa                     763
```

<210> SEQ ID NO 47
<211> LENGTH: 1706
<212> TYPE: DNA
<213> ORGANISM: Meloidogyne incognita

<400> SEQUENCE: 47

```
gacaacacaa atcaaattaa ttttaaaaat ctaattaaaa atgaattctc tcttattaat     60

agcattttta tccctctcat tttgtgttcc aataaaggct gctcctccat atgggcaatt    120

atctgtgaaa ggaagtcaat tagtgggcag taatggacaa ccagttcaac ttgttggaat    180

gtcacttttc tggtcgagtt gtggtgaagg agaagttttt tataataaag caacagtaaa    240

tagtcttaaa tgctcttgga attcaaatgt agttagggct gcaatgggtg tagagtattc    300

agggtgccaa cgaccaggtt atttggatgc cccaaatgtt gagctgggca aggttgaagc    360

tgttgttaag gccgcaatag agttggatat gtatgttatc cttgactttc acgaccacaa    420

tgctcaacaa catgtgaaac aagctatcga attcttcaca tattttgccc aaaactacgg    480

atctaaatac cctaacataa tttatgagac tttcaatgag ccactacaag tagactggag    540

tggtgtaaag tcatatcatg agcaagttgt tgcagaaatt agaaaatatg acacaaagaa    600

tgtcatcgtt ctcggtacaa caacatggtc tcaagatgtc gatactgctg ctaacaatcc    660

tgtaagcggc acaaaccttt gctacactct acacttctac gcagcaactc ataaacaaaa    720

cttaagagac aaggctcagg ctgcaatgaa taagggagct tgtatctttg taactgaata    780

cggaactgtt gatgcaagtg gaggtggtgg agtggatgaa ggttcgacaa aagaatggta    840

taacttcatg gatagtaaca agatttctaa cctcaactgg gctatctcaa acaaggcaga    900

aggtgcttca gcactcacat ctggaacgag tgcttctcaa attggcaatg atgaccgatt    960

gactgcctcc ggtcttatag tgaagaagta tattaaatca aagaatactg gtgtcagttg   1020

caatggtgca tcatcaggca gtggttccgg aaataacccc tcaggaaatg aaccgagcaa   1080

ctcacaaacc agcactgcca aaacatcaag caattcagga aataaaggcg gtaattctaa   1140

cacagggaat aatgcaaata actcaggaag taaaccgggc aactccggaa gtaatacagg   1200

aaatacgggc agcaatgctg gggcaaattc aggaaatacg gggaccagta caggcagtag   1260

ttctgttaca gcttctgtgc aagttcccga taaatgggat aatggcgcaa gattccaatt   1320

agtatttaaa aacaatgcga gtacaaaaaa gtgtgcagtg aaattttcat tgacttttgc   1380

ctctggacaa caaattactg gcatttggaa tgcccaaaat gtaacaggaa ataattttgt   1440

tcttccagac tacgttacaa ttggagcagg gaaacaatat acagatgcag gaatgaatat   1500

aaatgggcca gcaactcctc cacaaattaa ggtgctcggc gatggaaaat gcgtttttttg   1560

aaattaaaga ctccgtctaa attgttgaat tatttaatct tatgattgtt taaattggaa   1620

aataaatata tgtataattt gcttctgtta attttgttta tttaaatata cgataaaaat   1680
```

taaaaaaaaa aaaaaaaaaa aaaaaa 1706

<210> SEQ ID NO 48
<211> LENGTH: 589
<212> TYPE: DNA
<213> ORGANISM: Meloidogyne incognita

<400> SEQUENCE: 48
taaatttctt ccctaaaatt tatttaaaat tttataacaa aaaaatgttt tcaattcaag 60
gattatcttc ttttcacttc attttcctct cattattgat attattgcaa aactcttcta 120
ctgtattttc tcaacttggt tgtgattatg gatcaatgta tggcggggga atgagtggtt 180
atggccaagc aggttatgga aatgaaagta cacacatcac ttctgcccac attatattgg 240
ccaaagtgaa tcacatggtt tctcctgact tcaacaagca gggcatgaat aatctaacct 300
cccacaaaga acacgactag gaaagaaaat agaataattg gcaaacacta atgcaatcta 360
ctacagaagt caatggagaa tttacctcct aaacaggaaa atgatttgtg cctaaaagga 420
aggaagaaga acctcctctt tgttgagggg aaaagtccat aacacaggag tgcttggacc 480
caagtacaca aatataagaa cccttctagg aaaacacgag ctggggaagc agtttctctt 540
tgctattttg tgagaaaata aatgccaaaa aaaaaaaaaa aaaaaaaaa 589

<210> SEQ ID NO 49
<211> LENGTH: 660
<212> TYPE: DNA
<213> ORGANISM: Meloidogyne incognita

<400> SEQUENCE: 49
ggtttaatta cccaagttta agaaaataaa ctttttaata aaaatattta attttgaatg 60
tcttttaatt ggctttattg caatttattt attgcaatac tctttttcaa cattgtaaag 120
agtgataccg atactaatcc tgatattgat cgatttgttg aaattgcaga cgatcgttta 180
actctttctg attatgttgc tttatataaa gttgttaata atcaaagtat tactgatcca 240
aaacgagaag aaaaactttt gaacgatatg agaagtaagg gaaagaattt ttcgttaaat 300
gaggattatg ttactttaat attccaagac caaataaatg ctagtaaata ttttcagaat 360
tatttagtta atttatggaa tcaatcaggc ataccactta ttaaagttcg aaatttaaca 420
acagacttac gcccagcaat tgatcaaata aatacagaaa tgctgcaatt gctagttaaa 480
atacaaaaac ttccctccaa agattgttta aaaaaagtag ataagtctgt aaataatttt 540
attatgatag ttaatcaaat tgatgaacaa aatgatgctt tgaaaatggc tgtgaaaggc 600
aaagacctct gcccagcatg taaacataat taacgaaaaa aaaaaaaaaa aaaaaaaaaa 660

<210> SEQ ID NO 50
<211> LENGTH: 1242
<212> TYPE: DNA
<213> ORGANISM: Meloidogyne incognita

<400> SEQUENCE: 50
acgcggggaa cacaaatcga aatattttta aaaatttaat taaatgtttt ccctctcatt 60
agtagcattt ttatccctca cattttgtat tcaaattaat gctgctcctc cgtatgggca 120
attatctgtg aaaggaagtc aattagtggg cagtaatgga caaccagttc aacttgttgg 180
aatgtcactt ttctggtcga gttgtggtga aggggaaggt ttctataaca gagaaactgt 240
aaatagtctt aaatgctctt ggaattcaaa tgttgttaga gctgcaatgg gtgtagaata 300
ttctggatgc caacgaccag gttaccttga tgccccaaat gttgagctgg caaaggttga 360

```
agctgtagtg aaggcggcga ttgagttgga tatgtatgtt attcttgatt ttcacgacca    420

caatgctcag ggtcatgtga aacaagctaa acaattcttc gcatattttg cccaaaacta    480

cggatctaaa tacccaaata tcatttatga gactttcaat gagccactac aagtagactg    540

gaatggtgta aaatcatatc atgagcaagt tgttgcagaa attagaaaat atgacaataa    600

gaatgtcatc gttcttggtt caacaacttg gtctcaagat gttgatactg ccgctaataa    660

tcctgtacga ggttcaaacc tttgctattc tttacactac tacgcagcaa ctcataaaca    720

aaacttaaga gacaaggcac aggctgcaat taataaagga gcctgtatct tcgtaactga    780

gtacggaacc gttgatgcaa gtggaggtgg tggagtggat gaaggctcga caaaagagtg    840

gtataacttc ttggatagca agaaaatttc taacctcaac tgggctatct cgaacaaggc    900

agaaggggct gcagcactca cccctggaac gacttcttct caagttggca atgatgaccg    960

attgactgcc tccggtcgtc tagtgaaaag ttatattaaa tcaaagaata ctggtgtcag   1020

atgcaatgga gggggtgctg caaaaaaagg ctcttcatca tctaatactg gttcaaaaaa   1080

agacaaacaa aaattcaaag aacaaaaatt caaagaaaaa atctaacaac gccaaactgc   1140

cgaaaaaaag gtcccaaaaa gaacacttag acaaatatca aggaatttaa tgttaaatgg   1200

aatataattg ttttaaatta aaaaaaaaaa aaaaaaaaaa aa                      1242
```

<210> SEQ ID NO 51
<211> LENGTH: 1217
<212> TYPE: DNA
<213> ORGANISM: Meloidogyne incognita

<400> SEQUENCE: 51

```
ggtcattctt ataactaaaa accttcaaac ttcaaaaaat attccttaaa cttcttcaga     60

aaaataattg aaaaatgtta ttaaaattct ttttcccatt attgcttttg cttaccctta    120

tctatttggg ttgttctgag gaggataagg gagacattgc aaatggtcct caggaatctg    180

agaatcaggt tgatcaagaa ttggttagat tgaaaagaga tgatgaagaa gaggagggag    240

agaaggccga agatgaagag aaggctgaag aggatggaga taaagctgaa gatgctgaga    300

gtgcagagga gggagataag gctgaagatg ctgatgaggg agaaaaaaag agtgaagatg    360

aagagaaaaa gagtgaaggt gacgaagaaa aagcggaagg tgaagaggaa gaaaaaaagg    420

atggaactga ggaagaaaag gaggatgaag atgaagaaga gaaaaaagat gatgatgaag    480

aaaaaaatga ggaagaagaa aaaaaggatg acgaagaaga gaatggagat aaagaagaaa    540

agaaggatga tacggaagag aaagaggata aacacacaaa ggataaaagt aagaagaagg    600

atagtaagtc cgttcaaaag gataaaaagg aggaagatga caaggagaaa aaggaaaaaa    660

gttcaagtgg tgataattct aaaacagata aatcacaaaa tcaaaaacaa agcaaagaat    720

catgtaatgg ggatactgct tacaactgtc ctaaactatc aggtctttgt gaatcaaaaa    780

ttcaagtaca acaagacttc atgggtgaaa aatgttgtgc tacgtgcaaa aattcggctc    840

ctgctgcgaa gaaagatata cccctatgca ctgatttggc tgataattgt gatcaaatag    900

catccacctg tggggaagag gcgtggcaac cgactatgat ttctgattgt gctgagacct    960

gcgataagtg tgaattacat tttcaaatgt tggagaagag acttgcagca gctgctgctt   1020

aaaatttga aaggaaaaga attttatcaa aaatatatgt gtatcatatt cactaagcaa   1080

gaaattttct ttgattttca cacctttaat acgtaaaatt tcaatctatt catccgtgtt   1140

tctcgtaatt atgttttatt aattttttcg aaatttagta aaaatgcctc caaaaaaaaa   1200

aaaaaaaaaa aaaaaaa                                                  1217
```

<210> SEQ ID NO 52
<211> LENGTH: 13
<212> TYPE: PRT
<213> ORGANISM: Meloidogyne incognita

<400> SEQUENCE: 52

Gly Lys Lys Pro Ser Gly Pro Asn Pro Gly Gly Asn Asn
1 5 10

<210> SEQ ID NO 53
<211> LENGTH: 13
<212> TYPE: PRT
<213> ORGANISM: artificial sequence
<220> FEATURE:
<223> OTHER INFORMATION: shared amino acids of the functional domain of Arabidopsis CLV3-like proteins
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 53

Lys Xaa Xaa Xaa Pro Ser Gly Pro Asn Pro Xaa Xaa Asn
1 5 10

<210> SEQ ID NO 54
<211> LENGTH: 13
<212> TYPE: PRT
<213> ORGANISM: Arabidopsis sp.

<400> SEQUENCE: 54

Lys Arg Leu Val Pro Ser Gly Pro Asn Pro Leu His Asn
1 5 10

<210> SEQ ID NO 55
<211> LENGTH: 27
<212> TYPE: DNA
<213> ORGANISM: artificial sequence
<220> FEATURE:
<223> OTHER INFORMATION: primer

<400> SEQUENCE: 55
gagaaaataa aatataaatt attcctc 27

<210> SEQ ID NO 56
<211> LENGTH: 19
<212> TYPE: DNA
<213> ORGANISM: artificial sequence
<220> FEATURE:
<223> OTHER INFORMATION: primer

<400> SEQUENCE: 56
cagatataat tttattcag 19

<210> SEQ ID NO 57
<211> LENGTH: 32
<212> TYPE: DNA
<213> ORGANISM: artificial sequence
<220> FEATURE:
<223> OTHER INFORMATION: primer

<400> SEQUENCE: 57

-continued cggggtacct agatgtttac taattcaatt aa 32

<210> SEQ ID NO 58
<211> LENGTH: 31
<212> TYPE: DNA
<213> ORGANISM: artificial sequence
<220> FEATURE:
<223> OTHER INFORMATION: primer

<400> SEQUENCE: 58
cggggtacct agatgggcaa aaagcctagt g 31

<210> SEQ ID NO 59
<211> LENGTH: 26
<212> TYPE: DNA
<213> ORGANISM: artificial sequence
<220> FEATURE:
<223> OTHER INFORMATION: primer

<400> SEQUENCE: 59
gctctagatc aattatttcc tccagg 26

<210> SEQ ID NO 60
<211> LENGTH: 27
<212> TYPE: DNA
<213> ORGANISM: artificial sequence
<220> FEATURE:
<223> OTHER INFORMATION: primer

<400> SEQUENCE: 60
ggggtaccat ggattctaaa agctttg 27

<210> SEQ ID NO 61
<211> LENGTH: 33
<212> TYPE: DNA
<213> ORGANISM: artificial sequence
<220> FEATURE:
<223> OTHER INFORMATION: primer

<400> SEQUENCE: 61
ccactaggct ttttgccaag gaacaagaag cag 33

<210> SEQ ID NO 62
<211> LENGTH: 36
<212> TYPE: DNA
<213> ORGANISM: artificial sequence
<220> FEATURE:
<223> OTHER INFORMATION: primer

<400> SEQUENCE: 62
cttctgcttc ttgttccttg gcaaaaagcc tagtgg 36

<210> SEQ ID NO 63
<211> LENGTH: 26
<212> TYPE: DNA
<213> ORGANISM: artificial sequence
<220> FEATURE:
<223> OTHER INFORMATION: primer

<400> SEQUENCE: 63
gctctagatc aattatttcc tccagg 26

<210> SEQ ID NO 64
<211> LENGTH: 31
<212> TYPE: DNA
<213> ORGANISM: artificial sequence
<220> FEATURE:

<223> OTHER INFORMATION: primer

<400> SEQUENCE: 64
gatctttgcc ggaaaacaat tggaggatgg t 31

<210> SEQ ID NO 65
<211> LENGTH: 32
<212> TYPE: DNA
<213> ORGANISM: artificial sequence
<220> FEATURE:
<223> OTHER INFORMATION: primer

<400> SEQUENCE: 65
cgacttgtca ttagaaagaa agagataaca gg 32

<210> SEQ ID NO 66
<211> LENGTH: 20
<212> TYPE: DNA
<213> ORGANISM: artificial sequence
<220> FEATURE:
<223> OTHER INFORMATION: primer

<400> SEQUENCE: 66
ccggtcgtgg tcttactgat 20

<210> SEQ ID NO 67
<211> LENGTH: 20
<212> TYPE: DNA
<213> ORGANISM: artificial sequence
<220> FEATURE:
<223> OTHER INFORMATION: primer

<400> SEQUENCE: 67
gcaccgattg tgatgacttg 20

<210> SEQ ID NO 68
<211> LENGTH: 39
<212> TYPE: DNA
<213> ORGANISM: artificial sequence
<220> FEATURE:
<223> OTHER INFORMATION: primer

<400> SEQUENCE: 68
taatacgact cactataggg cctcaaaaat accataaag 39

<210> SEQ ID NO 69
<211> LENGTH: 39
<212> TYPE: DNA
<213> ORGANISM: artificial sequence
<220> FEATURE:
<223> OTHER INFORMATION: primer

<400> SEQUENCE: 69
taatacgact cactataggg gaaattaaca aaggaaacc 39

<210> SEQ ID NO 70
<211> LENGTH: 39
<212> TYPE: DNA
<213> ORGANISM: artificial sequence
<220> FEATURE:
<223> OTHER INFORMATION: primer

<400> SEQUENCE: 70
taatacgact cactataggg ggcaaaaagc ctagtgggc 39

<210> SEQ ID NO 71

<211> LENGTH: 38
<212> TYPE: DNA
<213> ORGANISM: artificial sequence
<220> FEATURE:
<223> OTHER INFORMATION: primer

<400> SEQUENCE: 71
taatacgact cactataggg tcaattattt cctccagg 38

<210> SEQ ID NO 72
<211> LENGTH: 28
<212> TYPE: DNA
<213> ORGANISM: artificial sequence
<220> FEATURE:
<223> OTHER INFORMATION: primer

<400> SEQUENCE: 72
ccgctcgagg gcaaaaagcc tagtgggc 28

<210> SEQ ID NO 73
<211> LENGTH: 27
<212> TYPE: DNA
<213> ORGANISM: artificial sequence
<220> FEATURE:
<223> OTHER INFORMATION: primer

<400> SEQUENCE: 73
cggggtacct caattatttc ctccagg 27

<210> SEQ ID NO 74
<211> LENGTH: 26
<212> TYPE: DNA
<213> ORGANISM: artificial sequence
<220> FEATURE:
<223> OTHER INFORMATION: primer

<400> SEQUENCE: 74
ccatcgattc aattatttcc tccagg 26

<210> SEQ ID NO 75
<211> LENGTH: 27
<212> TYPE: DNA
<213> ORGANISM: artificial sequence
<220> FEATURE:
<223> OTHER INFORMATION: primer

<400> SEQUENCE: 75
gctctagagg caaaaagcct agtgggc 27

<210> SEQ ID NO 76
<211> LENGTH: 28
<212> TYPE: DNA
<213> ORGANISM: artificial sequence
<220> FEATURE:
<223> OTHER INFORMATION: primer

<400> SEQUENCE: 76
ccgctcgagc ctcaaaaata ccataaag 28

<210> SEQ ID NO 77
<211> LENGTH: 28
<212> TYPE: DNA
<213> ORGANISM: artificial sequence
<220> FEATURE:
<223> OTHER INFORMATION: primer

<400> SEQUENCE: 77

-continued

```
cggggtaccg aaattaacaa aggaaacc                                    28


<210> SEQ ID NO 78
<211> LENGTH: 27
<212> TYPE: DNA
<213> ORGANISM: artificial sequence
<220> FEATURE:
<223> OTHER INFORMATION: primer

<400> SEQUENCE: 78

ccatcgatga aattaacaaa ggaaacc                                     27


<210> SEQ ID NO 79
<211> LENGTH: 27
<212> TYPE: DNA
<213> ORGANISM: artificial sequence
<220> FEATURE:
<223> OTHER INFORMATION: primer

<400> SEQUENCE: 79

gctctagacc tcaaaaatac cataaag                                     27
```

NEMATODE RESISTANT TRANSGENIC PLANTS

CROSS REFERENCE TO RELATED APPLICATION

This application is a continuation of U.S. Ser. No. 11/249,919, filed on Oct. 13, 2005, which claims benefit of and priority to U.S. provisional application No. 60/618,097 filed on Oct. 13, 2004, and U.S. provisional application No. 60/704,560 filed on Aug. 2, 2005, and where permissible each is incorporated by reference in its entirety.

STATEMENT REGARDING FEDERALLY SPONSORED RESEARCH OR DEVELOPMENT

Aspects of the work disclosed herein were supported, in part, by Grant Number 2003-35302-13804 awarded by the United States Department of Agriculture. The US government may have certain rights in the claimed subject matter.

BACKGROUND

1. Technical Field

The present disclosure generally relates to compositions for controlling plant parasites and compositions for increasing root growth, more particularly to nucleic acid compositions for controlling nematode disease or increasing root growth.

2. Related Art

Nematodes are a very large group of invertebrate animals generally referred to as roundworms, threadworms, eelworms, or nema. Some nematodes are plant parasites and can feed on stems, buds, leaves, and in particular on roots. One important genus of plant parasitic nematodes is the root-knot nematode (*Meloidogyne* spp.). These parasitic nematodes infect a wide range of important field, vegetable, fruit and ornamental plants. In 2001 the root-knot nematode was responsible for a loss of US $200.5 million in cotton alone.

Existing methods for treating or preventing root-knot nematode disease include the use of chemicals, pesticides, and fumigants. The use of pre-plant soil fumigants is highly effective in controlling root-knot and other plant-parasitic nematodes. However, the majority of the fumigant-type nematicides are no longer available and are also costly and difficult to apply properly under the prevailing conditions.

Crop rotation has also been used to control nematode disease. Rotating onion, carrot, or lettuce with a nonhost crop such as sweet corn and other grain crops, if economically possible, can be effective in controlling the northern root-knot nematode. Unfortunately, current crop rotations on organic soils are of limited value as most crops grown, including potatoes, beans, celery, lettuce, onion, and carrot are susceptible to disease.

The use of cover crops has also been attempted to control nematode disease. Cover crops grown between the main crops may provide an alternative management strategy. Ryegrain, barley, oats, sudangrass, tall fescue, annual ryegrass, and wheat have been shown to be non- or poor hosts to this nematode. Using cover crops, however, can be costly because the cover crops occupy space that could be used to grow more valuable crops.

Biological control organisms have also been used to try to control nematode disease in crops. Commercially available preparations of biological control organisms are limited in their use to regions that can support the growth of the control organism. Moreover, the outcome of using one organism to control another is unpredictable and subject to a variety of a factors such as weather and climate.

Additionally, the root-knot nematode (RKN) is a leading cause of crop loss due to plant parasitic nematodes. The most important species (*M. incognita, M. javanica, M. arenaria, M. hapla, M. chitwoodi*) have wide host ranges that limit nonhost rotation options. While several examples of host resistance genes in diverse crops exist, the availability of host plant resistance is substantially limited with appropriate resistance loci lacking for the majority of our crops (Roberts, P. A. 1992. Journal of Nematology 24:213-227). In addition, the resistance is limited to only a few RKN species or populations and some resistance genes are heat-sensitive and thus unsuitable for hot production areas. Another limitation of natural resistance genes is the durability of resistance since resistance-breaking populations of RKN can develop after continuous exposure to resistant cultivars, e.g. root-knot resistant tomatoes.

Accordingly, there is need for compositions and methods for controlling, preventing, or reducing nematode disease in plants.

Still other problems affecting crops relate to poorly developed root systems. Root systems of plants are an important part of a plant, and provide many functions that are vital to plant survival. For example, root systems store nutrients for the plant, filter out toxins, help regulate plant growth, provide an absorptive network for water and nutrients, and provide mechanical structures that support the plant and strengthen the soil. Plants with larger roots have increased growth and increased stress tolerance. Increased or enhanced root growth in crop plants would be particularly advantageous because the increased root growth would increase crop yield.

In perennial crops, increased root growth would increase the regrowth rate, increase the yield potential, and increase the likelihood that plants will survive winter. In annuals, increased root size would ensure yield potential under varying environmental conditions. In root crops, enhanced root growth would mean larger yields.

Existing root stimulators typically include fertilizers or plant hormones that must be mixed or formulated in specific concentrations when applied to the plant or soil near the plant. Over application of such stimulators can have adverse effects on the plants, and under application will not achieve the desired outcome. Additionally, application of plant hormones can have undesired consequences. For example, one plant hormone used as a root initiator is auxin or indole-3-acetic acid (IAA). IAA plays important roles in a number of plant activities, including: development of the embryo, leaf formation, phototropism, gravitropism, apical dominance, fruit development, abscission as well as root initiation.

Thus there is a need for new compositions and methods for stimulating or enhancing root growth or development.

SUMMARY

Aspects of the present disclosure generally provide nucleic acid constructs that inhibit the expression of proteins secreted by plant parasites. In some aspects, the proteins are secreted by a nematode and, optionally, modulate: gene expression of the plant or cell, formation of a giant cell, nematode migration through root tissue of the plant, cell metabolism of the plant, elicits signal transduction in the plant cell, or forms a feeding tube that enables the nematode to feed from giant-cells formed in the plant. One aspect provides inhibitory nucleic acids specific for esophageal gland cell proteins secreted by nematodes, in particular root knot nematodes. Other aspects provide transgenic cells or plants expressing or containing one or more inhibitory nucleic acids, for example inhibitory double or single stranded RNA, that inhibit or reduce the expression of nematode esophageal gland cell proteins.

Another aspect provides a transgenic plant that comprises inhibitory RNA that down regulates a target nematode parasitism gene transcript in 3, 4, 5, 6, 7, 8, 9, 10, 11, 12, 13, 14, 15, 16, 17, 18, 19, 20, or more nematode species, for example RKN species. Thus, the present disclosure provides transgenic plants that are resistant to disease caused by multiple RKN species.

Representative esophageal gland cell proteins that are targeted by the disclosed inhibitory nucleic acids include one or more of the proteins encoded by SEQ ID NOs. 1, 2, and 5-51. In certain aspects, one or more inhibitory nucleic acids are delivered to a parasitic nematode when the nematode enters the transgenic plant or transgenic plant cell, feeds on the transgenic plant or transgenic plant cell, or comes into physical contact with the transgenic plant or transgenic plant cell. Once the inhibitory nucleic acid is internalized by the parasitic nematode, the inhibitory nucleic acid interferes with, reduces, or inhibits the expression of a target esophageal gland cell protein, for example, by directly or indirectly interfering, reducing, or inhibiting the translation of one or more mRNAs coding for one or more esophageal gland cell proteins.

Yet another aspect provides a plant cell transfected with heterologous nucleic acid encoding an inhibitory nucleic acid specific for one or more nematode esophageal gland cell proteins, wherein the heterologous nucleic acid is expressed in an amount sufficient to reduce or prevent nematode disease. In one aspect, the transgenic plant expresses the inhibitory nucleic acid, and the inhibitory nucleic acid is delivered to a nematode feeding or attempting to feed on the transgenic plant. Generally, the inhibitory nucleic acid is internalized by a nematode. Exemplary methods of internalizing the inhibitory nucleic acid include ingesting the nucleic acid or absorbing the nucleic acid.

Still another aspect provides a transgenic plant comprising an inhibitory nucleic acid specific for one or more nematode parasitism polypeptides, wherein the inhibitory nucleic acid provides resistance to two or more nematode species, for example two or more root-knot nematode species.

Further aspects provide compositions for stimulating, promoting, or enhancing root growth or development in plants or trees. Certain aspects provide nucleic acid constructs encoding proteins secreted by nematode esophageal gland cells, wherein the proteins or fragments thereof stimulate or enhance root development when delivered to or in contact with a plant. Other aspects provide compositions containing one more nematode esophageal gland cell proteins or fragments thereof that stimulate root growth when in contract with a plant or plant cell. Still other aspects provide transgenic plants comprising one or more nematode esophageal gland cell proteins or fragments thereof or nucleic acids encoding one more nematode esophageal gland cell proteins or fragments thereof sufficient to stimulate, enhance, or promote root growth compared to non-transgenic or control plants.

Representative nematode esophageal gland cell proteins (also referred to as esophageal proteins) include one or more of the proteins encoded by SEQ ID NOs. 1, 2, and 5-51 or combinations thereof.

Yet another aspect provides a plant cell transfected with heterologous nucleic acid encoding one or more nematode esophageal gland cell proteins, wherein the heterologous nucleic acid is expressed in an amount sufficient to stimulate, enhance, or promote root growth or development.

The details of one or more embodiments are set forth in the accompanying drawings and the description below. Other features, objects, and advantages of the disclosure will be apparent from the description and drawings, and from the claims.

BRIEF DESCRIPTION OF THE FIGURES

FIG. 1A shows *A. thaliana* expressing 16D10 dsRNA inoculated with *M. incognita*. Note that no root knot disease (galls) on roots of *A. thaliana* expressing 16D10 dsRNA.

FIG. 1B shows control plants inoculated with *M. incognita*.

DETAILED DESCRIPTION

1. Definitions

Figure 2:
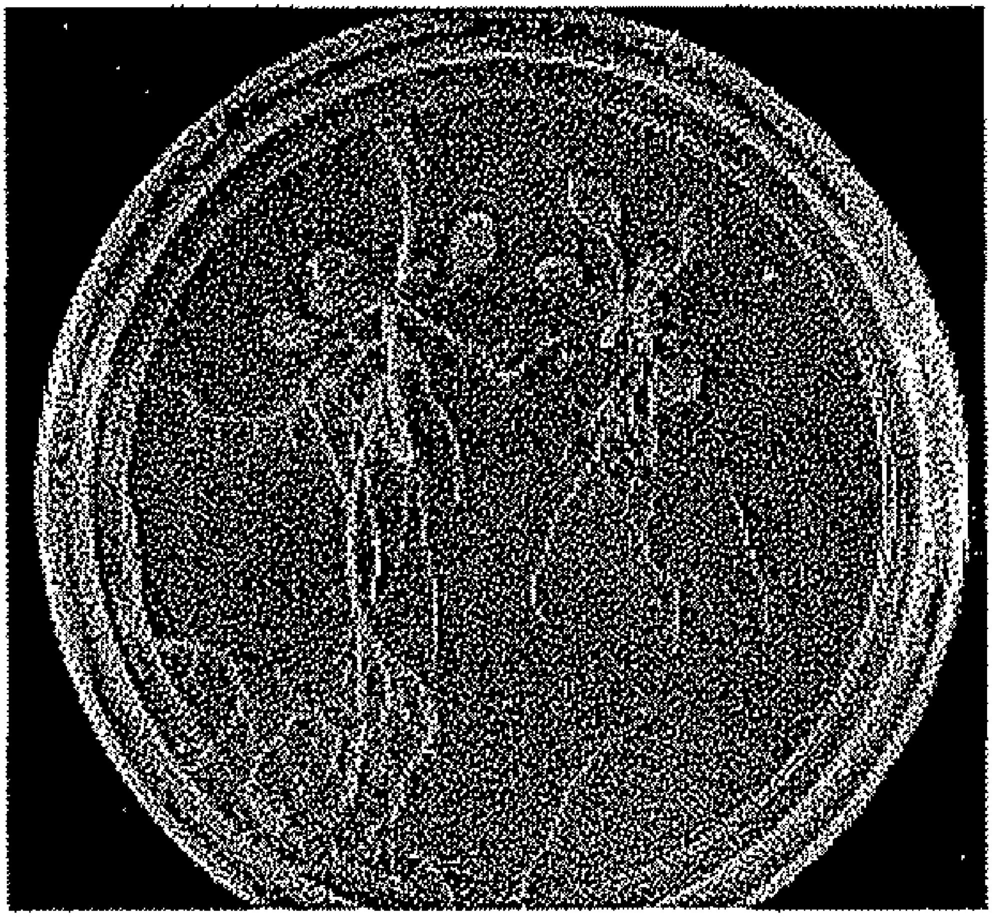
FIG. 2 shows a photograph of a transgenic *A. thaliana* plant expressing 16D10 and having enhanced root growth compared to a control plant (empty vector).

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting.

Throughout this disclosure, various publications, patents and published patent specifications are referenced. Where permissible, the disclosures of these publications, patents and published patent specifications are hereby incorporated by reference in their entirety into the present disclosure to more fully describe the state of the art. Unless otherwise indicated, the disclosure encompasses conventional techniques of plant breeding, immunology, molecular biology, microbiology, cell biology and recombinant DNA, which are within the skill of the art. See, e.g., Sambrook and Russell, Molecular Cloning: A Laboratory Manual, 3rd edition (2001); Current Protocols in Molecular Biology [(F. M. Ausubel, et al. eds., (1987)]; Plant Breeding: Principles and Prospects (Plant Breeding, Vol 1) M. D. Hayward, N, O. Bosemark, I. Romagosa; Chapman & Hall, (1993.); Coligan, Dunn, Ploegh, Speicher and Wingfeld, eds. (1995) CURRENT Protocols in Protein Science (John Wiley & Sons, Inc.); the series Methods in Enzymology (Academic Press, Inc.): PCR 2: A Practical Approach (M. J. MacPherson, B. D. Flames and G. R. Taylor eds. (1995)], Harlow and Lane, eds. (1988) Antibodies, A Laboratory Manual, and Animal Cell Culture [R. I. Freshney, ed. (1987)].

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience, 1999; and Robert A. Meyers (ed.), Molecular Biology and Biotechnology, a Comprehensive Desk Reference, published by VCH Publishers, Inc., 1995; Ausubel et al. (1987) Current Protocols in Molecular Biology, Green Publishing; Sambrook and Russell. (2001) Molecular Cloning: A Laboratory Manual 3rd. edition.

In order to facilitate understanding of the disclosure, the following definitions are provided:

To "alter" the expression of a target gene in a plant cell means that the level of expression of the target gene in a plant cell after applying a method of the present invention is different from its expression in the cell before applying the method. To alter gene expression preferably means that the expression of the target gene in the plant is reduced, preferably strongly reduced, more preferably the expression of the gene is not detectable. The alteration of the expression of an essential gene may result in a knockout mutant phenotype in plant cells or plants derived therefrom. Alternatively, altered expression can included upregulating expression of plant genes.

"Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form siRNA. These antisense and sense RNAs have been conventionally synthesized with an RNA synthesizer. In the present invention, these RNAs are intracellularly expressed from DNAs coding for antisense and sense RNAs (antisense and sense code DNAs) respectively using the siRNA expression system.

The term "biological sample" refers to a body sample from any animal, such as a mammal, for example, a human. The biological sample can be obtained from vascular, diabetic, or cancer patients, for example. A biological sample can be biological fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, cellular extracts, or whole cells or tissue. The biological sample can be, for example, serum, plasma, or urine.

As used herein, "buffer" refers to a buffered solution that resists changes in pH by the action of its acid-base conjugate components.

When referring to expression, "control sequences" means DNA sequences necessary for the expression of an operably linked coding sequence in a particular host organism. Control sequences that are suitable for prokaryotes, for example, include a promoter, optionally an operator sequence, a ribosome binding site, and the like. Eukaryotic cells are known to utilize promoters, polyadenylation signals, and enhancers.

The term "cell" refers to a membrane-bound biological unit capable of replication or division.

The term "construct" refers to a recombinant genetic molecule comprising one or more isolated polynucleotide sequences of the invention.

Genetic constructs used for transgene expression in a host organism comprise in the 5'-3' direction, a promoter sequence; a sequence encoding an inhibitory nucleic acid disclosed herein; and a termination sequence. The open reading frame may be orientated in either a sense or anti-sense direction. The construct may also comprise selectable marker gene(s) and other regulatory elements for expression.

As used herein, the term "control element" or "regulatory element" are used interchangably herein to mean sequences positioned within or adjacent to a promoter sequence so as to influence promoter activity. Control elements may be positive or negative control elements. Positive control elements require binding of a regulatory element for initiation of transcription. Many such positive and negative control elements are known. Where heterologous control elements are added to promoters to alter promoter activity as described herein, they are positioned within or adjacent the promoter sequence so as to aid the promoter's regulated activity in expressing an operationally linked polynucleotide sequence.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter.

As used herein, the term "homologues" is generic to "orthologues" and "paralogues".

The term "host plant" refers to a plant subject to nematode disease.

As used herein, the phrase "induce expression" means to increase the amount or rate of transcription and/or translation from specific genes by exposure of the cells containing such genes to an effector or inducer reagent or condition.

An "inducer" is a chemical or physical agent which, when applied to a population of cells, will increase the amount of transcription from specific genes. These are usually small molecules whose effects are specific to particular operons or groups of genes, and can include sugars, phosphate, alcohol, metal ions, hormones, heat, cold, and the like. For example, isopropyl (beta)-D-thiogalactopyranoside (IPTG) and lactose are inducers of the tacII promoter, and L-arabinose is a suitable inducer of the arabinose promoter.

The term "isolated," when used to describe the various compositions disclosed herein, means a substance that has been identified and separated and/or recovered from a component of its natural environment. For example an isolated polypeptide or polynucleotide is free of association with at least one component with which it is naturally associated. Contaminant components of its natural environment are materials that would typically interfere with diagnostic or therapeutic uses for the polypeptide or polynucleotide and may include enzymes, and other proteinaceous or non-proteinaceous solutes. An isolated substance includes the substance in situ within recombinant cells. Ordinarily, however, an isolated substance will be prepared by at least one purification step.

An "isolated" nucleic acid molecule or polynucleotide is a nucleic acid molecule that is identified and separated from at least one contaminant nucleic acid molecule with which it is ordinarily associated in the natural source. The isolated nucleic can be, for example, free of association with all components with which it is naturally associated. An isolated nucleic acid molecule is other than in the form or setting in which it is found in nature.

"IPTG" is the compound "isopropyl (beta)-D-thiogalactopyranoside", and is used herein as an inducer of lac operon. IPTG binds to a lac repressor effecting a conformational change in the lac repressor that results in dissociation of the lac repressor from the lac operator. With the lac repressor unbound, an operably linked promoter is activated and downstream genes are transcribed.

The term "lac operator" refers to a nucleic acid sequence that can be bound by a lac repressor, lacI, as described, for example, in Jacob et al., 1961, *J. Mol. Biol.,* 3: 318-356. A promoter is not activated when the lac repressor is bound to the lac operator. When the lac repressor is induced to dissociate from the operator, the promoter is activated.

The term "leader sequence" refers to a nucleic acid sequence positioned upstream of a coding sequence of interest. Leader sequences described herein contain specific sequences known to bind efficiently to ribosomes, thus delivering a greater efficiency of translation initiation of some polynucleotides.

As used herein, the term "mammal" refers to any animal classified as a mammal, including humans, domestic and farm animals, and zoo, sports, or pet animals, such as dogs, horses, cats, cows, etc. The mammal can be, for example, human.

The term "nematode esophageal glands or nematode esophageal gland cell" refers to three large, transcriptionally active gland cells, one dorsal and two subventral, located in the esophagus of a nematode and that are the principal sources of secretions (parasitism proteins) involved in infection and parasitism of plants by plant-parasitic nematodes in the orders Tylenchida and Aphelenchida.

A nucleic acid sequence or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading frame. Linking can be accomplished by ligation at convenient restriction sites. If such sites do not exist, synthetic oligonucleotide adaptors or linkers are used in accordance with conventional practice.

The term "orthologues" refers to separate occurrences of the same gene in multiple species. The separate occurrences have similar, albeit nonidentical, amino acid sequences, the degree of sequence similarity depending, in part, upon the evolutionary distance of the species from a common ancestor having the same gene.

As used herein, the term "paralogues" indicates separate occurrences of a gene in one species. The separate occurrences have similar, albeit nonidentical, amino acid sequences, the degree of sequence similarity depending, in part, upon the evolutionary distance from the gene duplication event giving rise to the separate occurrences.

The term "parasitism proteins, parasitism polypeptides, esophageal polypeptides, or nematode esophageal gland cell secretory polypeptide" refers to the principal molecules involved in nematode parasitism of plants; products of parasitism genes expressed in plant-parasitic nematode esophageal gland cells and injected through their stylet into host tissues to mediate parasitism of plants.

"Percent (%) nucleic acid sequence identity" is defined as the percentage of nucleotides in a candidate sequence that are identical with the nucleotides in a reference nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

The term "plant" is used in it broadest sense. It includes, but is not limited to, any species of woody, ornamental or decorative, crop or cereal, fruit or vegetable plant, and photosynthetic green algae (e.g., *Chiamydomonas reinhardtii*). It also refers to a plurality of plant cells that are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

A non-naturally occurring plant refers to a plant that does not occur in nature without human intervention. Non-naturally occurring plants include transgenic plants and plants produced by non-transgenic means such as plant breeding.

The term "plant cell" refers to a structural and physiological unit of a plant, comprising a protoplast and a cell wall. The plant cell may be in form of an isolated single cell or a cultured cell, or as a part of higher organized unit such as, for example, a plant tissue, a plant organ, or a whole plant.

The term "plant cell culture" refers to cultures of plant units such as, for example, protoplasts, cell culture cells, cells in plant tissues, pollen, pollen tubes, ovules, embryo sacs, zygotes and embryos at various stages of development.

The term "plant material" refers to leaves, stems, roots, flowers or flower parts, fruits, pollen, egg cells, zygotes, seeds, cuttings, cell or tissue cultures, or any other part or product of a plant.

A "plant organ" refers to a distinct and visibly structured and differentiated part of a plant such as a root, stem, leaf, flower bud, or embryo.

"Plant tissue" refers to a group of plant cells organized into a structural and functional unit. Any tissue of a plant whether in a plant or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

As used herein, "polypeptide" refers generally to peptides and proteins having more than about ten amino acids. The polypeptides can be "exogenous," meaning that they are "heterologous," i.e., foreign to the host cell being utilized, such as human polypeptide produced by a bacterial cell.

"Primate" is construed to mean any of an order of mammals comprising humans, apes, monkeys, and related forms, such as lemurs and tarsiers.

The term "promoter" refers to a regulatory nucleic acid sequence, typically located upstream (5') of a gene or protein coding sequence that, in conjunction with various elements, is responsible for regulating the expression of the gene or protein coding sequence. The promoters suitable for use in the constructs of this disclosure are functional in plants and in host organisms used for expressing the inventive polynucleotides. Many plant promoters are publicly known. These include constitutive promoters, inducible promoters, tissue- and cell-specific promoters and developmentally-regulated promoters. Exemplary promoters and fusion promoters are described, e.g., in U.S. Pat. No. 6,717,034, which is herein incorporated by reference in its entirety.

"Purifying" means increasing the degree of purity of a substance in a composition by removing (completely or partially) at least one contaminant from the composition. A "purification step" may be part of an overall purification process resulting in an "essentially pure" composition. An essentially pure composition contains at least about 90% by weight of the substance of interest, based on total weight of the composition, and can contain at least about 95% by weight.

The term "regulatory element" or "control element" refers to DNA sequences controlling initiation of transcription. Examples of control or regulatory elements include, but are not limited to, a TATA box, operators, enhancers, and the like. Regulatory or control elements include negative control elements and positive control elements. A negative control element is one that is removed for activation. Many such negative control elements are known, for example operator/repressor systems. For example, binding of IPTG to the lac repressor dissociates from the lac operator to activate and permit transcription. Other negative elements include the *E. coli* trp and lambda systems. A positive control element is one that is added for activation. Many such positive control elements are known.

Promoters naturally containing both positive and negative regulatory elements are rare. The metE promoter is one example. See, for example, Neidhardt, Ed., 1996, *Escherishia coli* and *Salmonella*, Second Ed., pages 1300-1309. Descriptions of known positive and negative control elements can be found, for example, in this reference. Positioning of a positive or negative control element within or adjacent to the promoter to achieve added regulation of the promoter is known, and is described, for example, in *Escherishia coli* and *Salmonella* (Supra) at pages 1232-1245.

Small RNA molecules are single stranded or double stranded RNA molecules generally less than 200 nucleotides in length. Such molecules are generally less than 100 nucleotides and usually vary from 10 to 100 nucleotides in length. In a preferred format, small RNA molecules have 11, 12, 13, 14, 15, 16, 17, 18, 19, 20, 21, 22, 23, 24, 25, 26, 27, 28, 29 or 30 nucleotides. Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded.

The term "siRNA" means a small interfering RNA that is a short-length double-stranded RNA that is not toxic. Generally, there is no particular limitation in the length of siRNA as long as it does not show toxicity. "siRNAs" can be, for example, 15 to 49 bp, preferably 15 to 35 bp, and more preferably 21 to 30 by long. Alternatively, the double-stranded RNA portion of a final transcription product of siRNA to be expressed can be, for example, 15 to 49 bp, preferably 15 to 35 bp, and more preferably 21 to 30 by long. The double-stranded RNA portions of siRNAs in which two RNA strands pair up are not limited to the completely paired ones, and may contain nonpairing portions due to mismatch (the corresponding nucleotides are not complementary), bulge (lacking in the corresponding complementary nucleotide on one strand), and the like. Nonpairing portions can be contained to the extent that they do not interfere with siRNA formation. The "bulge" used herein preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, in the present invention, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 by double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end.

In addition, the terminal structure of the "siRNA" is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 by long. Alternatively, the length of the double-stranded RNA region that is a final transcription product of siRNAs to be expressed is, for example, 15 to 49 bp, preferably 15 to 35 bp, and more preferably 21 to 30 by long. Furthermore, there is no particular limitation in the length of the linker as long as it has a length so as not to hinder the pairing of the stem portion. For example, for stable pairing of the stem portion and suppression of the recombination between DNAs coding for the portion, the linker portion may have a clover-leaf tRNA structure. Even though the linker has a length that hinders pairing of the stem portion, it is possible, for example, to construct the linker portion to include introns so that the introns are excised during processing of precursor RNA into mature RNA, thereby allowing pairing of the stem portion. In the case of a stem-loop siRNA, either end (head or tail) of RNA with no loop structure may have a low molecular weight RNA. As described above, this low molecular weight RNA may be a natural RNA molecule such as tRNA, rRNA or viral RNA, or an artificial RNA molecule.

"Signal peptide" refers to a short (15-60 amino acids long) peptide chain that directs the post translational transport of a protein; usually directs the peptide to the secretory pathway of the cell.

"Transformed," "transgenic," "transfected" and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

A "transformed cell" refers to a cell into which has been introduced a nucleic acid molecule, for example by molecular biology techniques, As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

The term "transgenic plant" refers to a plant or tree that contains recombinant genetic material not normally found in plants or trees of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

The term "translation initiation enhancer sequence", as used herein, refers to a nucleic acid sequence that can determining a site and efficiency of initiation of translation of a gene (See, for example, McCarthy et al., 1990*, Trends in Genetics,* 6: 78-85). A translation initiation enhancer sequence can extend to include sequences 5' and 3' to the ribosome binding site. The ribosome binding site is defined to include, minimally, the Shine-Dalgarno region and the start codon, in addition to any bases in between. In addition, the translation initiation enhancer sequence can include an untranslated leader or the end of an upstream cistron, and thus a translational stop codon. See, for example, U.S. Pat. No. 5,840,523.

The term "vector" refers to a nucleic acid molecule which is used to introduce a polynucleotide sequence into a host cell, thereby producing a transformed host cell. A "vector" may comprise genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

2. Exemplary Embodiments

Nematode Resistant Transgenic Plants

It has been discovered that interrupting the feeding cycle of nematodes by down-regulating one or more nematode parasitism genes is an effective method for reducing, preventing, or treating nematode disease in plants. Nematode parasitism genes refers to genes expressed in the esophageal gland cells encoding for secretory proteins exported from the gland cell to be released through the nematode's stylet into host tissue. In particular, it has been discovered that interfering with the expression of proteins secreted by nematodes related to the formation of specialized feeding cells in host plants is an effective method for reducing, treating, or preventing nematode disease in plants. Representative parasitism genes encoding secreted proteins that can be targeted, for example with inhibitory RNA include, include but are not limited to those genes listed in Table 2, or a fragment thereof.

Nematode disease results in substantial losses of valuable crops. Root-knot nematodes, *Meloidogyne* species, are among nature's most successful parasites. They parasitize more than 2,000 plant species from diverse plant families and represent a tremendous threat to crop production world-wide. These biotrophic pathogens have evolved highly specialized and complex feeding relationships with their hosts. A successful nematode-host interaction requires molecular signals from the parasite to modify, directly or indirectly, plant root cells into elaborate feeding cells, called giant-cells, which are the sole source of nutrients needed for nematode development and reproduction. Plant-parasitic nematodes release proteinaceous secretions through a hollow protrusible stylet into plant cells when feeding. These secretions, collectively called the parasitome are encoded by parasitism genes expressed in large and transcriptionally active esophageal gland cells (Davis, E. L., R. Allen, and R. S. Hussey. 1994. Developmental expression of esophageal gland antigens and their detection in stylet secretions of *Meloidogyne incognita*. Fundam.

Appl. Nematol. 17:255-262; Hussey, R. S., E. L. Davis, and T. J. Baum. 2002. Secrets in secretions: genes that control nematode parasitism of plants. Braz. J. Plant Physiol. 14:183-194.). The profound cellular modifications induced by *Meloidogyne* species to form the giant-cells are the result of an alteration in host root cell gene expression and phenotype that is driven by the molecular signals secreted through the nematode's stylet.

One embodiment provides a plant or cell comprising one or more inhibitory RNAs specific for one or more mRNAs of one or more nematode parasitism genes. For example, the present disclosure provides transgenic plants that express one or more inhibitory RNAs that down regulate nematode parasitism gene expression when the one or more inhibitory RNAs are absorbed or ingested by a nematode. The transgenic plant can be designed to express inhibitory RNA that down-regulates the target parasitism gene transcript in at least two different nematode species, for example two different RKN species. Another embodiment provides a transgenic plant that comprises inhibitory RNA that down regulates the target parasitism gene transcript in 3, 4, 5, 6, 7, 8, 9, 10, 11, 12, 13, 14, 15, 16, 17, 18, 19, 20, or more nematode species, for example RKN species. Thus, the present disclosure provides transgenic plants that are resistant to disease caused by multiple RKN species.

Another embodiment, provides a transgenic plant comprising inhibitory RNA specific for one or more nematode parasitism genes in an amount effective to provide the plant with resistance to all RKN species, for example those RKN species referenced in Jepson, S. B. 1987. Identification of root-knot nematodes (*Meloidogyne* species). C. A. B. International, Oxford, United Kingdom. 1-265 pages, which, where permissible, is incorporated by reference in its entirety.

Another embodiment provides a transgenic plant or transgenic cell containing or expressing one or more inhibitory nucleic acids specific for at least a portion of a nucleic acid encoding one or more secretory polypeptides of a parasitic nematode. The inhibitory nucleic acid is typically a small inhibitory RNA or microRNA that is specific for mRNA encoding a nematode esophageal gland cell protein or polypeptide. It will be appreciated by one of skill in the art that the inhibitory nucleic acid can be RNA, DNA, or a combination thereof. Additionally, the inhibitory nucleic acid may be single or multi-stranded and may be anti-sense or enzymatic. In one embodiment, the inhibitory nucleic acid interferes, inhibits, or reduces the translation of a target mRNA. For example, the inhibitory nucleic acid can bind to a target mRNA and induce or promote the degradation of the target mRNA or physically prevent the cellular translational machinery from translating the target mRNA into a functional protein. Inhibition of the secretory polypeptide can be compared to controls, for example plants or cells that do not contain or express the inhibitory nucleic acid. A "control" refers to a sample of material which is known to be identical to a sample containing the disclosed inhibitory nucleic acid in every regard, except that the control sample does not contain or express the inhibitory nucleic acid.

The term "esophageal gland cell protein or polypeptide" refers to a secretory polypeptide encoded by a nematode parasitism gene. In one embodiment, the esophageal gland cell protein or polypeptide to be down-regulated generally is a secreted protein that modulates expression of at least one host plant gene. Exemplary nematode polypeptides that are down-regulated in the disclosed compositions and methods include, but are not limited to polypeptides or fragments thereof encoded by SEQ ID NOs 1, 2, or 5-51, or fragments thereof. The secretory polypeptide can increase or decrease expression of host plant genes either directly or indirectly. For example, direct modulation can occur when the esophageal gland cell protein or polypeptide binds to a host plant nucleic acid, including genomic DNA, RNA, and mRNA. Indirect modulation can occur for example when the polypeptide binds with one or more other proteins or factors to form a complex. The complex can then bind to a host plant nucleic acid to either promote or suppress transcription or translation. Down-regulation of the secretory protein alleviates or reduces at least one symptom associated with nematode disease. Exemplary symptoms of nematode disease include, but are not limited to the formation of galls, giant cells, lesions, stunting, nutrient and water deficiencies, dieback, and numbers of nematodes infecting a plant. Levels of reduction or inhibition of nematode disease in transgenic plants or cells can be compared to levels of nematode disease in control plants or cells. In one embodiment, the inhibitory nucleic acid reduces, inhibits, alleviates, treats or prevents nematode disease.

In another embodiment, the esophageal gland cell protein or polypeptide to be down-regulated is encoded by a parasitism gene involved in the formation of a giant cell. In still other embodiments, the targeted parasitism gene encodes a polypeptide or nucleic acid involved in nematode migration through root tissue, alters cell metabolism, elicits signal transduction in the recipient cell, or forms a feeding tube that enables the nematode to feed from the giant-cells. Additionally, the esophageal gland cell protein or polypeptide can cause cell wall modifications and potentially interact with signal transduction receptors in the extracellular space, influence cellular metabolism, cell cycle, selective protein degradation, localized defense response, and regulatory activity within the plant cell nucleus.

Exemplary plant genes that are modulated by the esophageal gland cell protein or polypeptide include, but are not limited to genes involved in the formation of specialized nematode feeding cells also known as giant cells. For example, nematode parasitism gene 16D10 encodes a protein that binds to a scarecrowlike transcription regulator. Representative plant genes that can be modulated by nematode esophageal gland cell polypeptides include, but are not limited to WUN1, PDX, CAT, GST, Mia-1, Mia-2, Mia-3, Mia-4, CHS1-CHS3, LOX, Chitinase, Trypsin inhibitor, Miraculin, HMGR, TSW12, LEA14, LEMMI9, C6-19, C27-45, TAS14, UBC DB#103, RPE, ISDGh, IPPP, LPPL, mUCp, endomembrane protein, 20s proteasome, DAP decarboxylase, GRP, ENOD40, ATAO1 or combinations thereof (Gheysen, G. and Fenoll, C. 2002. Annual Review of Phytopathology 40:191, which, where permissible, is incorporated by reference in its entirety). Generally, the plant gene is directly or indirectly involved in root cell growth, root cell division or the production of specific nutrients ingested by the parasitic nematode. The gene can be one expressed in a root cell or any other cell of the plant.

In one embodiment, expression of a targeted nematode secretory protein is reduced, inhibited, or blocked, as compared to a control, when the inhibitory nucleic acid is delivered to the nematode. Delivery of the inhibitory nucleic acid can be achieved, for example, when the nematode comes into contact with the inhibitory nucleic acid as the nematode feeds on the transgenic plant or cell. The nematode can ingest the inhibitory nucleic acid during feeding, or the nucleic acid can be transported across a cellular membrane of the nematode by active transport or passive diffusion. It will be appreciated that the inhibitory nucleic acid can be delivered to the nematode in combination or alternation with an agent that induces or promotes the uptake of the inhibitory nucleic acid by the nematode. An exemplary inducing agent includes, but is not limited to resorcinol (3-hydroxyphenol).

In one embodiment, the transgenic plant or transgenic cell expresses the inhibitory nucleic in an amount effective to modulate the expression of a nematode esophageal gland cell polypeptide or protein in a nematode when the inhibitory nucleic acid is delivered to the nematode. Levels of expression of the inhibitory nucleic acid in a transgenic plant or cell can be controlled using methods known in the art, for example using vectors with strong promoters or constitutively active promoters, high copy number vectors, etc. The plant or cell can be stably or transiently transfected.

An exemplary parasitic nematode includes, but is not limited to members of *Meloidogyne* spp. also referred to as root-knot nematodes. Representative species include, but are not limited to *M. arenaria, M. incognita, M. javanica, M. hapla, M. chitwoodi* and *M. naasi.*

Representative phylogenetic families of host plants include Acanthaceae, Aceraceae, Actinidiaceae, Agavaceae, Aizoaceae, Amarantliaceae, Annonaceae, Apiaceae, Apocynaceae, Araceae, Araliaceae, Arecaceae, Aristolochiaceae, Balsaminaceae, Barringtoniaceae, Basellaceae, Berberidaceae, Betulaceae, Bignoniaceae, Bixaceae, Bombacaceae, Boraginaceae, Buxaceae, Byttneriaceae, Cactaceae, Caesalpiniaceae, Cannaceae, Capparaceae, Caprifoliaceae, Caricaceae, Caryophyllaceae, Casuarinaceae, Casuarinaceae, Celastraceae, Chenopodiaceae, Chenopodiaceae, Chloranthaceae, Commelinaceae, Convolvulaceae, Cornaceae, Corylaceae, Crassulaceae, Cucurbitaceae, Cupressaceae, Cyatheaceae, Cyperaceae, Datiscaceae, Dilleniaceae, Dioscoreaceae, Dipsacaceae, Ebenaceae, Ericaceae, Euphorbiaceae, Fabaceae, Flacourtiaceae, Fumariaceae, Gentianaceae, Geraniaceae, Gesneriaceae, Ginkgoaceae, Goodeniaceae, Guttiferae, Haemodoraceae, Hamamelidaceae, Heliconiaceae, Hydrophyllaceae, Hypericaceae, Iridaceae, Juglandaceae, Juncaceae, Labiatae, Lamiaceae, Lauraceae, Liliaceae, Linaceae, Lobeliaceae, Loganiaceae, Lythraceae, Magnoliaceae, Malpighiaceae, Malvaceae, Marantaceae, Melastomataceae, Meliaceae, Menispermaceae, Mimosaceae, Moraceae, Musaceae, Myoporaceae, Myricaceae, Myristicaceae, Myrtaceae, Nyctaginaceae, Oleaceae, Onagraceae, Orchidaceae, Othnaceae, Oxalidaceae, Paeoniaceae, Pandanaceae, Papaveraceae, Pedaliaceae, Phytolaccaceae, Pinaceae, Piperaceae, Pittosporaceae, Plantaginaceae, Platanaceae, Plumbaginaceae, Poaceae, Podostemaceae, Polemoniaceae, Polygalaceae, Portulacaceae, Primulaceae, Proteaceae, Punicaceae, Ranunculaceae, Resedaceae, Rhamnaceae, Rosaceae, Rubiaceae, Rutaceae, Salicaceae, Santalaceae, Sapindaceae, Sarraceniaceae, Saxifragaceae, Scrophulariaceae, Smilacaceae, Solanaceae, Sterculiaceae, Styracaceae, Tamaricaceae, Taxodiaceae, Tetragoniaceae, Theaceae, Theophrastaceae, Thymetaeaceas, Tiliaceae, Tropaeolaceae, Turneraceae, Typhaceae, Ulmaceae, Urticaceae, Valerianaceae, Verbenaceae, Violaceae, Vitaceae, Zamiaceae, Zingiberaceae, or Zygophyllaceae.

Common names of host plants that can be transfected with an inhibitory nucleic acid according the present disclosure include, but are not limited to tomato, eggplant, potato, melon, cucumber, carrot, lettuce, artichoke, celery, cucurbits (melon, watermelon, etc.), barley, corn, peanut, soybean, sugar beet, cotton, cowpea, beans, alfalfa, tobacco, citrus, clover, pepper, grape, coffee, olive, or tea.

It will be appreciated by one of skill in the art that the present disclosure encompasses any of the fifty or more known root-knot nematode species.

Another embodiment provides a composition having an inhibitory nucleic acid specific for an mRNA or fragment thereof encoding a polypeptide encoded by one or more of SEQ ID NOs. 1, 2 or 5-51 or a fragment or homologues thereof, in an amount sufficient to inhibit expression of the polypeptide encoded by one or more of SEQ ID NOs 1, 2 or 5-51 or homologues thereof when delivered to a nematode, for example when the nematode is feeding on a plant or cell expressing or containing the inhibitory nucleic acid. The composition can contain one or more nematicides, pesticides, fungicides, or combinations thereof. Representative nematicides include, but are not limited to chloropicrin, methyl bromide, 1,3-dichloropropene, sodium methyl dithiocarbamate, sodium tetrathiocarbonate; and carbamates such as 2-methyl-2-(methylthio)propionaldehyde O-methylcarbamoyloxime (aldicarb), 2,3-Dihydro-2,2-dimethyl-7-benzofuranol methylcarbamate (carbofuran), methyl 2-(dimethylamino)-N-[[methylamino)carbonyl]oxy]-2-oxo-ethanimidothioate (oxamyl), 2-methyl-2-(methylsulfonyl) propanal O-[(methylamino)carbonyl]oxime (aldoxycarb), O,O-diethyl O-[4-(methylsulfinyl)phenyl]phosphorothioate (fensulfothion), O-Ethyl S,S-dipropylphosphorodithioate (ethoprop), and Ethyl-3-methyl-4-(methylthio)phenyl(1-methylethyl)phosphoramidate (phenamiphos).

Another embodiment provides a cell containing a nucleic acid encoding an inhibitory nucleic acid specific for an mRNA or fragment thereof, wherein the mRNA encodes a esophageal gland cell protein or polypeptide that directly or indirectly modulates: root cell gene expression, nematode migration through root tissue, cell metabolism, signal transduction, or is involved in the formation of a feeding tube that enables the nematode to feed from the giant-cells of at least one plant gene involved in the formation of a giant cell. Additionally, the esophageal gland cell protein or polypeptide or esophageal polypeptide can cause cell wall modifications and potentially interact with signal transduction receptors in the extracellular space, influence cellular metabolism, cell cycle, selective protein degradation, localized defense response, and regulatory activity within the plant cell nucleus. The cell can be prokaryotic or eukaryotic, and generally is a plant cell, particularly a root cell.

Still another embodiment provides a method for providing nematode resistance to a plant by contacting the plant with one or more inhibitory nucleic acids specific for one or more nematode esophageal gland cell proteins in an amount sufficient to reduce nematode disease, wherein the one or more nematode esophageal gland cell proteins modulate: gene expression of the plant or cell, formation of a giant cell, nematode migration through root tissue of the plant, cell metabolism of the plant, elicits signal transduction in the plant cell, or forms a feeding tube that enables the nematode to feed from giant-cells formed in the plant. One aspect provides inhibitory nucleic acids specific for esophageal gland cell proteins secreted by nematodes, in particular root knot nematodes. The inhibitory nucleic acid can be sprayed onto the plant or otherwise delivered to the plant so that the inhibitory nucleic acid comes into contact with a parasitic nematode.

Yet another embodiment provides transgenic plants or plant cells containing an inhibitory nucleic acid, for example siRNA or microRNA, that down regulates root-knot nematode esophageal gland cell proteins when delivered to a nematode feeding on the plant or plant cell. RNA interference is known in the art. See for example, Kreutzer et al., International PCT Publication No. WO 00/44895; Zernicka-Goetz et al, International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; Li et al., International PCT Publication No. WO 00/44914; and Trick et al., US20040098761.

In one embodiment, the nematode is not a soybean cyst nematode.

In another embodiment, the inhibitory nucleic acid is not directly lethal to embryonic or adult nematodes or is not involved in nematode fertility, but instead inhibits the ability of the nematode to feed on or obtain nutrients from the transgenic plant or plant cell.

In some embodiments, inhibitory double stranded RNA (dsRNA) is derived from an "exogenous template". Such a template may be all or part of a plant or nematode nucleotide sequence; it may be a DNA gene sequence or a cDNA produced from an mRNA isolated from a parasitic nematode, for example by reverse transcriptase. When the template is all or a part of a DNA gene sequence, it is preferred if it is from one or more or all exons of the gene. While the dsRNA is derived from an endogenous or exogenous template, there is no limitation on the manner in which it could be synthesized. For example, the siRNA can be chemically synthesized, produced by in vitro transcription; produced by digestion of long dsRNA by an RNase III family enzyme (e.g., Dicer, RNase III); expressed in cells from an siRNA expression plasmid or viral vector; or expressed in cells from a PCR-derived siRNA expression cassette SiRNA prepared in vitro is then introduced directly into cells by transfection, electroporation, or by another method. Alternatively, transfection of DNA-based vectors and cassettes that express siRNAs within the cells can be used. RNAi may be synthesized in vitro or in vivo, using manual and/or automated procedures. In vitro synthesis may be chemical or enzymatic, for example using cloned RNA polymerase (e.g., T3, T7, SP6) for transcription of the endogenous DNA (or cDNA) template, or a mixture of both.

In vivo, the dsRNA may be synthesised using recombinant techniques well known in the art (see e.g., Sambrook, et al., Molecular Cloning; A Laboratory Manual, Third Edition (2001). For example, bacterial cells can be transformed with an expression vector which comprises the DNA template from which the dsRNA is to be derived. Alternatively, the cells, of a plant for example, in which inhibition of gene expression is required may be transformed with an expression vector or by other means. Bidirectional transcription of one or more copies of the template may be by endogenous RNA polymerase of the transformed cell or by a cloned RNA polymerase (e.g., T3, T7, SP6) coded for by the expression vector or a different expression vector. The use and production of an expression construct are known in the art (see WO98132016; U.S. Pat. Nos. 5,593,874, 5,698,425, 5712, 135, 5,789,214, and 5,804,693). Inhibition of gene expression may be targeted by specific transcription in an organ, tissue, or cell type; an environmental condition (e.g. temperature, chemical); and/or engineering transcription at a developmental stage or age, especially when the dsRNA is synthesized in vivo in the plant cell for example. dsRNA may also be delivered to specific tissues or cell types using known gene delivery systems. Components of these systems include the seed-specific lectin promoter and the flower specific promoter from APETALA3. These vectors are listed solely by way of illustration of the many commercially available and well known vectors that are available to those of skill in the art.

If synthesized outside the cell, the RNA may be purified prior to introduction into the cell. Purification may be by extraction with a solvent (such as phenol/chloroform) or resin, precipitation (for example in ethanol), electrophoresis, chromatography, or a combination thereof. However, purification may result in loss of dsRNA and may therefore be minimal or not carried out at all. The RNA may be dried for storage or dissolved in an aqueous solution, which may contain buffers or salts to promote annealing, and/or stabilization of the RNA strands.

Suitable dsRNA can also contain one or more modified bases, or have a modified a backbone to increase stability or for other reasons. For example, the phosphodiester linkages of natural RNA may be modified to include at least one of a nitrogen or sulfur heteroatom. Moreover, dsRNA comprising unusual bases, such as inosine, or modified bases, such as tritylated bases, to name just two examples, can be used. It will be appreciated that a great variety of modifications have been made to RNA that serve many useful purposes known to those of skill in the art. The term dsRNA as it is employed herein embraces such chemically, enzymatically or metabolically modified forms of dsRNA, provided that it is derived from an endogenous template.

The double-stranded structure may be formed by a single self-complementary RNA strand or two separate complementary RNA strands. RNA duplex formation may be initiated either inside or outside the plant cell.

The sequence of at least one strand of the dsRNA contains a region complementary to at least a part of the target mRNA sufficient for the dsRNA to specifically hybridize to the target mRNA. In one embodiment, the siRNA is substantially identical to at least a portion of the target mRNA. "Identity", as known in the art, is the relationship between two or more polynucleotide (or polypeptide) sequences, as determined by comparing the sequences. In the art, identity also means the degree of sequence relatedness between polynucleotide sequences, as determined by the match between strings of such sequences. Identity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, N.J., 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide sequences, the term is well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. Applied Math., 48: 1073 (1988). Methods commonly employed to determine identity between sequences include, but are not limited to those disclosed in Carillo, H., and Lipman, D., SIAM J. Applied Math., 48:1073 (1988). Preferred methods to determine identity are designed to give the largest match between the sequences tested. Methods to determine identity are codified in computer programs. Computer program methods to determine identity between two sequences include, but are not limited to, GCG program package (Devereux, J., et al., Nucleic Acids Research 12(1): 387 (1984)), BLASTP, BLASTN, and FASTA (Atschul, S. F. et al., J. Molec. Biol. 215: 403 (1990)). Another software package well known in the art for carrying out this procedure is the CLUSTAL program. It compares the sequences of two polynucleotides and finds the optimal alignment by inserting spaces in either sequence as appropriate. The identity for an optimal alignment can also be calculated using a software package such as BLASTx. This program aligns the largest stretch of similar sequence and assigns a value to the fit. For any one pattern comparison several regions of similarity may be found, each having a different score. One skilled in the art will appreciate that two polynucleotides of different lengths may be compared over the entire length of the longer fragment. Alternatively small regions may be compared. Normally sequences of the same length are compared for a useful comparison to be made.

In one embodiment, the inhibitory nucleic acid has 100% sequence identity with at least a part of the target mRNA. However, inhibitory nucleic acids having 70%, 80% or greater than 90% or 95% sequence identity may be used. Thus sequence variations that might be expected due to genetic mutation, strain polymorphism, or evolutionary divergence can be tolerated.

The duplex region of the RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

While the optimum length of the dsRNA may vary according to the target gene and experimental conditions, the duplex region of the RNA may be at least 19, 20, 21-23, 25, 50, 100, 200, 300, 400 or more bases long.

Target genes are nematode genes encoding secreted proteins, in particular secreted proteins that modulate: gene expression of the plant or cell, formation of a giant cell, nematode migration through root tissue of the plant, cell metabolism of the plant, elicits signal transduction in the plant cell, or forms a feeding tube that enables the nematode to feed from giant-cells formed in the plant. One aspect provides inhibitory nucleic acids specific for esophageal gland cell proteins secreted by nematodes, in particular root knot nematodes. Typically, the dsRNA or inhibitory nucleic acid is substantially identical to the whole of the target gene, i.e. the coding portion of the gene. However, the dsRNA or inhibitory nucleic acid can be substantially identical to a part of the target gene. The size of this part depends on the particular target gene and can be determined by those skilled in the art by varying the size of the dsRNA and observing whether expression of the gene has been inhibited.

Plants with Enhanced Root Growth

One embodiment provides a transgenic plant or transgenic cell containing or expressing one or more nucleic acids encoding one or more nematode esophageal gland cell polypeptides or fragments thereof of a parasitic nematode. Expression of the one or more nematode esophageal gland cell polypeptides or fragments thereof in a plant or plant cell promotes, stimulates, or enhances root growth of the transgenic plant compared to non-transgenic plants or control plants. A root includes a seminal root, adventitious root, first order lateral root, second order laterals, etc., feeder roots primary roots, secondary roots, and coarse roots.

The nematode esophageal gland cell polypeptides or fragments used with the disclosed embodiments can increase the size of roots, the number of roots, the surface area of roots, and the overall quality of a root system. Root crops can be produced with the disclosed compositions and methods that are larger than root crops produced in the absence of the disclosed compositions and methods. Other crops produced using the disclosed compositions and methods can be resistant to drought, erosion, or increased environmental stress. Environmental stress includes changes in climate such as rainfall, temperature, and humidity.

Exemplary nematode esophageal gland cell polypeptides or fragments thereof include, but are not limited to polypeptides encoded by SEQ ID NOs 1, 2, or 5-51, fragments thereof, or combinations thereof. The nematode esophageal gland cell polypeptides or fragments can increase, stimulate, or enhance root growth directly or indirectly. For example, direct modulation can occur when the nematode secretory polypeptide binds to a host plant nucleic acid, including genomic DNA, RNA, and mRNA. Indirect modulation can occur for example when the polypeptide binds with one or more other proteins or factors to form a complex. The complex can then bind to a host plant nucleic acid to either promote or suppress transcription or translation.

In one embodiment, the transgenic plant or transgenic cell expresses the nematode esophageal gland cell polypeptide or fragment thereof in an amount effective to stimulate, enhance or promote root growth or development. Alternatively, the nematode esophageal gland cell polypeptide or fragment thereof can be delivered directly to the plant. Levels of nematode esophageal gland cell polypeptide or fragment thereof expression in a transgenic plant or cell can be controlled using methods known in the art, for example using vectors with strong promoters or constitutively active promoters, high copy number vectors, etc. The plant or cell can be stably or transiently transfected.

An exemplary nematode includes, but is not limited to members of *Meloidogyne* spp. also referred to as root-knot nematodes. Representative species include, but are not limited to *M. arenaria, M. incognita, M. javanica, M. hapla*, and *M. naasi.*

Representative phylogenetic families of host plants include Acanthaceae, Aceraceae, Actinidiaceae, Agavaceae, Aizoaceae, Amaranthaceae, Annonaceae, Apiaceae, Apocynaceae, Araceae, Araliaceae, Arecaceae, Aristolochiaceae, Balsaminaceae, Barringtoniaceae, Basellaceae, Berberidaceae, Betulaceae, Bignoniaceae, Bixaceae, Bombacaceae, Boraginaceae, Buxaceae, Byttneriaceae, Cactaceae, Caesalpiniaceae, Cannaceae, Capparaceae, Caprifoliaceae, Caricaceae, Caryophyllaceae, Casuarinaceae, Casuarinaceae, Celastraceae, Chenopodiaceae, Chenopodiaceae, Chloranthaceae, Commelinaceae, Convolvulaceae, Cornaceae, Corylaceae, Crassulaceae, Cucurbitaceae, Cupressaceae, Cyatheaceae, Cyperaceae, Datiscaceae, Dilleniaceae, Dioscoreaceae, Dipsacaceae, Ebenaceae, Ericaceae, Euphorbiaceae, Fabaceae, Flacourtiaceae, Fumariaceae, Gentianaceae, Geraniaceae, Gesneriaceae, Ginkgoaceae, Goodeniaceae, Guttiferae, Haemodoraceae, Hamamelidaceae, Heliconiaceae, Hydrophyllaceae, Hypericaceae, Iridaceae, Juglandaceae, Juncaceae, Labiatae, Lamiaceae, Lauraceae, Liliaceae, Linaceae, Lobeliaceae, Loganiaceae, Lythraceae, Magnoliaceae, Malpighiaceae, Malvaceae, Marantaceae, Melastomataceae, Meliaceae, Menispermaceae, Mimosaceae, Moraceae, Musaceae, Myoporaceae, Myricaceae, Myristicaceae, Myrtaceae, Nyctaginaceae, Oleaceae, Onagraceae, Orchidaceae, Othnaceae, Oxalidaceae, Paeoniaceae, Pandanaceae, Papaveraceae, Pedaliaceae, Phytolaccaceae, Pinaceae, Piperaceae, Pittosporaceae, Plantaginaceae, Platanaceae, Plumbaginaceae, Poaceae, Podostemaceae, Polemoniaceae, Polygalaceae, Portulacaceae, Primulaceae, Proteaceae, Punicaceae, Ranunculaceae, Resedaceae, Rhamnaceae, Rosaceae, Rubiaceae, Rutaceae, Salicaceae, Santalaceae, Sapindaceae, Sarraceniaceae, Saxifragaceae, Scrophulariaceae, Smilacaceae, Solanaceae, Sterculiaceae, Styracaceae, Tamaricaceae, Taxodiaceae, Tetragoniaceae, Theaceae, Theophrastaceae, Thymelaeaceae, Tiliaceae, Tropaeolaceae, Turneraceae, Typhaceae, Ulmaceae, Urticaceae, Valerianaceae, Verbenaceae, Violaceae, Vitaceae, Zamiaceae, Zingiberaceae, or Zygophyllaceae.

Common names of host plants that can be transfected with nucleic acid encoding a RKN esophageal gland cell secretory polypeptide according the present disclosure include, but are not limited to tomato, eggplant, potato, melon, cucumber, carrot, lettuce, artichoke, celery, cucurbits (melon, watermelon, etc.), barley, corn, peanut, soybean, sugar beet, cotton, cowpea, beans, alfalfa, tobacco, citrus, clover, pepper, grape, coffee, olive, or tea.

It will be appreciated by one of skill in the art that the present disclosure encompasses any nematode that secretes a protein that alters the expression of a host gene. For example, one embodiment provides a transgenic plant or cell containing a nucleic acid encoding a protein secreted by a member of *Meloidogyne* spp., wherein the secreted protein stimulates, enhances, or promotes root growth or development.

Another embodiment provides a composition comprising a nucleic acid having a sequence of SEQ ID NOs. 1, 2 or 5-51 or a fragment or homologues thereof. The composition stimulates, promotes, or enhances root growth or development when delivered to a plant or plant cell.

Still another embodiment provides a composition comprising a one or more polypeptides or fragments thereof encoded by SEQ ID NOs 1, 2 or 5-51 or homologues thereof when delivered to a plant or plant cell.

Root stimulating compositions disclosed herein can optionally contain a growth enhancer, fertilizer, one or more nemiticides, pesticides, fungicides, or combinations thereof. Representative nematicides include, but are not limited to chloropicrin, methyl bromide, 1,3-dichloropropene, sodium methyl dithiocarbamate, sodium tetrathiocarbonate; and carbamates such as 2-methyl-2-(methylthio)propionaldehyde O-methylcarbamoyloxime (aldicarb), 2,3-Dihydro-2,2-dimethyl-7-benzofuranol methylcarbamate (carbofuran), methyl 2-(dimethylamino)-N-[[(methylamino)carbonyl]oxy]-2-oxoethanimidothioate (oxamyl), 2-methyl-2-(methylsulfonyl)propanal O-[(methylamino)carbonyl]oxime (aldoxycarb), O,O-diethyl O-[4-(methylsulfinyl)phenyl] phosphorothioate (fensulfothion), O-Ethyl S,S-dipropylphosphorodithioate (ethoprop), and Ethyl-3-methyl-4-(methylthio)phenyl(1-methylethyl)phosphoramidate (phenamiphos).

Another embodiment provides a cell, for example a plant cell, containing one or more nucleic acids encoding a nematode secretory polypeptide or fragment thereof wherein the nematode secretory polypeptides directly or indirectly stimulate, enhance or promote root growth or development. The cell can be prokaryotic or eukaryotic, and generally is a plant cell, particularly a root cell.

Still another embodiment provides a method for providing drought resistance to a plant by contacting the plant with one or more nematode esophageal proteins or nucleic acids encoding nematode esophageal proteins in an amount sufficient to stimulate, promote, or enhance root development. The composition can be sprayed onto the plant, applied to the soil surrounding the plant or otherwise delivered to the plant so that the composition contacts the plant.

Plant Transformation Technology

DNA molecules and RNA molecules of the present disclosure are incorporated in plant or bacterial cells using conventional recombinant DNA technology. Generally, a DNA or an RNA molecule of the present disclosure is comprised in a transformation vector. A large number of such vector systems known in the art may be used, such as plasmids. The components of the expression system are also modified, e.g., to increase expression of the introduced RNA fragments. For example, truncated sequences, nucleotide substitutions or other modifications may be employed. Expression systems known in the art may be used to transform virtually any plant cell under suitable conditions. A transgene comprising a DNA molecule of the present invention is preferably stably transformed and integrated into the genome of the host cells. Transformed cells are preferably regenerated into whole plants. Detailed description of transformation techniques are within the knowledge of those skilled in the art.

Reporter genes or selectable marker genes may be included in the expression cassette. Examples of suitable reporter genes known in the art can be found in, for example, Jefferson et al. (1991) in Plant Molecular Biology Manual, ed. Gelvin et al. (Kluwer Academic Publishers), pp. 1-33; DeWet et al. (1987) Mol. Cell. Biol. 7:725-737; Goff et al. (1990) EMBO J. 9:2517-2522; Kain et al. (1995) Bio Techniques 19:650-655; and Chiu et al. (1996) Current Biology 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) EMBO J. 2:987-992); methotrexate (Herrera Estrella et al. (1983) Nature 303:209-213; Meijer et at (1991) Plant Mal. Biol. 16:807-820); hygromycin (Waldron et al, (1985) Plant Mol. Biol. 5:103-108; Zhijian et al. (1995) Plant Science 108:219-227); streptomycin (Jones et al. (1987) Mol. Gen. Genet 210:86-91); spectinomycin (Bretagne-Sagnard et al. (1996) Transgenic Res. 5:131-137); bleomycin (Hille et al. (1990) Plant Mol. Biol. 7:171-176); sulfonamide (Guerineau et al. 1990) Plant Mol. Biol. 15:127-136); bromoxynil (Stalker et al. (1988) Science 242:41 9423); glyphosate (Shaw et al. (1986) Science 233:478-481); phosphinothricin (DeBlock et al. (1987) EMBO J. 6:2513-2518).

Other genes that could serve utility in the recovery of transgenic events but might not be required in the final product would include, but are not limited to, examples such as GUS (b-glucoronidase; Jefferson (1987) Plant Mol. Biol. Rep. 5:387), GFP (green florescence protein; Chalfie et al. (1994) Science 263:802), luciferase (Riggs et al. (1987) Nucleic Acids Res. 15(19):8115 and Luehrsen et al. (1992) Methods Enzymol. 216:397-414) and the maize genes encoding for anthocyanin production (Ludwig et al. (1990) Science 247:449).

The expression cassette comprising a promoter sequence operably linked to a heterologous nucleotide sequence of interest can be used to transform any plant. In this manner, genetically modified plants, plant cells, plant tissue, seed, and the like can be obtained.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606, *Agrobacterium*-mediated transformation (Townsend et al., U.S. Pat. No. 5,563,055; Zhao et al. WO US98/01268), direct gene transfer (Paszkowski et al. (1984) EMBO J. 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Dafta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference in their entirety.

The cells that have been transformed may be grown into plants in accordance with conventional techniques. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize 1 n2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227:229-237, and U.S. Pat. Nos. 5,814,618 and 5,789,156), herein incorporated by reference in their entirety.

Constitutive promoters include, for example, the core promoter of the Rsyn7 promoter and other constitutive promoters disclosed in WO 99/43838 and U.S. Pat. No. 6,072,050; the core CAMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142.

Where low level expression is desired, weak promoters may be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142.

"Tissue-preferred" promoters can be used to target a gene expression within a particular tissue. Tissue-preferred promoters include Yamamoto et al. (1997) Plant J. 12(2)255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sol. USA 90(20):9586-9590; and Guevara-Garcia et al. (1993) Plant J. 4(3):495-505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and ce1A (cellulose synthase). Gama-zein is a preferred endosperm-specific promoter. Glob-1 is a preferred embryo-specific promoter. For dicots, seed-specific promoters include, but are not limited to, bean.beta.-phaseolin, napin, beta.-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Leaf-specific promoters are known in the art. See, for example, Yamamoto et al. (1997) Plant J. 12(2):255-265; Kwon et al. (1994) Plant Physiol. 105:357-67; Yamamoto et al. (1994) Plant Cell Physiol. 35(5):773-778; Gotor et al. (1993) Plant J. 3:509-18; Orozco et al. (1993) Plant Mol. Biol. 23(6):1129-1138; and Matsuoka et al. (1993) Proc. Natl. Acad. Sci. USA 90(20):9586-9590.

Root-preferred promoters are known and may be selected from the many available from the literature or isolated de novo from various compatible species. See, for example, Hire et al. (1992) Plant Mol. Biol. 20(2): 207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3(1):I 1'-22 (full-length cDNA clone encoding cytosolic glutamine synthetase (GS), which is expressed in roots and root nodules of soybean). See also U.S. Pat. Nos. 5,837,876; 5,750,386; 5,633,363; 5,459,252; 5,401,836; 5,110,732; and 5,023,179.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J. Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263:14996-14999). See also Von Heijne et al. (1991) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

Methods for transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation may be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plants transformed in accordance with the present disclosure may be monocots or dicots and include, but are not limited to, any nematode host plant.

Requirements for Construction of Plant Expression Cassettes

Nucleic acid sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

Promoters

The selection of the promoter used in expression cassettes determine the spatial and temporal expression pattern of the transgene in the transgenic plant. Selected promoters express transgenes in specific cell types (such as leaf epidermal cells, mesophyll cells, root cortex cells) or in specific tissues or organs (roots, leaves or flowers, for example) and the selection reflects the desired location of accumulation of the gene product. Alternatively, the selected promoter drives expression of the gene under various inducing conditions.

Promoters vary in their strength, i.e., ability to promote transcription. Depending upon the host cell system utilized, any one of a number of suitable promoters known in the art may be used. For example, for constitutive expression, the CaMV 35S promoter, the rice actin promoter, or the ubiquitin promoter may be used. For example, for regulatable expression, the chemically inducible PR-1 promoter from tobacco or *Arabidopsis* may be used (see, e.g., U.S. Pat. No. 5,689,044).

A suitable category of promoters is that which is wound inducible. Numerous promoters have been described which are expressed at wound sites. Preferred promoters of this kind include those described by Stanford et al. Mal. Gen. Genet. 215: 200-208 (1989), Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), and Warner et al. Plant J. 3: 191-201 (1993).

Suitable tissue specific expression patterns include green tissue specific, root specific, stem specific, and flower specific. Promoters suitable for expression in green tissue include many which regulate genes involved in photosynthesis, and many of these have been cloned from both monocotyledons and dicotyledons. A suitable promoter is the maize PEPC promoter from the phosphoenol carboxylase gene (Hudspeth & Grula, Plant Molec. Biol. 12: 579-589 (1989)). A suitable promoter for root specific expression is that described by de Framond (FEBS 290: 103-106 (1991); EP 0 452 269 and a root-specific promoter is that from the T-1 gene. A suitable stem specific promoter is that described in U.S. Pat. No. 5,625,136 and which drives expression of the maize trpA gene.

Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adh1 gene have been shown to enhance expression, particularly in monocotyledonous cells. In addition, a number of non-translated leader sequences derived from viruses are also known to enhance expression, and these are particularly effective in dicotyledonous cells.

Coding Sequence Optimization

The coding sequence of the selected gene may be genetically engineered by altering the coding sequence for optimal expression in the crop species of interest. Methods for modifying coding sequences to achieve optimal expression in a particular crop species are well known (see, e.g. Perlak et al., Proc. Natl. Acad. Sci. USA 88: 3324 (1991); and Koziel et al, Bio/technol. 11: 194 (1993)).

Another embodiment provides an RNA molecule directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). The presence of cloning sites between these markers allowed creation of a plastid targeting vector for introduction of foreign DNA molecules (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19: 4083-4089). Other selectable markers useful for plastid transformation are known in the art and are encompassed within the scope of the invention.

Construction of Plant Transformation Vectors

Numerous transformation vectors available for plant transformation are known to those of ordinary skill in the plant transformation arts, and the genes pertinent to this disclosure can be used in conjunction with any such vectors. The selection of vector depends upon the selected transformation technique and the target species for transformation. For certain target species, different antibiotic or herbicide selection markers are preferred. Selection markers used routinely in transformation include the npt11 gene, which confers resistance to kanamycin and related antibiotics (Messing & Vierra. Gene 19: 259-268 (1982); Bevan et al., Nature 304: 184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph gene, which confers resistance to the antibiotic hygromycin (Blochinger & Diggeimann, Mol Cell Biol 4: 2929-2931), the manA gene, which allows for positive selection in the presence of mannose (Miles and Guest (1984) Gene, 32: 41-48; U.S. Pat. No. 5,767,378), and the dhfr gene, which confers resistance to methotrexate (Bourouis et al., EMBO J. 2 (7): 1099-1104 (1983)), and the EPSPS gene, which confers resistance to glyphosate (U.S. Pat. Nos. 4,940,935 and 5,188,642).

Many vectors are available for transformation using *Agrobacterium tumefaciens*. These typically carry at least one T-DNA border sequence and include vectors such as pBIN19 (Bevan, Nucl. Acids Res. (1984). Typical vectors suitable for *Agrobacterium* transformation include the binary vectors pCIB200 and pCIB2001, as well as the binary vector pCIB 10 and hygromycin selection derivatives thereof. (See, for example, U.S. Pat. No. 5,639,949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Typical vectors suitable for non-*Agrobacterium* transformation include pCIB3064, pSOG 19, and pSOG35. (See, for example, U.S. Pat. No. 5,639,949).

Transformation Techniques

Once the DNA sequence of interest is cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus *Agrobacterium* can be utilized to transform plant cells.

Transformation techniques for dicotyledons are well known in the art and include *Agrobacterium*-based techniques and techniques that do not require *Agrobacterium*. Non *Agrobacterium* techniques involve the uptake of exogenous genetic material directly by protoplasts or cells. This is accomplished by PEG or electroporation mediated uptake, particle bombardment-mediated delivery, or microinjection. In each case the transformed cells may be regenerated to whole plants using standard techniques known in the art.

Transformation of most monocotyledon species has now become somewhat routine. Preferred techniques include direct gene transfer into protoplasts using PEG or electroporation techniques, particle bombardment into callus tissue or organized structures, as well as *Agrobacterium*-mediated transformation.

Plants from transformation events are grown, propagated and bred to yield progeny with the desired trait, and seeds are obtained with the desired trait, using processes well known in the art. The methods can result in plant cells comprising the RNA fragments of the present invention, wherein the expression of said target gene in said plant cell is altered by said RNA fragments, a plant and the progeny thereof derived from the plant cell, and seeds derived from the plant.

The disclosed inhibitory nucleic acids or RKN esophageal gland cell secretory polypeptides may be used alone or as a component of a kit having at least one of the reagents necessary to carry out the in vitro or in vivo introduction of RNA to subjects. Suitable components are the dsRNA and a vehicle that promotes introduction of the dsRNA. Such a kit may also include instructions to allow a user of the kit to practice the invention.

Another embodiment provides a method for providing resistance to nematode disease by introducing into a nematode host plant cell an RNA comprising a double stranded structure having a nucleotide sequence which is complementary to at least a part of the target mRNA; and optionally verifying inhibition of expression of the target mRNA.

One embodiment provides a method for treating or preventing nematode disease in a plant by contacting a parasitic nematode in or on the plant with a with dsRNA having a sequence which is complementary to at least a part of a mRNA encoding a nematode secretory protein, for example an esophageal gland cell protein; wherein the secretory protein modulates gene expression of plant.

Still another embodiment provides a plant cell, for example, containing an expression construct, the construct coding for an RNA which forms a double stranded structure having a nucleotide sequence which is complementary to at least a part of a target mRNA that encodes a nematode secretory protein, for example an esophageal gland cell protein, as well as a transgenic plant containing such a cell.

In another embodiment, the RNA fragments are comprised in two different RNA molecules. In this case, the RNA fragments are mixed before being introduced into said cell, e.g. under conditions allowing them to form a double-stranded RNA molecule. In another embodiment, the RNA fragments are introduced into said cell sequentially. Preferably, the time interval between the introduction of each of the RNA molecules is short, preferably less than one hour.

In still another embodiment, the RNA fragments are comprised in one RNA molecule. By using one single RNA molecule, the two complementary RNA fragments are in close proximity such that pairing and double strand formation is favored. In such case, the RNA molecule is preferably capable of folding such that said RNA fragments comprised therein form a double-stranded region. In this case, the complementary parts of the RNA fragments recognize one another, pair with each other and form the double-stranded RNA molecule. In another embodiment, the RNA fragments are incubated under conditions allowing them to form a double-stranded RNA molecule prior to introduction into the cell. In yet another embodiment, the RNA molecule comprises a linker between the sense RNA fragment and the antisense RNA fragment. The linker preferably comprises a RNA sequence encoded by an expression cassette comprising a functional gene, e.g. a selectable marker gene. In another embodiment, the linker comprises a RNA sequence encoded by regulatory sequences, which e.g. comprise intron processing signals.

Another embodiment provides a dsRNA construct having a promoter operably linked to said dsRNA and might further comprise said dsRNA molecule. The promoter can be a heterologous promoter, for example a tissue specific promoter, a developmentally regulated promoter, a constitutive promoter, divergent or an inducible promoter. Termination signal are also optionally included in the DNA molecules.

The single RNA molecule or the two distinct RNA molecules are preferably capable of forming a double-stranded region, in which the complementary parts of the RNA fragments recognize one another, pair with each other and form the double-stranded RNA molecule.

Another embodiment provides the disclosed transgenic plant material in the form of feedstock, pellets, granules, flakes and the like. The inhibitory nucleic acids disclosed here can be in seeds and seed products derived from the transgenic plants described above. Another embodiment provides a composition comprising the disclosed inhibitory nucleic acids that can be coated on seeds. The coating can be formulated so that the inhibitory nucleic acids remain able to inhibit nematode secretory proteins as the seed matures and develops roots.

A further embodiment provides chimeric or fusion proteins containing the disclosed nematode esophageal gland cell proteins or fragments thereof. As used herein, a "chimeric protein" or "fusion protein" includes a nematode esophageal gland cell protein or fragment thereof linked to a foreign polypeptide. A "foreign polypeptide" is polypeptide that is not substantially homologous to a nematode esophageal gland cell protein or fragment thereof. The foreign polypeptide can be fused to the N-terminus or C-terminus of the nematode esophageal gland cell protein or fragment thereof.

The fusion protein can include a moiety which has a high affinity for a ligand. For example, the fusion protein can be a GST fusion protein in which a nematode esophageal gland cell protein or fragment thereof is fused to the C-terminus of GST. Such fusion proteins can facilitate the purification of the polypeptide. Alternatively, the fusion protein can contain a heterologous signal sequence at its N-terminus. In certain host cells, expression, secretion or transport of a protein can be increased through use of a heterologous signal sequence. For example, in a plant cell, a polypeptide of the invention may be fused with a chloroplast transit peptide. The chloroplast transit peptide allows the polypeptide to be transported from the cytoplasm of the plant cell into the chloroplast, thereby increase root growth. Expression vectors are commercially available that already encode a fusion moiety (e.g., a GST polypeptide). A nucleic acid encoding a nematode esophageal gland cell protein or fragment thereof can be cloned into such an expression vector so that the fusion moiety is linked in-frame to the polypeptide.

The following are only exemplary examples. It should be understood that the invention is not limited to these examples. Other important applications of disclosure would be readily recognized by those of ordinary skills in the art. Other uses which are potentially recognizable by those of ordinary skills in the art are also part of the disclosure.

The references mentioned herein are incorporated in their entirety to the fullest extent permitted by applicable law.

EXAMPLES

Example 1

Nematodes and Plants

*Meloidogyne* species were propagated on roots of greenhouse-grown tomato (*Lycopersicon esculentum* cv. Marion or Better-Boy). *Meloidogyne* eggs were collected as described (Hussey and Barker, 1973). Pre-parasitic second-stage juveniles (pre-J2) were collected via hatching eggs on 25-µw-pore sieves in deionized water in plastic bowls. The different parasitic stages of *M. incognita* were collected by root blending and sieving (Ding et al. 1998). Mixed parasitic stages (MS) of *M. incognita* for in situ hybridizations were collected 13-15 days after inoculation of eggs as described in De Boer et al. (1998). Similarly, pre-J2 and MS of *Heterogera glycines* were collected from infected soybean (*Glycine max*) roots. *Caenorhabditis elegans* was cultured on OP50 of *E. coli* (Brenner, 1974). One-month-old host plant leaves were collected from growth-chamber grown *Nicotiana tabacum* cv. Petite Havana SR1, and *Arabidopsis thaliana* ecotype Col-0.

Example 2

Nucleic Acid Manipulation

Pre-J2 of packed nematodes were frozen in 1.5-ml microcentrifuge tubes with liquid nitrogen and ground with a smooth-end metal bar. The frozen nematode fragments were mixed with 0.5 ml extraction solution (100 mM NaCl, 100 mM Tris-HCl [pH8.0], 50 mM EDTA, 1% sodium dodecyl sulfate, 4 mg/ml proteinase K and 10 µg/ml RNase) and incubated at 37° C. for 1 hr. DNA was extracted with phenol/chloroform and then precipitated with isopropanol (Sambrook et al., 1989). The DNA was re-suspended in $H_2O$.

Tobacco and *Arabidopsis* genomic DNA was extracted using standard techniques (Dellaporta 1993).

mRNAs were extracted and purified from ground plant tissues using Dynabeads mRNA DIRECT kit (Dynal, Lake Success, N.Y.), eluted with 10 μl diethylpyrocarbonate (DEPC)-treated water, and converted into first-strand cDNA by reverse transcription (RT)-PCR SMART PCR cDNA Synthesis kit (BD Biosciences, Palo Alto, Calif.), following the manufacturer's instructions. RT-PCR reactions contained the following components: 4.0 μl of 5× first-strand buffer, 2.0 μl of 20 mM DTT, 2.0 μl of 10 mM 50× dNTP, 1 μl of 10 μM 3'-CDS primer, 10 μl of isolated mRNA and 1 μl of Superscript II reverse transcriptase (200 units/μl, Gibco BRL, Rockville, Md.). The reaction was incubated at 42° C. for 1 hr.

Example 3

Isolation of 16D10 cDNA Clone

Clone 16D10 encoding a secretory signaling peptide was identified during random sequencing of a gland-cell specific cDNA library of *M. incognita* (Huang et al., 2003) and designated as 16D10. The full-length double-strand cDNA sequences of 16D10 in pGEM-T Easy vector were obtained by using T7 and SP6 primers in sequencing reactions. The longest open reading frame of the 16D10 cDNA (364 bp) encoded a deduced protein of 43 aa including a 30 aa N-terminal hydrophobic signal peptide as predicted by Signal P (Nielsen et al, 1997). While the mature 16D10 peptide of 13 aa (GKKPSGPNPGGNN, $M_r$ 1,223 Da) (SEQ ID NO:52) provided no significant BLASTX similarity, it did contain 8 aa (K-PSGPNP-N) (SEQ ID NO:53) of the conserved C-terminal 13 aa motif (KRLVPSGPNPLHN) (SEQ ID NO:54) of the functional domain of *Arabidopsis* CLV3-like proteins (Cock and McCormick, 2001) as well as a cAMP/cGMP-dependent protein kinase phosphorylation site [KKpS] as predicted by PROSITE (Hofmann et al., 1999).

Example 4

Genomic Clones in *Meloidogyne* Species

One pair of the gene-specific primers 16D10GF (5'-GAGAAAATAAAATATAAATTATTCCTC-3') (SEQ ID NO:55) and 16D10GR (5'-CAGATATAATTTTATTCAG-3') (SEQ ID NO:56) designed from the most extreme 5'- and 3'-ends of the cDNA sequence of *M. incognita* 16D10, were used to amplify the corresponding genomic sequences (or the highest homologues) from 200 ng of *M. incognita, M. javanica, M. arenaria* and *M. hapla* genomic DNA. The PCR products were cut from a 1.2% agarose gel, and purified with a QIAquick gel extraction kit (Qiagen, Valencia, Calif.). The purified products were cloned into pGEM-T Easy vector (Promega, Madison, Wis.) for sequencing. The 16D10 homologues from the *Meloidogyne* species shared over 95% identity at the nucleotide level and the deduced proteins encoded by putative cDNAs were identical to that of *M. incognita* 16D10.

Example 5

Southern Blot Analysis

Figure 6:
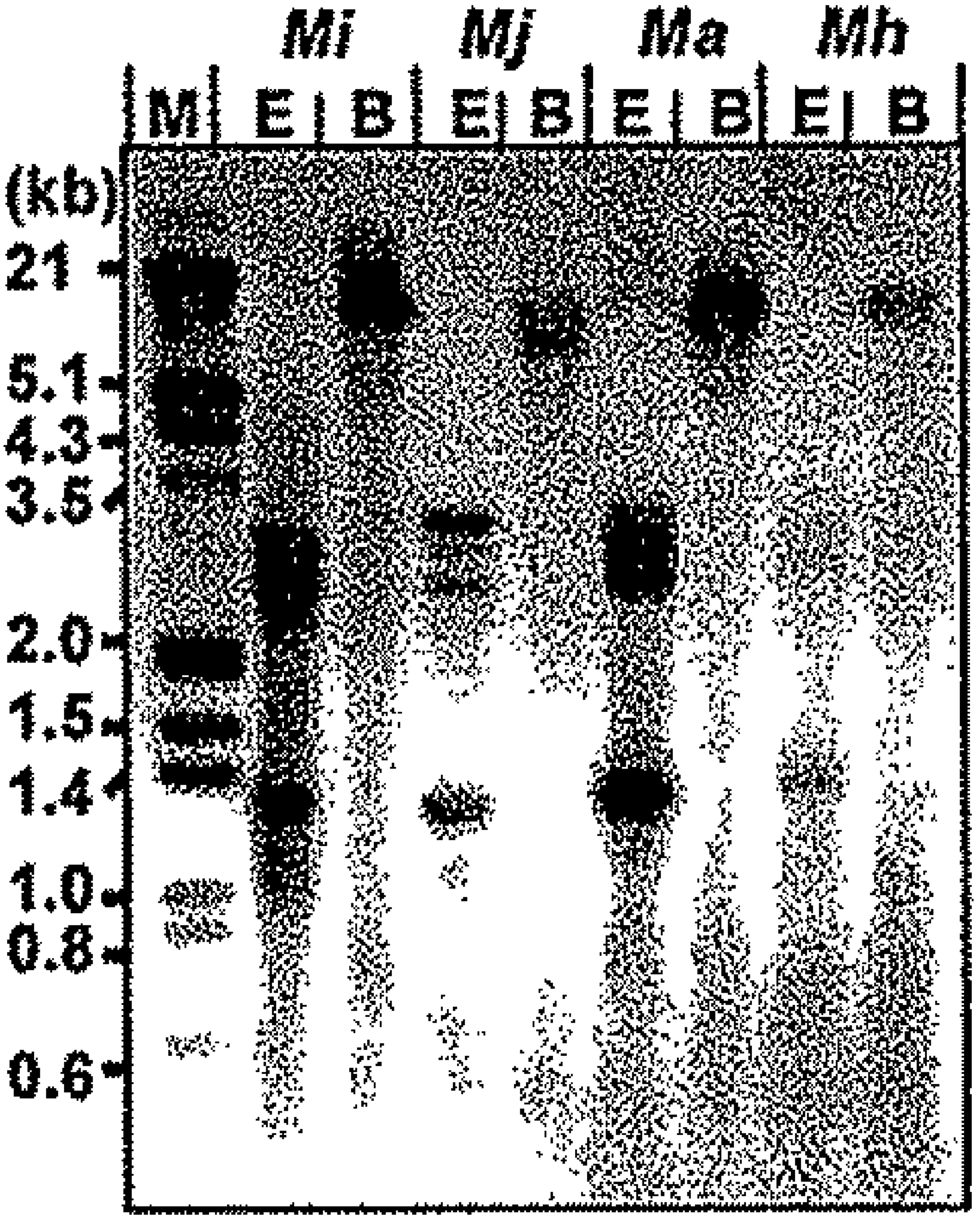
FIG. 6 shows DNA blot hybridization of restriction endonuclease-digested genomic DNA from four *Meloidogyne* species with a DIG-labeled 16D10 probe. Mi, *M. incognita*; Mj, *M. javanica*; Ma, *M. arenaria*; Mh, *M. hapla*. E, EcoRI; B, BamHI. M, 80 ng DIG-labeled molecular weight marker in kb.

For each sample, 10 μg of genomic DNA was completely digested with 50 units of EcoRI or BamHI (New England Biolabs, Beverly, Mass.), separated on a 0.7% (w/v) agarose gel, transferred onto a Hybond-N Nylon membranes (Amersham Pharmacia Biotech, Piscataway, N.J.) and blotting using a standard protocol (Sambrook et al., 1989). 16D10 probe was generated by amplification of the corresponding full-length cDNA from insert in pGEM-T Easy vector with T7 and SP6 primers. Gel-purified PCR products were labeled by PCR with a PCR-DIG probe synthesis system (Roche Applied Science, Indianapolis, Ind.). About 15 ng of DIG-labeled probe per ml was used for each-hybridization. Hybridizations were performed in DIG Easy Hyb solution (Roche Applied Science, Indianapolis, Ind.) at 40° C. for 16 h followed by two 5-min washes in 2×SSC/0.1% SDS solution at RT. The membranes were then washed twice at 68° C. with 0.5×SSC/0.1% SDS solution for 30 min. After incubating the membrane in 1% blocking reagent for 1 hr, the membranes were incubated with a 1:10,000 dilution of sheep anti-DIG alkaline phosphatase (AP) conjugate for 30 min. Unbound antibody was removed by two 15-min washes with maleic acid washing buffer (100 mM maleic acid, 150 mM NaCl, pH7.5, and 0.3% Tween 20). The membrane was incubated in AP detection buffer (100 mM Tris-HCl, pH9.5, 100 mM NaCl, and 50 mM $MgCl_2$) for 10 min followed by a 1:50 dilution of the chemiluminescent substrate disodium 3-(4-methoxyspiro{1,2-dioxetane-3,2'-(5'-chloro)tricyclo [3.3.1.1$^{3,7}$]decan}-4-yl)pheryl phosphate (CSPD) (Roche Applied Science) before sealing the membrane in two sheets of transparency film and exposing it to X-ray film for 1.5 hr. A blot containing genomic DNA from *M. incognita, M. javanica, M. arenaria* and *M. hapla* hybridized with a 16D10 cDNA probe showed that 16D10 was present in each of the four agriculturally important *Meloidogyne* species with 3-4 copies or homologues (FIG. 6). No hybridization was detected with genomic DNAs from the soybean cyst nematode *H. glycines*, the non-parasitic free-living nematode *Caenorhabditis elegans*, and plants (tobacco and *Arabidopsis*).

Example 6

Sequence Analyses

Sequence similarity searches were carried out using the BLAST programs PSI-BLASTP and BLASTX at the National Center for Biotechnology information (NCBI) (Altschul et al., 1998). Multiple sequence alignments of *Meloidogyne* 16D10 genomic DNA sequences were generated using ClustalW1.8 (Jeanmougin et al., 1994). Prediction of a signal peptide for secretion and the cleavage site was performed via the SignalP program (Nielsen et al., 1997).

Example 7

In situ Hybridization

Specific forward and reverse primers for 16D10 cDNA clone were used to synthesize digoxigenin (DIG)-labeled sense and antisense cDNA probes (Roche Applied Science, Indianapolis, Ind.) by asymmetric PCR (Huang et al., 2003). In situ hybridization was performed using formalin-fixed, permeabilized pre-parasitic juveniles and mixed parasitic stages of *M. incognita* (De Boer et al., 1998; Huang et al., 2003). cDNA probes that hybridized within the nematode were detected with alkaline phosphatase-conjugated anti-DIG antibody and substrate, and specimens were observed with a compound light microscope (De Boer et al., 1998). In situ mRNA hybridization revealed that 16D10 was strongly expressed in the two subventral esophageal gland cells of *M. incognita* at the early parasitic stages.

Example 8

Immunofluorescence Assay

The purified 16D10 polyclonal antiserum was used to localize 16D10 expression in sections of pre-parasitic J2, mixed parasitic stages of *M. incognita* with indirect immunofluorescence as described previously by Goverse et al. (1994). Following fixation in freshly prepared 2% paraformaldehyde in PBS buffer (80 mM $Na_2HPO_4$, 20 mM $NaH_2PO_4$, 100 mM NaCl, pH7.4) for 5 days at 4° C., the nematodes were washed three times in PBS buffer and once in deionized water. The fixed nematodes were cut into sections and incubated in 0.6 mg of proteinase K (Roche Applied Science, Indianapolis, Ind.) per ml in phosphate buffered saline (PBS) buffer at 37° C. for 1 hr. After washed once with PBS, the partially digested nematodes were placed in a −80° C. freezer for 20 min, incubated in dry-ice cold methanol for 3 min, and then incubated in dry-ice cold acetone for 15 min. The nematodes were washed once with blocking solution (10% goat serum, 0.02% $NaN_3$, 1 mM phenylmethylsulfonyl fluoride, 1×PBS) amended with protease inhibitors as previously described (Goverse et al., 1994), incubated at 4° C. for 3 days and then used immediately for immunofluorescence. The blocked nematodes were aliquoted to wells of a 96-well MultiScreen plate (Millipore, Bedford, Mass.), and agitated in a 1:250 dilution of the 16D10 purified polyclonal antibody in ELISA diluent (0.05% Tween, 0.02% $NaN_3$, 1% BSA, 1×PBS) in a moisture chamber overnight at RT. Nematode sections were washed three times for 5 min each with PBST (1×PBS, 0.5% Triton X-100) and agitated in a 1:1000 dilution of fluorescein isothiocyanate (FITC)-conjugated goat anti-rabbit IgG (Sigma-Aldrich, St. Louis, Mo.) in Tris-Saline-BSA (0.15M NaCl, 0.01M Tris, pH7.2, 0.2% Triton X-100, 3% BSA) in the dark for 3 h at RT. Sections were washed twice in PBST and once with distilled water. Treated sections were transferred in a 15-μl drop of water to individual wells on Multitest slides (ICN-Flow, Horsham, Pa.) that previously coated with 5 μl of 0.1% poly-L-lysine (Sigma Chemical). Sections were airy dried on slides, covered with a 3 μl drop of antiquenching agent (0.02 mg/ml phenylenediamine in 500 mM carbonate buffer, pH8.6, mixed with nonfluorescent glycerol), and a coverslip was applied. Specimens were observed on an Olympus fluorescence microscope. Negative control consisted of pre-immune rabbit serum. The purified 16D10 antiserum bound to secretory granules within the subventral gland cells of pre-parasitic and parasitic J2 and their cytoplasmic extensions and expanded ampullae, which are located posterior to the pump chamber at the metacarpus. No specific labeling with the rabbit preimmune serum was observed in any nematode specimens.

Example 9

Protein Extraction

Nematode proteins were extracted by grinding pre-parasitic J2 and mixed parasitic stages of *M. incognita* and *H. glycines* in 200 μl of extraction buffer [100 mM Tris-HCl, pH7.0, 150 mM NaCl and 1× complete protease inhibitors (Roche Applied Science, Indianapolis, Ind.)] in microcentrifuge tubes in liquid nitrogen. Plant proteins (0.5 g) were extracted by grinding transgenic seedlings or root tissues in 200 μl of extraction buffer [50 mM Tris-HCl, pH7.0, 150 mM NaCl, 1× complete protease inhibitors (Roche Applied Science)] in microcentrifuge tubes in liquid nitrogen. Supernatant was recovered from homogenates after centrifugation at 13,000 rpm for 10 min. All protein concentrations were estimated (with a Bio-Rad Protein Assay Kit II) with BSA as a standard. As the positive control, the 16D10 peptide (GKKPSGPNPGGNN, >95% purity) (SEQ ID NO:52) was synthesized from Sigma-Genosys, TX for immunodetection assays (see examples 12-13).

Example 10

Collection of Stylet Secretions

Stylet secretions from *M. incognita* J2 were produced and collected in vitro as described by Davis et al. (1994). Pre-parasitic J2 were incubated in 0.4% resorcinol (Sigma-Aldrich, St. Louis, Mo.) for 6 hr at room temperature in a humid chamber. Stylet secretions were solubilized via adding an equal volume of 0.1M Tris-NaOH, pH11.0. Solubilized stylet secretions were concentrated with StrataClean (Stratagene, La Jolla, Calif.). Briefly, soluble secretory proteins were trapped via suspending 1.5 ml of beads in the supernatant of induction mixture (460 ml) and incubating it for 1 hr under constant mixing. The beads were centrifuged, re-suspended in 2×SDS-PAGE sample buffer, and boiled for 3 min to release the absorbed proteins. The concentrated stylet secretions were used in enzyme-linked immunosorbent assay (ELISA) and immunoblotting analyses using the purified 16D10 antiserum (see Examples 11-13). Both assays identified 16D10 peptide in the stylet secretions as well as total extracts of J2 and mixed parasitic stages of *M. incognita.*

Example 11

Production of Antisera

Polyclonal antiserum to 16D10 was produced by immunizing two rabbits with a synthetic mature (i.e., without the N-terminal signal peptide) 16D10 peptide (GKKPSGPNPGGNN) (SEQ ID NO:52) from Eurogentec, Inc. (Herstal, Belgium). The antiserum was affinity-purified from 15 ml of last crude sera with the peptide antigen. Peptide affinity-purified 16D10 polyclonal antiserum was used to localize 16D10 expression in specimens of *M. incognita* using immunofluorescence microscopy (Goverse et al, 1994), and for immunodetection of 16D10 in stylet secretions and transgenic plant-expressed or in vitro translated 16D10.

Example 12

Western Dot-blot Analysis

Protein samples (41) were spotted onto Hybond ECL nitrocellulose. The nitrocellulose membrane was allowed to air dry for 20 min. The membrane was incubated in a blocking solution (2% nonfat dry milk, 1× Tris-buffered-saline-Tween [TBS-T: 20 mM Tris-HCl, pH7.4, 0.8% NaCl, 0.1% Tween 20] overnight at 37° C. and then treated with the purified 16D10 polyclonal antiserum (1:2,000), followed by anti-rabbit IgG (whole molecule) alkaline phosphatase conjugate (1:30,000) (Sigma). The membrane was washed three times in 1×TBS-T buffer at room temperature, and incubated in the substrate solution (45 μl of nitroblue tetrazolium [NBT] solution and 35 μl of 5-bromo-4-chloro-3-indolyl-phosphate toluidinium [BCIP] solution in 10 ml of AP buffer [100 mM Tris-HCl, pH9.5, 100 mM NaCl, 5 mM MgCl]) at room temperature until color develops.

Example 13

ELISA Assay

ELISA was modified from Pratt et al. (1986). Dynatech Immulon plate wells were coated overnight at 4° C. with proteins diluted in borate saline (0.2M sodium borate, 75 mM NaCl, pH8.5) from the following sources: 2 µl of 1000× concentrated stylet secretions of *M. incognita* J2, 10 µg of total extracted proteins of pre-J2 of *M. incognita*, MS of *M. incognita*, pre-J2 and MS of *H. glycines*, or 10 µg of BSA (Sigma Chemical) as a negative control. As a positive control, wells were coated with 100 ng of synthetic 16D10 peptide (>95% purity, Sigma-Genosys, TX). Wells were rinsed three times with wash buffers (10 mM Tris.HCl, pH8.0, 0.5M NaCl) and blocked with 1% BSA in PBS (32.9 mM $Na_2HPO_4$, 1.77 mM $NaH_2PO_4$, 0.14M NaCl, pH7.4) for 30 min at room temperature. After being rinsed once with wash buffer, each coated well was incubated with 16D10 purified polyclonal antisera diluted 1:1,000 with 0.5% BSA in PBS for 1 hr at room temperature. Negative controls included omitting incubation with the primary polyclonal antibody, and incubation with the rabbit pre-immune serum. The wells were washed three times, incubated with alkaline phosphatase-conjugated goat anti-rabbit antibody (Sigma Chemical) at 1:5,000 dilution for 1 hr at room temperature, washed three times before phosphate colorimetric substrate was added. The substrate, p-nitrophenyl phosphate was prepared according to manufacturer's directions in alkaline phosphatase buffer (1M diethanolamine, 0.5 mM $MgCl_2$, pH 9.8) and incubated in the treated wells 30 min at room temperature before the reaction was stopped with 3 N NaOH. Absorbance was measured at 405 nm and 490 nm on an ELISA reader.

Example 14

Plasmid Construction

The coding regions of 16D10 with or without a signal peptide sequence were amplified from the full-length cDNA clone with primers 16D10SF (5'-CGGGGTACCTAGATGTTTACTAATTCAATTAA-3') (SEQ ID NO:57) or 16D10F. (5'-CGGGGTACCTA GATGGGCAAAAAGCCTAGTG-3') (SEQ ID NO:58) and 16D10R (5'-GC TCTAGATCAATTATTTCCTCCAGG-3') (SEQ ID NO:59) that introduced KpnI or XbaI restriction sites (underlined) and the stop/start codons (in italics), cloned into the KpnI and XbaI sites of binary vector pBIX under the control of CaMV 35S promoter to generate pBIX(16D10S) and pBIX(16D10), respectively, and confirmed by sequencing. pBIX was derived from pBI101 (BD Biosciences, Palo Alto, Calif.) and contains a nos promoter-nptII-nos terminator cassette, a 355 promoter-gusA-nos terminator, and a second 35S promoter with a polylinker having KpnI and XbaI sites. The hybrid expressed sequence of clv3 and 16D10 was generated by PCR amplifications from *Arabidopsis* genomic DNA using primers C3K (5'-GGGGTACCATGGATTCTAAAAGCTTTG-3') (SEQ ID NO:60) that introduced KpnI restriction site (underlined) and C3R (5'-CCACTAGGCTTTTTGCCAAGGAACAAGAAGCAG-3') (SEQ ID NO:61) for signal sequence, and from 16D10 cDNA using primers C3F (5'-CTTCTGCTTCTTGTTCCTTGGCAAAAAGCCTAGTGG-3') (SEQ ID NO:62) and 16D10X (5'-GCTCTAGATCAATTATTTCCTCCAGG-3') (SEQ ID NO:63) that introduced XbaI restriction site (underlined) for mature peptide coding sequence using Vent polymerase (New England Biolabs, Beverly, Mass.). The two products were then used to prime each other in a fusion PCR reaction. The resulting fragment was cloned into pBIX to generate pBIX(C3S-16D10) and verified by sequencing.

Example 15

Tobacco Hairy-Root Transformation

The plasmids pBIX(16D10), pBIX(16D10S) and the empty vector pBIX as a control were transferred into *Agrobacterium rhizogenes* ATCC 15834 by electroporation (Shen and Forde, 1989) and transformed into tobacco (*Nicotiana tabacum* cv Petite Havana SR1) using the *A. rhyzogenes*-mediated cotyledon transformation (Christey, 1997). Transformed hairy roots were generated from inoculated tobacco cotyledons on Gamborg's B-5 plates containing 0.8% Noble agar with 100 mg/L kanamycin and timentins (230.8 mg/L ticarcillin disodium plus 7.69 mg/L clavulanate potassium). Individual hairy root tips (about 0.5 cm) were cultured for 3 weeks at 24° C. in the dark, and 2 to 3 roots from individual hairy root system were subjected to GUS-staining (Jefferson et al, 1987). The kanamycin-resistant and GUS-positive root lines with no bacterial contamination, confirmed by PCR analyses, were used to establish hairy root lines. The root-tips were sub-cultured for root growth assay on Gamborg's B-5 plates without hormones every 2 weeks and the cut roots were kept in culture on the old plates at 24° C. in the dark for assays. For root-growth assays, plates were cultured horizontally in the dark and 5 hairy roots from each transgenic line in each of the three repeats were investigated. Relative RT-PCR and immunoblotting analyses of transgenic hairy roots or calli with a single transgenic copy identified as described (Does at al, 1991) were carried out using the same procedures as in those of transgenic *Arabidopsis*. Expression of 16D10 in the cytoplasm of hairy root cells increased root growth at the rate of approximately 65% [mean root length after 2 weeks of 5.20±0.61 cm (n=90) in 16D10 transgenic lines, compared to 3.15±0.34 cm (n=90) in control lines], generated extensive lateral roots and led to the formation of calli where roots were cut for subculturing at 5 weeks. RT-PCR analysis of 16D10 expression showed that the steady-state mRNA levels in calli were higher than in the hairy roots. Immunoblotting analysis with the purified 16D10 antiserum revealed that 16D10 was produced in both hairy roots and calli. No expression of 16D10 was detected in the control vector-transformed hairy roots.

Example 16

*Arabidopsis* Floral-Dip Transformation

The plasmids pBIX(16D10), pBIX(C3S-16D10) and the empty vector pBIX as a control were introduced into *Agrobacterium tumefaciens* C58C1 by electroporation (Shen and Forde, 1989) and transformed into *A. thaliana* wild-type Col-0 plants by the floral dip method (Clough and Bent, 1998). Segregation of kanamycin resistance, GUS-straining (Jefferson et al, 1987), and 16D10 expression coupled to PCR analyses confirmed generation of the transgenic homogenous $T_2$ lines. Inverse PCR (Does et al., 1991) identified the homogenous lines with a single transgenic copy in the genome for molecular and root growth assays. Thirty plants from each transgenic line in each of the three repeats were in vitro cultured on MS plates with 3% sucrose with 16 h light (24° C.)/8 h dark (20° C.) cycles and the plates were kept vertically for root growth assay.

Figure 3:
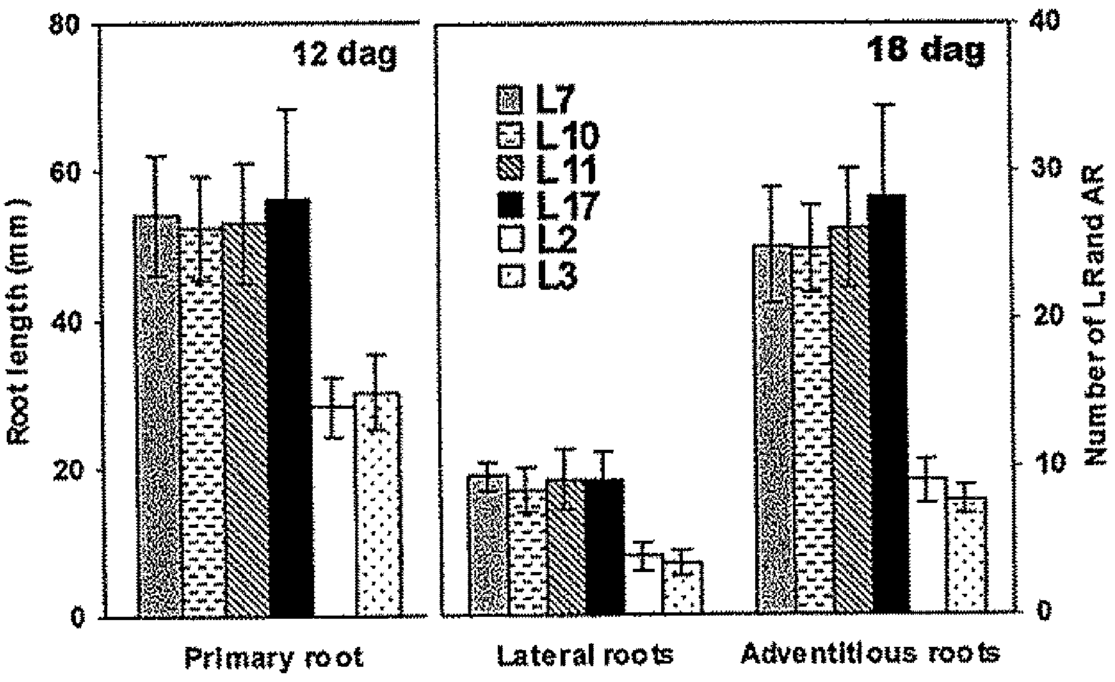
FIG. 3 shows a bar graph indicating enhanced root growth of four transgenic *Arabidopsis* $T_2$ homozygous lines L7, L10, L11, L17 compared to control lines (L2, L3).

Four transgenic *Arabidopsis* $T_2$ homozygous lines containing a single-copy of 16D10 without a signal peptide under the control of the 35S promoter were generated. Two transgenic lines originating from the blank transformation vector were also generated as controls. RT-PCR and immunoblotting analyses confirmed that 16D10 was expressed in all of the 16D10 transgenic lines, but not in the control lines. Compared to controls, expression of 16D10 in the cytoplasm of *Arabidopsis* cells increased the length of primary roots 85% [mean 54.01±8.75 mm in four 16D10 transgenic lines (n=90/line), and 29.20±4.50 mm in 2 control lines (n=90/line)] and the number of lateral branches and adventitious roots increased 1.4-fold and 2.08-fold, respectively (FIG. 2 and FIG. 3). Increased primary root growth was closely correlated with increased lateral root number and increased adventitious root number. Measurements of the root tip growth rate over 3 days revealed an increase (20%) in length only in the meristematic zone of 16D10 roots, indicating increase in cell number and not cell size contributed to the enhanced root growth.

Example 17

Complementation Tests

Since the mature 16D10 peptide of 13 aa (GKKPSGPNPGGNN) (SEQ ID NO:52) contained 8 aa (K-PSGPNP-N) (SEQ ID NO:53) of the conserved C-terminal 13 aa motif (KRLVPSGPNPLHN) (SEQ ID NO:54) of the functional domain of *Arabidopsis* CLV3-like proteins (Cock and McCormick, 2001), the plasmid pBIX(Clv3S-16D10) encoding *M. incognita* 16D10 with *A. thaliana* CLAVATA3 signal peptide was transferred into the *A. thaliana* clv3 mutants clv3-9 (intermediate), clv3-2 and clv3-6 via *A. tumefaciens* C58C1-mediated floral-dip transformation (Clough and Bent, 1998) for functional complementation tests. As controls, the plasmids pBIX(16D10) and pBIX were also introduced into the clv3 mutants. Three transgenic $T_2$ homozygous lines for each construct were also generated. The phenotypes (flower and shoot apical meristem) of 16D10-transformed clv3 lines were investigated and compared with those of vector-transformed lines, *A. thaliana* wild-type ecotype Col-0 and the clv3 mutant progeny as described in Fletcher et al. (1999). While 16D10 contained the functional domain of *Arabidopsis* CLV3-like proteins, expression of 16D10 in the apoplast or cytoplasm of *Arabidopsis* clv3 mutants did not restore wild type phenotype, indicating 16D10 does not function as CLV3-like proteins.

Example 18

Histological Analysis

Primary root tissues of *A. thaliana* were fixed and dehydrated (Dolan et al, 1993), and embedded in Spurrs resin using Low Viscosity Embedding kit (Electron Microscopy Sciences, Hatfield, Pa.) according to the manufacturer's instructions. Thin sections (0.4 μM) were made on a Reichert-Jung Ultracut E and stained with 1% toluidine blue. Transverse root sections in and above the root meristem and longitudinal sections at the root-tip revealed that the average cell-size and number of cell types and cell-layer did not differ in the transgenic lines, compared to wild type. Root morphology was also not altered in our transgenic plants, and increased growth was accompanied by accelerated development of the root system. Thus ectopic 16D10 expression enhanced root growth rate and induced lateral root initiation, possibly by stimulation of cell division in meristems, increasing the rate of cell production without altering meristem organization.

Example 19

Relative RT-PCR

Reverse transcription (RT)-PCR was conducted on mRNA extracted from equivalent amounts of plant tissue. The 16D10 gene-specific primers 16D10F and 16D10R as described above were used in subsequent PCR amplifications. In controls, the primers UBQ1 (5'-GATCTTTGCCGGAAAACAATTGGAGGATGGT-3') (SEQ ID NO:64) and UBQ2 (5'-CGACTTGTCATTAGAAAGAAAGAGATAACAGG-3') (SEQ ID NO:65) designed from the uniformly expressed UBQ10 gene (GenBank accession no. NM_202787) of *A. thaliana* wild-type ecotype Col-0, were used to amplify a 483 bp unique sequence of UBQ10 from transgenic *Arabidopsis* lines. The primers ActF (5'-CCGGTCGTGGTCTTACTGAT-3') (SEQ ID NO:66) and ActR (5'-GCACCGATTGTGATGACTTG-3') (SEQ ID NO:67)-designed from the uniformly expressed actin gene (GenBank accession no. U60494) of *N. tabacum* cv Petite Havana SR1 were used to amplify a 271 bp unique sequence of the tobacco actin (Tob104) gene from transgenic tobacco hairy roots. PCRs containing the following components: 50 of 10×BD Advantage 2 PCR buffer, 1.0 μl of 10 mM dNTP mix, 1.50 of 5' primer, 1.5 μl of 3' primer, 2μl of cDNA, 380 of water, and 1.0 μl of 50×BD Advantage 2 Polymerase Mix (BD Biosciences, Palo Alto, Calif.). PCR cycles consisted of an initial denaturation step at 94° C. for 2 min, followed by 35 cycles of 94° C. for 1 min, 55° C. for 30 seconds, 72° C. for 40 seconds, and a final 10-min elongation step at 72° C. Ten-microliter aliquots of each RT-PCR reaction were electrophoresed on a 2% agarose gel, transferred to nylon membranes, and hybridized with corresponding DIG-labeled DNA probes. RT-PCR analysis revealed that 16D10 transcripts were steadily present in the 16D10 transgenic tobacco hairy roots and *Arabidopsis* lines, but absent in the vector-transformed control lines.

Example 20

Yeast Two-Hybrid Screens

The MATCHMAKER yeast two-hybrid system II (BD Biosciences, Palo Alto, Calif.) was used in the yeast two-hybrid screening. The cDNA encoding the mature peptide of 16D10 was cloned in frame into the GAL4-binding domain (BD) of pGBKT7 to generate pGBKT7(16D10) and expressed as bait to screen a tomato root cDNA library constructed from mRNA from tomato root tissues in the GAL4 activation domain (AD) of pGADT7. Twelve full-length SCL-encoding cDNAs (AtSCL1, AtSCL3, AtSCL5, AtSCL6, AtSCL9, AtSCL13, AtSCL14, AtSCL21, AtSCR, AtSHR, AtRGA, AtGAI) were amplified from a root cDNA pool made from mRNA from *A. thaliana* root tissues with specific primers of each gene based on the corresponding sequences in GenBank databases (Bolle, 2004), and cloned in frame into pGADT7. Each of the constructs was introduced with pGBKT7(16D10) into the yeast strain AH109. cDNAs encoding the specific regions of AtSCL6 and AtSCL21 were cloned into pGADT7, and then co-transformed with pGBKT7(16D10) into the strain AH109. All procedures including cDNA library screening, selection of positive clones and the assay of (3-galactosidase activity, were performed by following the protocol of MATCHMAKER yeast two-hybrid system II (BD Biosciences, Palo Alto, Calif.). Two *Arabidopsis* SCL proteins, AtSCL6 and AtSCL21, interacted with 16D10 in yeast. Domain analysis revealed the specific interaction of 16D10 with the SAW domain of AtSCL6 and AtSCL21, and no interaction of 16D10 with the rest of the domains of the SCL proteins, and indicated that the SCL transcription factor(s) was a putative target of the secreted 16D10 during RKN parasitism of plants.

Example 21

RNAi by Soaking

Forty-two by and 271 bp sequences of 16D10 were respectively amplified from the full-length cDNA clone using the primers 16D10T7F1 (5'-TAATACGACTCACTATAGGGCCTCAAAAATACCATAAAG-3') (SEQ ID NO:68) and 16D10T7R1 (5'-TAATACGACTCACTATAGGGGAAATTAACAAAGGAAACC-3') (SEQ ID NO:69), and 16D10T7F2 (5'-TAATACGACTCACTATAGGGGGCAAAAAGCCTAGTGGGC-3') (SEQ ID NO:70) and 16D10T7R2 (5'-TAATACGACTCACTATAGGGTCAATTATTTCCTCCAGG-3') (SEQ ID NO:71) each of that incorporates the RNA primer site T7 (underlined). The gel-purified PCR products were used as templates for synthesis of sense and antisense 16D10 RNAs in a single reaction in vitro using the MEGAscript RNAi kit (Ambion, Austin, Tex.) according to manufacturer's instructions, except that the reactions were incubated for 16 hr to increase RNA yield. The amount and quality of generated double-strand (ds) RNA were estimated and quantitated by standard procedures (Sambrook et al., 1989). The dsRNA products were ethanol precipitated and re-suspended in nuclease-free water to 10-15 μg/μl.

Figure 4:
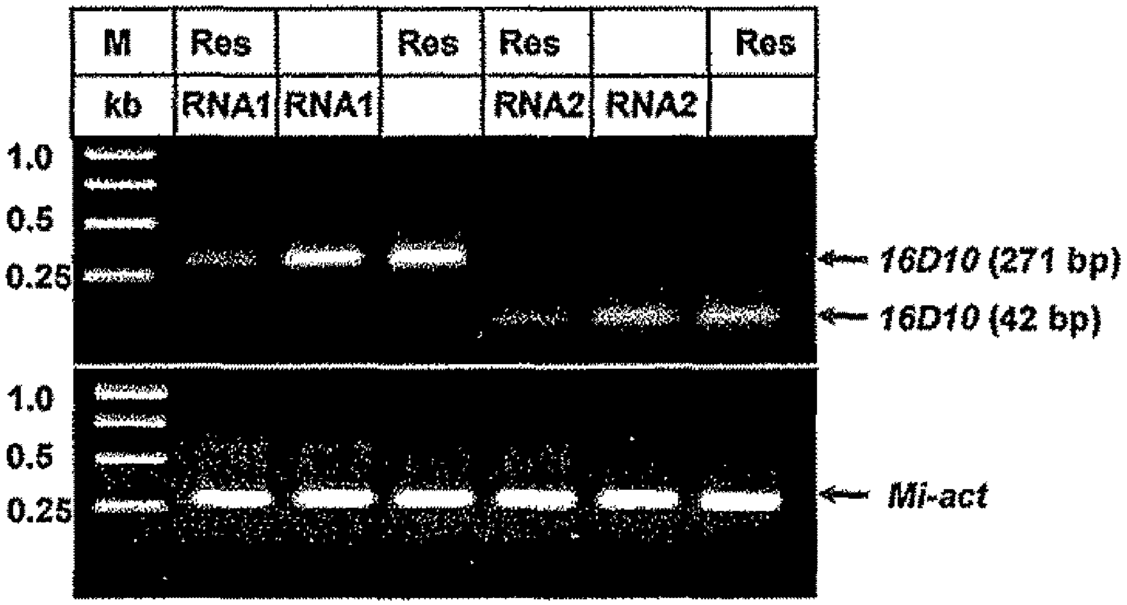
FIG. 4 shows RT-PCR analysis of 16D10 dsRNA (RNA1 and RNA2) treated second-stage juveniles of root-knot nematode showing a significant reduction of transcripts of parasitism gene 16D10 in the treated nematodes. Resorcinol (Res) was used to help stimulate uptake of the dsRNA. No reduction of transcripts with dsRNA or res alone. Mi-act—internal transcript control.

Approximately 10,000 freshly hatched J2s of *M. incognita* were soaked in ¼ M9 buffer (10.9 mM $Na_2HPO_4$, 5 mM $KH_2PO_4$, 4.7 mM $NH_4Cl$, and 2.2 mM NaCl) containing 1 mg/ml of 16D10 dsRNA, 1% resorcinol, 0.13 mg/ml FITC isomer I, 0.05% gelatin and 3 mM spermidine, and incubated for 4 hr in the dark at RT on a rotator. Resorcinol (Res) was used to help stimulate uptake of the dsRNA. Control samples were incubated in the same solution but without resorcinol or dsRNA. After soaking, nematodes were thoroughly washed five times with nuclease-free water by centrifugation and about 100% of treated nematodes were observed with an Olympus fluorescence microscope to take up FITC, a marker for uptake of dsRNA. The FITC-labeled transgenic J2 were assayed to determine silencing of the 16D10 transcripts by relative RT-PCR analysis, using first-strand cDNAs synthesized from mRNA of equivalent number of treated J2 as templates and a 284 bp amplified fragment of the *M. incognita* constitutively expressed actin gene (GenBank accession no. BE225475) as a control. The ingestion of short or full-length 16D10 dsRNA by second-stage juveniles of root-knot nematode caused a significant reduction of 16D10 transcripts in the treated nematodes (FIG. 4), providing direct evidence for in vivo targeting of 16D10 in root-knot nematodes by RNAi.

Figure 5:
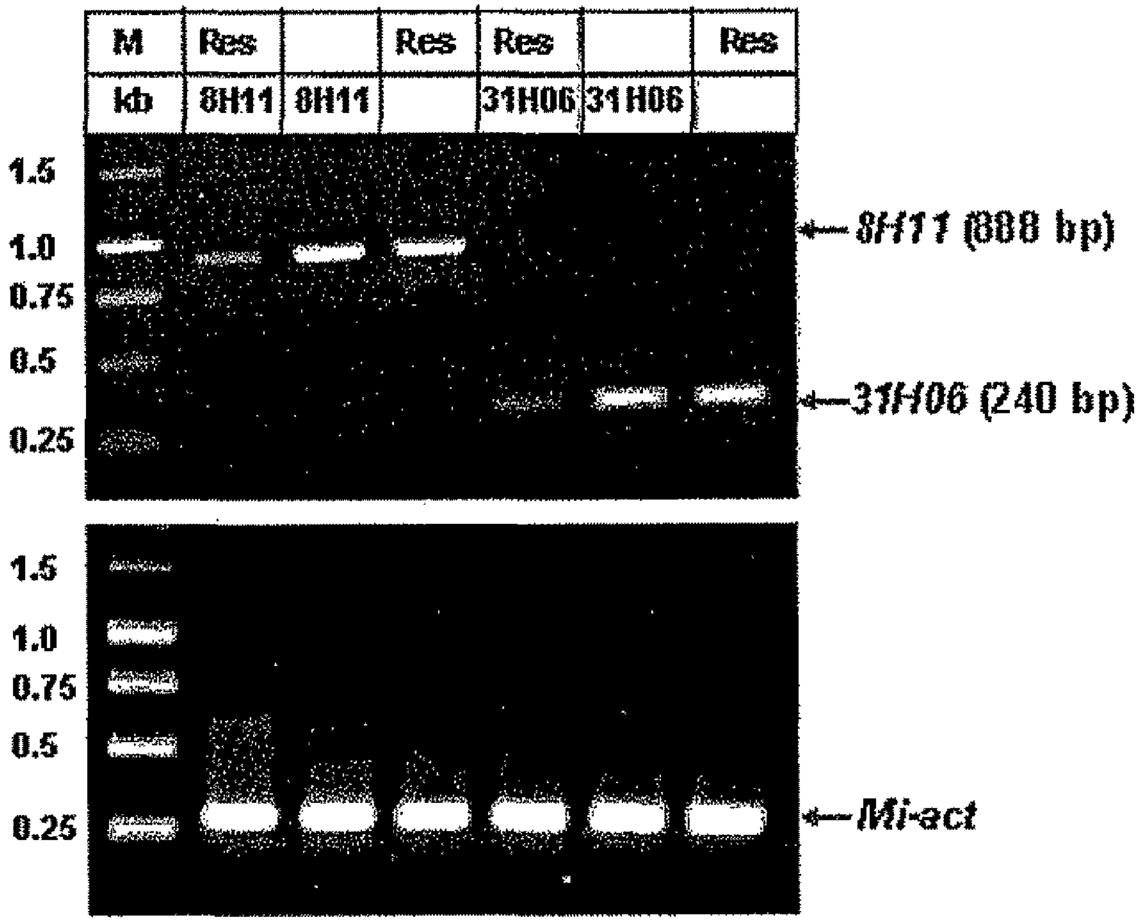
FIG. 5 shows a photograph of a gel indicating that RNAi directed to 8H11 or 31H06 down-regulates expression of parasitism genes 8H11 or 31H06 in nematodes.

J2s of *M. incognita* were also soaked as described above with 1 mg/ml of dsRNA specific for 8H11 (SEQ ID NO:17) or 31H06 (SEQ ID NO:33). Relative RT-PCR analysis revealed that ingestion of 8H11 and 31H06 dsRNA by second-stage juveniles of root-knot nematode caused a significant reduction of transcripts of these two additional parasitism genes in the treated nematodes (FIG. 5).

Example 22

In Planta Delivery of RNAi

The sense and anti-sense cDNAs (42 bp or 271 bp) of 16D10 were amplified from the full-length cDNA clone with the gene-specific primers 16D10Xho1 (5'-CCG CTCGAGGGCAAAAAGCCTAGTGGGC-3') (SEQ ID NO:72) and 16D101<pn1 (5'-CGG GGTACCTCAATTATTTCCTCCAGG-3) (SEQ ID NO:73), 16D10Cla1 (5'-CC ATCGATTCAATTATTTCCTCCAGG-3') (SEQ ID NO:74) and 16D10Xba1 (5'-GC TCTAGAGGCAAAAAGCCTAGTGGGC-3') (SEQ ID NO:75), 16D10Xho3 (5'-CCG CTCGAGCCTCAAAAATACCATAAAG-3'(SEQ ID NO:76) and 16D10 Kpn2 (5'-CGG GGTACCGAAATTAACAAAGGAAACC-3') (SEQ ID NO:77), 16D10Cla2 (5'-CC ATCGATGAAATTAACAAAGGAAACC-3') (SEQ ID NO:78) and 16D10Xba3 (5'GC TCTAGACCTCAAAAATACCATAAAG-3') (SEQ ID NO:79) that introduced XhoI, KpnI, ClaI or XbaI restriction sites (underlined), respectively. The PCR products were gel-purified, and digested with the restriction enzymes XhoI and KpnI, or ClaI and XbaI, respectively. The digested-PCR products were cloned into the Xho-KpnI sites, and the ClaI-XbaI sites of pHANNIBAL to generate pHANNIBAL(16D10#1) and pHANNIBAL(16D10#2), respectively. The sense and antisense 16D10 cDNAs of pHANNIBAL-derived plasmids were subcloned as NotI fragments into the binary vector pART27 (Gleave, 1992) to produce highly effective intron-containing "hairpin" RNA (ihpRNA) silencing constructs (Wesley et al., 2001). The pART27-derived constructs were electroporation transformed into *A. tumefaciens* C58C1. The transformants were selected on LB media containing rifampicin (50 mg/L), gentamycin (25 mg/L) and spectinomycin (100 mg/L), and then introduced into *A. thaliana* ecotype Col-0 via floral-dip transformation as described above. Transgenic homologous T2 lines constitutively transcribing the specific ihpRNA of 16D10 under the CaMV35S promoter were generated for resistance assays to the root-knot nematodes, *Meloidogyne* species.

Example 23

Resistance Assays

Figure 7:
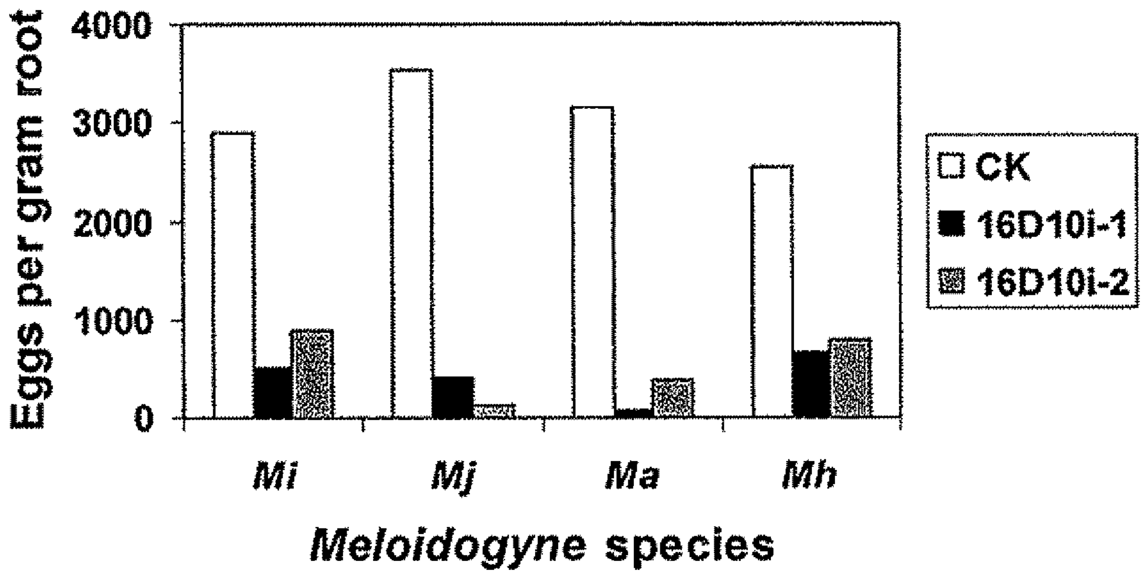
FIG. 7 shows a bar graph indicating reproduction (eggs per gram root) of four *Meloidogyne* species (Mi, *M. incognita*; Mj, *M. javanica*; Ma, *M. arenaria*; Mh, *M. hapla*) on transgenic *A. thaliana* expressing 16D10 dsRNA was decreased compared with control plants.

Seeds from the *A. thaliana* transgenic lines generated from transformation of pART27-derived constructs were surface sterilized in 70% (v/v) ethanol for 1 min and 3% (v/v) sodium hypochloride for 5 min, and then rinsed 5 times in sterile distilled water. The sterilized seeds were geminated and grown on Gamborg's B-5 medium for 3 weeks. *M. incognita* eggs were sterilized and then inoculated about 500 eggs for each plant near to the roots as described (Sijmons et al., 1991). The number and size of galls on the infected roots were analyzed after inoculation of 3 weeks, and the infected roots were stained red with acid fuschin as described (Hwang et al., 2000) and assayed by the number of eggs per gram of roots after inoculation of 8 weeks. Transgenic *Arabidopsis* lines expressing 16D10 dsRNA were resistant to the four major *Meloidogyne* species—*M. incognita, M. javanica, M. arenaria*, and *M. hapla*. Root galling assay showed a 63-90% reduction in the number (and size) of galls on the 16D10 dsRNA transgenic *Arabidopsis* lines, compared to galls on the vector-transformed line (FIGS. 1A, 1B and Table 1). Nematode reproduction assay revealed a 70-97% reduction in the number of RKN eggs per gram root in the 16D10 dsRNA transgenic lines when compared to the control plants (FIG. 7).

TABLE 1

Gall production on transgenic *A. thaliana* expressing 16D10 dsRNA and inoculated with four Meloidogyne species (*M. incognita*, *M. javanica*, *M. arenaria*, *M. hapla*) compared with control plants.

| Galling No. | CK | | | | 16D10i-1 | | | | 16D10i-2 | | | |
|---|---|---|---|---|---|---|---|---|---|---|---|---|
| (Mean value) | T | L | M | S | T | L | M | S | T | L | M | S |
| *M. incognita* | 13.50 | 4.83 | 7.67 | 1.00 | 1.50 | 0 | 0.25 | 1.25 | 3.40 | 0 | 0.80 | 2.60 |
| *M. javanica* | 14.38 | 7.41 | 5.47 | 1.50 | 3.29 | 0.14 | 1.00 | 2.15 | 2.50 | 0.13 | 1.25 | 1.12 |
| *M. araneria* | 11.75 | 6.75 | 3.25 | 1.75 | 3.00 | 0.17 | 1.50 | 1.33 | 3.50 | 0.25 | 0.75 | 2.50 |
| *M. hapla* | 10.21 | 3.46 | 6.25 | 0.50 | 3.63 | 0.25 | 2.33 | 1.05 | 3.78 | 0.50 | 1.67 | 1.61 |

T: total
L: large (>2 mm)
M: medium (1-2 mm)
S: small (<1 mm)
n: 8-16

Example 24

16d10 Sequence Data

16D10 Genomic DNA sequence (840bp)

(SEQ ID NO: 1)

GAGAAAATAAAATATAAATTATTCCTCAAAAATACCATAAAGGTTAGC

CAATATTAATTCTTTTGAAATTTTCTTTGCTTCCATAAATTAAAAAAA

ATTGTTTTTAAGTGAGGGAATGTGGATTAAGCATCTTTCTTATTTTTA

AAATTTTTGATAGAGTGTAGCGACAGTCAATCAAAATATTTTGATTTT

TTTAAAGTTAAAAATTAAGGATGATAAAGAAGTTTAAAATGTAGGTGG

AAATATAAGTATACCGAAAAACATCTTTTATTTTTAAGTTTAAACAAG

CAGTAAAACTTTGTCTGGTTTTATCACCGGGCAACTGTAAGGGAAGCT

TTAATAAAAATTTTGTAAGATACGAAAATCATTGTCCCCAGTAGCTTG

AGTGATCGAAGCGCCTGGTTGCCATTAAGTTTTTTGCTTGAGACTTAT

ATAACAAGTATATATCAAACCGGATTATAAAGTTAAAGAACAGAAAAA

ATTTCACGGAATAAATATTGGCTAACCACTCAATTTATTTAATTATTC

TTCAATCAAAAAATGTTTACTAATTCAATTAAAAATTTAATTATTTA

TTTAATGCCTTTAATGGTTACTTTAATGCTTTTGTCTGTCTCATTTG

TGGATGCAGGCAAAAAGCCTAGTGGGCCAAATCCTGGAGGAAATAAT

TGAAGAAAAATGATTGAAGAAAAACGTTTAAATTAAACGATAAATGG

GAAATAATGGAATTTAAATTAAGCTAATTTTGATGGTTTCCTTTGTT

AATTTCAACATAAAATTAATTGAATTTACTGAATAAAATTATATCTG

AAAAAAA (One 476-bp intron sequence is bolded).

16D10 cDNA sequence (364bp)

(SEQ ID NO: 2)

GAGAAAATAAAATATAAATTATTCCTCAAAAATACCATAAAGTTAAT

TATTCTTCAATCAAAAAAATGTTTACTAATTCAATTAAAAATTTAAT

TATTTATTTAATGCCTTTAATGGTTACTTTAATGCTTTTGTCTGTCT

CATTTGTGGATGCAGGCAAAAAGCCTAGTGGGCCAAATCCTGGAGGA

AATAATTGAAGAAAAATGATTGAAGAAAAACGTTTAAATTAAACGAT

AAATGGGAAATAATGGAATTTAAATTAAGCTAATTTTGATGGTTTCC

-continued

TTTGTTAATTTCAACATAAAATTAATTGAATTTACTGAATAAAATTA

TATCTGAAAAAAAAAAAAAAAAAAAAAAAAAAAAA

16D10 cDNA sequence region used for making 16D10 RNAi constructs (SEQ ID NO: 2)

GAGAAAATAAAATATAAATTATTCCTCAAAAATACCATAAAGTTAATT

ATTCTTCAATCAAAAAAATGTTTACTAATTCAATTAAAAATTTAATTA

TTTATTTAATGCCTTTAATGGTTACTTTAATGCTTTTGTCTGTCTCAT

TTGTGGATGCAGGCAAAAAGCCTAGTGGGCCAAATCCTGGAGGAAATA

**AT*TGAAGAAAAA***TGATTGAAGAAAAACGTTTAAATTAAACGATAAATG

GGAAATAATGGAATTTAAATTAAGCTAATTTTGATGGTTTCCTTTGTT

AATTTCAACATAAAATTAATTGAATTTACTGAATAAAATTATATCTGA

AAAAAAAAAAAAAAAAAAAAAAAAAAAA

[The bold 42-bp sequence was used for constructing pHANNIBAL(16D10#1), and the underlined 271-bp sequence was used for constructing pHANNIBAL (16D10#2)]

pHANNIBAL(16D10#1):

(a) Construct: (XhoI+42 bp 16D10 sense-strand-sequence+KpnI=54 bp)+Pdk intron+(ClaI+42 bp 16D10 anti-sense-strand-sequence+XbaI=54 bp)

SEQ ID NO: 3)

```
XhoI
CTCGAGGGCAAAAAGCCTAGTGGGCCAAATCCTGGAGGAAATAATTGAGGTACC--------
----                                              KpnI
----------Pdk intron--------------------------------------------
----

ClaI
ATCGATTCAATTATTTCCTCCAGGATTTGGCCCACTAGGCTTTTTGCCTCTAGA
                                                  XbaI
```

(b) PCR detection: primers H1F1 & H1R1 (234 bp PCR product)

Primers H1F2 & H1R2 (273 bp PCR product)

pHANNIBAL(16D10#2)

(1). Construct #2: (XhoI+271 bp 16D10 sense-strand-sequence+KpnI=283 bp)+Pdk intron+(ClaI+271 bp 16D10 antisense-strand-sequence+XbaI=283 bp)

(SEQ ID NO: 4)

```
XhoI
CTCGAGCCTCAAAAATACCATAAAGTTAATTATTCTTCAATCAAAAAAA

TGTTTACTAATTCAATTAAAAATTTAATTATTTATTTAATGCCTTTAATGG

TTACTTTAATGCTTTTGTCTGTCTCATTTGTGGATGCAGGCAAAAAGCCT

AGTGGGCCAAATCCTGGAGGAAATAATTGAAGAAAAATGATTGAAGAA

AAACGTTTAAATTAAACGATAAATGGGAAATAATGGAATTTAAATTAAG

CTAATTTTGATGGTTTCCTTTGTTAATTTCGGTACC
                       KpnI-----------Pdk intron------
----

ClaI
ATCGATGAAATTAACAAAGGAAACCATCAAAATTAGCTTAATTTAAATT

CCATTATTTCCCATTTATCGTTTAATTTAAACGTTTTTCTTCAATCATTTTT

CTTCAATTATTTCCTCCAGGATTTGGCCCACTAGGCTTTTTGCCTGCATC

CACAAATGAGACAGACAAAAGCATTAAAGTAACCATTAAAGGCATTAA

ATAAATAATTAAATTTTTAATTGAATTAGTAAACATTTTTTTGATTGAAGA

ATAATTAACTTTATGGTATTTTTGAGGTCTAGA
                               Xal
```

| TABLE 2 |
|---|
| >2E07>msp1>>bankit482031>>>AF531160 (SEQ ID NO: 5) |
| GATCAAACAATCTCCTCAACAACTAAAAAAACTCAAAAAACACCCCAAAA |
| CCAAACTAAAAAATCAAAAATGTCCATCTTCCTCACTTCTGCTCTTCTAA |
| TCATTTCATTAATCGCTATGACCGAGGGAGCAGGCGATCGAAGCGCTTCA |
| ACCTCTACTGGTTGTACAACCTATTTTGGAATGCTAGATCATGCGGATAC |
| CAAGGAAAATAACAAAAGAAAAACTTTCAAACCCAACGATAAAACCATAT |
| CCAACACTTTGCAAGTGATTGGTGGGACAAAGTTCAGCAATACCTCGGTG |
| GCGTTGGTTGTCGGTGATGAGGTGTTATGTATGGCTAAGACAGGAGGTTC |
| AGGCGATTGCGGAATGCGCTACGATGCGTTGACTGGATCAATGAAATTTA |
| TCATTTCTGATAATATTATTGTTGAGGTTCCATTTGAAGGCGTTTTTTTC |
| TTCACCGACAACAAGTGTGTCATCCAGCTTGTAGGCTACGATATTAAAAC |
| TAATATAACTCTTCTCAAAATTAATGATGTCGACTTCAAAATTGTCCCTA |
| CTGATAAGAAAATTTCCCCGAAGGCTTGTACTATGAAAATGTGAGGGAAA |
| AAAGTAAAGAAAATGTGTAAATATGGAAGGATAAAAACTAAACAAAAAAG |
| AATGTGAAGTAAGAAAAAAAAAAAAAAAAAAAAAAAAAAAAAAA |
| >2G02>msp2>>bankit478474>>>AF531161 (SEQ ID NO: 6) |
| GGATTTAAAAAATTAATTTAAAAAAAGTGAAAAATTCAATTAAAATTAAA |
| AAATATTTTTCAATGAATTTATTTTCTATTTTTTTATTTTTATTTCCAAT |
| CGGGTTTATTTGGGCTGAATGTAGCGGAGATTGTTCTATAGAGAACCAAT |
| ATAATTATAAATGTGAGGATAGAAGTGAATTTTGTGAAGAATGGGGAAAA |
| TACTGCGAAAATGTCTTTCTTCACAAATGTGTAAGAAAGGCTTGTCCAAA |
| GAAATGTAAAGTTTGTCATAGTTCTGGTGAAGAACCTAAACCAAATCCTA |
| CAACTATAACAACGGCATCAACAATAACAACACCATTAGCAACAACACCT |
| CAAAACTCAGCAGTTACTTCGGCAACCTCAAAAAGTGCTACTCCATCAAA |
| AACTTATTCAACCGAGACAACCGAATGTGCTAACACAACTACTGAGGAAT |

TABLE 2-continued

ATGAAGCAACTATTGAGGAATATCAAACAACTACAGAAGAATATGAAGAG
GTAACAACCCCTATAATTACAACCACCAATCCAACAACTTATTTATTAAT
GACTACAATAGTTGAAGAAATTAGTGACGACGAATTCAAAGACGCAAAGA
AGATGAAATGTAAATCATGTAATGCAAAAAGGAAGAAATTGGCTGAAATT
TATGACAAATATTATCCGAAAGTTAAGATTCATGCTAAATTGTAAATTAT
GATGGAAAATGTTTTTGAATTGTGAAAATAAAAATTTAATTAACCCAAAA
AAAAAAAAAAAAAAAAAAAAAAAAA

>2G10>msp27>>bankit482965>>>AY135363
(SEQ ID NO: 7)

GATAGCACAGATCTATTTTTAGATTTTTTTAGCTTTTTAGAAAATTTTAA
TTTAAAAATTATGTTTATTCTTCCAAAACCTTTTTATCTTTTAATTTTAC
TAATTATTTCAACAATTTTCCTTTTATTTTTAATTCTTCGTTTGCCTTCA
ATTTCTTACCAAACAAATCAATGTCAACATTTATGGGACTCTTCCGAGTG
CAAAAATTTAAATAATTCTTTAAATTGGCATCCAATAACTTGTTTTATTG
ACGGAAAGCAAAAAAGAGTTCCCTGTCTTCAACAAAATGATTTAAAAGAA
GTTTATCTTCCATTCAATTCATTTTTGAAAAAACAATTTGATTTGTATGG
AGAGACTGACAAAAGCATTTTTTTAATTTTAAAATTTATTTTTAACAAAA
TTTGCGGACAGATAAAATTTGTCCGCAAAATATTTGCGGACAAATAATTT
TTTTTGTTGTTAGGCTTTTTTAGGGTATTTTTTTCTACAATTTTTTGGAG
TTTTTTTCTACAATTTTTTGGAGTTAATTCTAAATTATAATTTTATTATA
TATTTTATAATTTTAAAATTTTTTTCTTTTTAAGAAAACAATTCTTTTGA
TTATTTTACTTCAAACATTCCTCCACGTCTTTTTAAAAATAAAAATAAAA
TGGTGGCTGCAAATCCAATTGAACAATTTAGCAATGTGGCTATTCGTCAA
AGAATAAAATGTTTAAAACCTGAAAATGGATTACCAATGAGCGTTCAATG
GAGTCCAATTCCCTACTTCTATCCTGTTCAAATACTCCAATTTGGCTTTG
ATTATTTTATGAGAAATCGAACAGAACAGAGGAAATTAATTGAAAGAAGG
TTATCAAACAAAGATGATTTCTTGGTACTAAAAAGTGGAGAGAAAGTTAG
CGAATTTTCAACTTTTTTCTGATTTGCCATTTTACCTTTTCTGCAAAATT
GAATCAATGGATGCTTCCTTGTAATATTTTTGAGAAGATTGGGGGAATT

>4D01>msp3>>bankit478504>>>AF531162
(SEQ ID NO: 8)

GACAATAAACGATCCAATTTCCTAAAATTTTTTAAAAATTTTTAAAATTT
ATTTTATGCCCCTTTTTGTTTATTTAAACAAATTTGCTTGATTATTAATG
CCAAAATTAATTTTATTATTTTATTTAATTATTTATGGAATTTTATTGTT
AATAAGTTTAAGTGAAGCATTTGGGTTTGGTGGAGGATGTGGATGCCCTT
GTATGCCGCAACCATGTATTCCACAACCACCTCCAATTGCTTTACCTTCT
CTATGTTTCCCTCAAATCCAATTGCCCTGTCCCCCTCCATCTTGTGGATG
TTGTGGTAGAAGAAAAAGAGAAAGTGGAGCTTCAGCATTATTAACAGCAG
TTTCAACAAAGTCGGGAATTAAAAGAATTGGAGAAGAAAAAAATCATTGT
AATAATCCACACATTAAAAGAATTATTTTAAAGAATTTAATTATTGGAGA
TTGGGTTGGTACAAGAAATGCAATATATTCAGAATTAAGAGCTAAATTAG
GGGGGAATTATATAATTAATTGTGCTCATGCCCCCTCATTTGCGTATTCT

GGTGATTCTGTGATTGATTATTGTGTGGATGGACATCAGGCAATAACTTG
TGCAGTCTTCAAAATTCAATGAGAATAAAATCAGAATGAATTCTATTTTT
TTAATAAATATAAAAATTTTTATAATATATTTTGAGCATTATAAATATTT
ATAAATTAGTTTTTTTTGATAAATTAATTTGAAAATGTATAAATTAGTTT
TTACTCAAAAAAAAAAAAAAAAAAAAAAAAAAAAAA

>4D03>msp28>>bankit479214>>>AY135364
(SEQ ID NO: 9)

GACGCAATTCCATTTTGCGTTCAATCAATTTAGAAAAAGGCTGGAAATAA
TGATTCATCAACAACTTTATTATTAGCGCTTAGTGTTCCGGGCTTTCATT
TCAACAGAGAAATTTCAAATTCACCTATTTGGAGCTTGGATCAGTTCTTC
TATCGACTTGTAGTCCTAACCTATACTAAAAATTTTTTAAATTAACCACA
ATGGAACTTGCTATTAACAGTCGATTGTTATCATTTTTGTCTTTATTCCT
ATTCATATTTCCTTTAAATGTTGTTGCTCAACGGCATCGTTACCCACACA
ATCAAGGAAATTATTTCAGCAGACAAAAGCTGCAAGAAATACAGAAGGAG
GAAAATGAGGCTGAAAATTCTTTACCAAAAATCTTTTGCGCGCATGGAGC
TTCAGTAGCCGGCCGTTGCGTATGTGATCATGGTTGGGCCGGTACTAATT
GCCAGCGGGAAATGCATTGTGCTACTTTTGAGCGAAATGCTAATGGAAGC
TGCCCAGTCTGTCAGCCCAATTTTCAAGGGGATAAGTGCGAATATATTGA
ATGCCAAAATGGAGGCCAAGAATCATTGGAAACTCAGAATTGTAACTGCC
CAAAGCCTTATTCTGGCCGTTTTTGTGATGAATTACTCACAGGAAATGTC
TACTACTACTATAACTCTAAAGTAGCAACCCCTTGGTCCTCTTGGACTTAT
TTCTGTTATACCAATGATTTGTCTTTATGTTTTATGTGAAAAGATTTGCA
AGGAAAAGACAAGTGAGACGGATTGAGAAAACTTGGAATTTACAGAGCAG
TAAAACTGTGAATCCTGCTCATATTGAATTTCTATTAAGGGAAAAAAAAA
AAAAAAAAAAAAA

>5G05>msp26>>bankit478498>>>AY135362
(SEQ ID NO: 10)

GACCTTAATCAATAAAAAATATTTTTTACATAAAAATGTTTTATTTATTT
TATTTTAAATTATTTTTATTTTCCTTAATTTCTTTAAATAAAGTTAATGG
ATTTTGTATGAAGACTATTTGTTCTGCGGACACCGATTCTCGACACCCTG
TAAATCGAGTAATCGGTATTGGTTCTGATGGAATTAGTGGGGAATATAAA
GCTTTGAGACGAAATGATCAAATTGTTGAAGCTGTAGATTTAAGTTGTAG
AGAAGGAAGTTTTGTTTATTCTCCCTTTGAAGGGGAAATTTCTGCTTGGA
GACCTTTTGATGGAAATGGGCAAGATGAAATTAGAACGGATGAAAATAAG
AAGAATACAGATGGATGCAGACCTGACCGAGGAGTTAGAATTGATGGAAA
AGGACAATGGCAGGGATATCACGTCCTTATTGGCTCTGTTCGTTTATTCC
GTTACAGTGGACATGTTAATGCTGGACAAAAAATTGGTGTATCTTTGGAT
ATTGAATGTGAATTGAAATTAAATAAACAAAAGATGAATAAACGTCCTCG
AAAAGAAGAAAATTTTGTCAGAGTTTATTTACACAAGGAAGGACGTCCAA
TTGATCCAACACATCATTTAATTGATTGTATGTGTATAAACCAAGTCTGT
GAGACAAACAGAATTAATGCTTTGGAAGGACCGTTATTTAAATTTGACAG
TCGTTTTAACGGTGTTAGAGGATGGGAAATTAAATGTCCAGATATTCAAC

TABLE 2-continued

AAATTGAAGAAGAAAATTCTTCAGAAGAAGAGGAAGAAAAGAAAAAAGAA
GAAAATAATTTAAATGAAGAATGGGGAACTCCAAAATTTATTCACCTATA
GAAGGGGAATTGGTTGGAAGAATTAGAGTTAATAGTGAACCTGGGGCACA
GACTTATACTGGATGTACTAATGAAGGAATATTTATGGTTGGGGCTGGAA
AGTGGAATGATTATGAAGTTCGAATTT

>6F06>msp4>>bankit482257>>>AF531163 (SEQ ID NO: 11)

GTTCATTTAAAAATTTTTTCCTAAAAAACTTCAAAAAAGCAACTTTTATT
GCGTAAATGAAAGAAAATCTGTTTAAAAAGAGCCTTATAGGCCTATTTTT
GTTGTTAGCATTCAATTTTACTGAAGCTAAGGACTCTGGAGAGAATACTA
GTCTTGAAGCTAGTTTGAAACCAACTAAAAGTATTGAAAATGCTTCCCTA
GAAGAAAAGAATCAAAAAGAAGAAAATGGAGTAACATTCCCGGCAGAAGG
TCATGAAATTGTCGAAACAAAAAAAGAAATCAACTCACCAGAAGAGGTGA
CAGATTCAACTAAAGGACAGGAAAATTCCGAGGATCGTAAAGTGACAATG
AATGGTGATGAGTCTGAGGCCGATAAATTAAACAATGAAAATGTTGAGGG
TGAAGAAAAGAAAGCAACTGAAAACAAGAATGAAGTTGAGGAAAAAGAAG
TTTTAGAGGATGAGAAGACAAAAGAAGAGGAAGATAAAATTAGCGATGAG
CCTGTGAAGACAAAGGAAATGAAATCAACAAACAATGATAAGGAAGTTGA
AGATTTGAAAGAAGAGGAAGAGAAAGTCGAGGTAAAAGGTAACAAGGATG
AAGAAGAAAATAAGGAAGAGAAGAAGGAAGATAAGAAGACAAAGGATGAA
AAAAAGGTTCCAGAGGTTATTGAGGGAGAGAAGAAAACACCCAAGGAAAA
GGAACACAAAAGCCATTGGTTTATGGACAAATTTAAACATGCTTTCTGTT
TCATAACTCATTACTTCTTTTGTCCATCTAACTCTGCAGAAAAAGGCAAA
GAATCCCATCATGAAGGAAAAGAATCACACCGTGGAAAGCGTCTTAACTC
TGATTTTAGTTCTTTAAGCAGTGATGAGGAAATGATTGAGAATTTTGAAA
ATGCCCACGAATTTAGTGAAGAAATTGAAGAAAATGGGGAATTTAAAGCT
AAAATGAATGTTGGTGCAACATACTTCAAAGCTGAGACAGATAATTCTGG
AAAGATGCGCGGCAAAATTGAAAAAATTTAATGCTGAAATGCATAATTGAA
AAGATTGTAAGGATGGTGGGTGTGCTGATGAGTAAAACAAAAAAAAGCAA
TCCGATTTTATTCTAAATTTTATTTTTTAAAGTGATTCCAACAAGTGATT
CCATTAACCCCTCAAATTTATTTAAAAAAACGAAATTTTAAAAGTTCTGG
ATTTATGTCCCAAAAATTGTACAAATTATTCAAACAAACTCAATGGTTTT
GGACATTATATTTTTTTATTATTTTCTAACAATTTTTATTAATGTTGAAG
TAAAAGATTAATTCAAAAAAAAAAAAAAAAAAAAAAAAA

>6G07>msp5>>bankit482261>>>AF531164 (SEQ ID NO: 12)

ATTCTTAATTTATTTAAAGAATTTATTCTGCATGATGAAATTAATTAATA
TTTTATTTTTATTTTTTGTTATTTTACTGAATTCTATGGCTTTCGGAAGG
TTTTCTTTATTTTTGGAAAAATCAAAATTTCAATTGAATATTTTGTTTTC
ATTCCAAGATTTTCTCACACAGATCCCGCTTAGTGTGAGATATCGGATAA
AGCTTCATAACCTCTACAATTTTAAGATATCCACATTACTCCGTCCAAAT
TCCCTTATATCTCCTTTGATCCCTACAAATCTACCGATATCCCCTCCACC
GATATTTTCCTTTTCCGAACCTTAACTTCCGATCAATCCGCTATCTGGAC
AAATCGTTATTCCTCTAAACAAGAATTTATGCTTTTAAATGTATAAAACC
AATCTTTAATATTCTTCAAAAAAATTTTCAGTCCTTCTCTCAATTCAGTG
CGTGCTAAACGTCAAGGCTGGGGAGGATGGGGTTGGAACCCTCAAGTTCA
AACAGATATTGATCGTCTTCGTATTGATAAAGACAAACTGCGATTAGATA
TGGACCGTTTAAGACTAGATCAGGATAGCTCTTGGGGATGGGGAAAATGA
GAGAATCAAACGACTAATTTAAGTGTAACGATTTTTAATTAACGATTTAT
AAATTAATAAATACTTGATTGATACACAATTTAGATAATTTAAAATAAAT
TTTATTAAATGATAAAATTAAATTGCCGTTTTAAAAAAAAAAAAAAAAAA
AAAAAAAAAAAA

>7A01>msp6>>bankit482263>>>AF531165 (SEQ ID NO: 13)

GACCATCAAATCATCTCCTCATCAACTAAAAATCCCTAAAAACACCCCAA
AACATCCATAAAAACAACCACGAAAATGGCCACCTTTTTCACTTTTACCC
TTCTAATCATTTCAATTATTGCCACAACTGAGGGAATGAATACTAATCGA
AGTGCTTCAACCTCCGATTCTCTCAAAGCCCAAAAGGATTGTAAAGTGAT
ATATGGCATGTTTGTGCCTGTAGCAGGGTCAAAAATGCATGGAGACGCCA
AAAGCGCAATGAAGCCAAACAATCCAAGTCTCTCCAATAAATTAATTGTA
TCAGGTGGCAACTCAAAATATTCAGTGACTTTACAGGTTGAAAACCAGCC
GAAGTGTGTTGCCCAAAATGACGGAAACCCTGTAGAATGCCAAATTCAAG
GAGACAAACTTTCAGGAAAATTGATTTATGATATTGAAAACGGCCCTTCT
GTCAACGTTCCCTTCAAAGACACCCCAATCTTTGTTGGAAATAAATGCGA
AATTGTTTTTGTAGACTACGATAAGGACCACAAATTAACTCTTCTTATGA
ATAAAGTAAAGCTGATGATTGAGCCGACTGAAAAGCAAATTGTAAAGGCT
TGTGGAGTGAAAAATTAGATGGAAAAATGATATATGAATGAATGAATGTG
AGAGGGAGGGAAAGAAAAATATTTTTAAAATTGAAGAAAGCATTCAAAAA
AATTAAAAAAAAACAATTCTTCAAATAATATAACCTTAAAATTTCTGATA
AATTATGTTTTTACAAAAAAAAAAAAAA

>7E12>msp7>>bankit478534>>>AF531166 (SEQ ID NO: 14)

GCCATCAAATAATCTCCTCAACAACTAAAAAACTCAAAAAAACACCCCAA
AACAACTCTAAAATGGCGGCTCTCCTCTTCACTTCTACCCTTCTAATCAT
TTCATTGGCTTTTATTGCCATAGCTGAGGGAGCAGGCGATCGAAATGCAT
CAGCTTCAAGCCCTGGTTGTATGCAGGTTGCAACCCTTATTCATATAGGG
GAAATTCGCCCAGCAAAAGCAAACAAACCAGGTGTACAAAATACTCTAAA
AATGTCTGGAAATGTTCAAACATTCAAAACTACTCAAGTGACATTACAAG
TAGCTGGGCAAGAGCCTTGTACCGTTAAAATTAATAATGGCGAAACCAAA
TGTAAAATAACCGGAGATGAATTAAATGGAAAATTAATTTTCAAAACTGA
AAAAGGAACTGAAATTTCTGCTTATTTCGAACTGGTTCCATTATTTTCTG
AAAATAAGTGTGTTATTGAACTTGACACTTATAACAAGGAAACCCATGAA
ACTAAACTTAAAATTAATGGAAATAATTTTATGATTAAAAAGAAGGAAGG
TAATGTGTCAATTAAGTGTGGTGGAAGAGCTAATACTGTTTAAATTTTAA

TABLE 2-continued

AAGTGTGAATTGAAAGAGGAAGAGAATAAACAAATGTGAAGATGAGAAAA

AAATATTTTGAAGAAAGCATTATAAAAATATTAAAAAAAATTAATTCTTC

AAATTTTTATTTGATTTTTGAATAAATTATTTTATTAAAAAAAAAAAAAA

AAAAAAA

>7H08>msp8>>bankit482285>>>AF531168
(SEQ ID NO: 15)
GCTCATTAATTAGTTAAAAAATTTAAAAAATAATTTAAAAAATGAAAATT

TATTTTAATTTAATTGTTTTCTATTTATTTTAAATTTTTATTTTGTCGA

ATTGGCAAAAAGGAAGGCAACGGATACTGAGATTCCTGAGCAAAATAAAA

AGCAAAATACAAGCAACCATGCCCATCAACAATTAACTCCTTCTTCTTCA

AATGCTGATAATGAGAAGCAAGGAAATCTTTCCTCTGAAGCTTCAAATAT

TCGAGGAAAAAATATTCTGCATGATCAGTCTGCTATTAAAAACAATTCGT

TAACTAATCAACAATTAGGAGCCTCCTCTTCTAATGCTGGGCAACAGAGA

AATAATAATTCGGATCTTTTAAAATTAACAATTATAAATCATTTGTTATC

CCATCGCCAATTTAATGCCTCTTCTTCAAATGCTGGTCAACACAAAAATA

TTCCCTCCGAAAATCTAAATTTTCATCAAAAAACTATTCCAATTGCTACT

AAAAATAATTTGTTCCCCAATCAGCAATTTATTGCATCTTCTTCAAATGA

TCTTGATTTTCAACAAAAAAATATTCCATATGGAACTAAAAAGAAGGTGT

TACATCAATTTATGCCATCTTCTTCCAATGCTAATAAACGCAAAAATAGT

TCCACGGAATATTTAAAATATGCAATTAAAAATAGATTTTTATCTAATCA

GCCATTTGATGACGACATTTATGGTAAAAAGAAAAATGTTTCCCCGGAAT

ATCAAAATATTCAACAAAAAAATCTTCCATATGTCCAATATGCTATTGAT

AATAATTTGAAATTGCCAATTCCAAAAAATCCTAAAGCACTTCCATATGA

TTTGTCTAAATACGCATTTAACTTCCCCAATATGAACAAGAAAAATATTT

ATGAAGGAGCATATGATCCTTATTATATTAATTTTCAACAATAACAGATT

TGGCTAATAAAACGTTGGAAAACGACTAAGAAGTTATACATTTGACATAA

ATTAAATAAATAAAATTAAATTACTATTATAAAATTGTTAATTATCGTAA

TAAAATTTTTTAACTCAAAAAAAAAAAAAAAAAAAAAAAAA

>8D05>msp9>>bankit478548>>>AF531169
(SEQ ID NO: 16)
CTAGTCAGTCATTTAAAATAATTTAATATTCCTCTAAAAATCCCTAAATT

AATTTAAATATTTCTTTAATCAATTTTTCTTCAAAAAATTTAAAGAAGGA

AATGTTTTTACAAAAACAATTATTGTTTTTGGTTGTTCTTCTATTAGCCT

TTTCTCTTGTAAAGGGAGTAACCGAGAATAAGAATAAAAGCGAAATAAAA

AATGAAACAACCACAAAAGTAATTCAAACATCAACTGGAGGTTATGATGA

TAACGAAAAAGCAGACTATGGCGATTTGGCTGCAGAATTGGCTAAACTTG

TTGAGGAGGAAGATGAATTAAATAAAAAGAAGAATGCTTTGAGTTCGGAG

AATGGAAATAAAAATAGCACAGGAAAGCCTTATATTCAAAAAGATAAAAG

TAAAAAATATTTGGAAGAAGATAAAGGAAAATATGAGGAAAGAAATTCTA

GAAATAAATATGAAAACTCGGATGAAACCCATGAAAGTGAATCAGGTTCA

AGTTCGGATGAGGATTTAGATGAAGATAATTTAGAAAGATTGCCAGGGCC

TTCGCCACACAATGAAGGAATTTCTAGGCGAAGAGTTGAAAAGGAAAAAG

TABLE 2-continued

GTGGAGAAGATGAGGAGGAGGAAGAAAAAGAGCAAGAAAATTCTAATGAT

AAAGAAGAAAGAAAGAAGAAAAGGAACACCAAATATAATCCAAAAGATGA

GAGTGAGGAAGATATTTCTTTTGATGGTCAAATACCTAAAAGTGTACGTA

AATTACTTAAACAATTAGCAGCTGGTGGAAAGAATCCTGTAATTATACCT

TTAATTATAAATAACAACAATATACCGAATCGAAGAGAAGATGAGTCTGA

GGAATGGAATAAAAAAAGACATGGGAGACCTCATAGATTAAATGATTGGA

ATAATCCGTTTCCTCCATTCTTTCAATCTTCAATGTTTCAACCACCAATG

TTTCAACCACCTATGTTTCCACCACAACAGCCACCTTTTGGTGGCCCTCC

AACATTTGCTCAGCACTTAATCTTCCTGGAGGGCCTCTCGGAGGAGGTCT

TGCTGGCAGTCTTCCCAACACAAATCCATTTTTATCACAACTAAATCGTG

GTGTAAGTCCTAATCAATTTCCCAATCCTCCCTCTAATCACGTTCCACCT

TTTGGGCAACAAAATCAATTCTATCCTCCTCAACAACAACAACAAAATCA

AGTCAACCCACAGGGAGCAGATGGCAATGATGTGAAAAAAGTGAATTAAA

CAAAAAAAAAAAAAAAAAAAAAAAAAAAAAAA

>8H11>msp10>>bankit478550>>>AF531170
(SEQ ID NO: 17)
GATCGTCATTCTTGTAAACTAAAAATCTTCAAACTTCAAAAAATATTCCT

TAAACTTCTTCACAAAAAGAATTGAAAAATGTTATTAAAATTCTTTCTCC

CATTATTGCTTTTGGTTACCCTTATCTATTTGGGGTGTTCTGAGGAGGAT

AAGGAAGACATTGCAAATGGTCCTCAGGAATCTGAGAATCAGGTTGATCA

AGAATTGGTTAGATTGAAAAGAGATGATGAAGAAGAGGAGGGAGAGAAGG

CTGAAGATGAAGAGAAGCCTGAAGAGGAGGGAGAAAAGGCCGAAGATGCT

GAGAATGCAGAAGGAGATGCTGATAAAGGAGATGCTGATGAGGAAGAAAA

AAAAGAAAGTGAAGATGAAGAGAAAAAGAGTGAAGGTGAAGAAGAAAAAG

CGGAAGGTGAAGAGGAAGAAAAAAAAGGATGGAATTGAGGAAGAAAAGAAG

GATGAAGATGAAGAAGAGAAGAAAGATGATGATGAAGAAAAAAAACGAGGA

AGAAGGAAAAAAGGATGATGAAGAAGAAAACGTAGACAAAGAAGAAAAGA

AAGATGATACGGAAGAGAAAGAGGATAAACATTCAAAGGATAAAAGTAAG

AAGGATAGTAAGTCCGTTCAAAAGGATAAAAAGGAGGAGAAGGAGAAAAA

GGATAAAAGTTCAAGTGGTGATAATTCTAAAACAGATAAATCAGATAAAT

CACATAGTAATCAAAAACAAGACAGCAAAGAACCATGTAATGGGGATACT

GCTTACAACTGTCCTAAACTATCAGGTCTTTGTGAATCAAAAATTCAAGT

ACAACAAGACTTCATGGGTGAAAAATGTTGTGCTACATGCAAAAATTCGG

TTCCTGTCGCGAAGAAAGATATACCCTTATGCACTGATTTGGCTGATAAT

TGTGATCAAATAGCATCCACCTGTGGGGAAGAGGCGTGGCAACCGACTAT

GATTTCTGATTGTGCTCAGACATGCGATAAGTGTGAATTACATTTTCAAA

TGTTGGAAAAGAAACTTGCAGCAGCTGCTGCTTAAAAATTTTGAAAGGAA

AAGAATTTTTATCAAAAATATATGTATCAAAAATATATTTTCTTTGATTT

TCACACCCTTAATACTAAAATTTCAATTTATTCATCAGTGTTTCTCGTAA

TTATATTTTATTAATTTGTTTCGAGATTTAGTAAAGATGCTTTAAACCAA

AAAAAAAAAAAAAAAAAAAAAAAAAAAA

TABLE 2-continued

>9H10>msp11>>bankit478544>>>AF531167
(SEQ ID NO: 18)
GGAATTTTTCAAAAAAAGTAGGCTGGAGAATAAATTTATTGAAAAACCAG
AATTCTTAAAGTTTCAACCATTTAAAAAATGTCAAACAATTTTAAAACTT
GCCCAGCTTTATTATATTTATTGCTTCTGTTGGGAAAAGCAAGTTGCAAT
TATTTTGAATCAGAATTAAGCTTAGCTAATGACAAAACTTCTATAGTTCG
CAAATGTTGTCCTAAGGAGAAGATTAGACACCATCGGAGACCGTTGCATT
GCTGCCAGGATGGGTTATTCCGTGATGAAGTTGATGGTTATTTATTAAAA
GAATGTGCAGATCAAGGTGATTCCATAGTCAAAACAATTAGATGTGCTCA
ACAAGAAATACATGGTGAAAATGCAGTGGAGATTTGCAAAGCCTATTGCT
GCGAATTATTCAGAGATAATAATTGTTCCAAAATATGCCTAACAAACATT
ACCAAAGTAAACATGTCTATTGAAATATTATTTGAGCTGTTAAAAAAATG
CAGGAATCATGAGAATTATGGGGAAGTCCATGACTGTATCCATTCAAAAA
GACCAAAAAACATGGATGCCGCAGAGTTGGAAATTTATTGTAAAAGGGCT
ATTAATATGGTTTAAATCTGGAATTTATTTTTTAATTTATTCTACTCGAT
CTCCTTTTATCTATTTAATTATTAATTTATTTTTGGCAATAAAATTTAAT
AAAAAATGTAAAAAAAAAAAAAAAAAAAAAAAAAAAA >10A08>msp34>>bankit487923>>>AY142117
(SEQ ID NO: 19)
GGTCGTCATTCTTGTAAACTAAAAATCTTCAAACTTCACAAAAATATTCC
TTAAACTTCTTCACAAAAAGAATTGAAAAATGTTATTAAAATTCTTTCTC
CCATTATTGCTTTTGGTTACCCTTATCTATTTGGGGTGTTCTGAGGAGGA
TAAGGAAGACATTGCAAATGGTCCTCAGGAATCTGAGAATCAGGTTGATC
AAGAATTGGTTAGATTGAAAAGAGATGATGAAGAAGAGGAGGGAGAGAAG
GCTGAAGATGAAGAGAAGCCTGAAGAGGAGGGAGAAAAGGCCGAAGATGC
TGAGAATGCAGAAGGAGATGCTGATAAAGGAGATGCTGATGAGGAAGAAA
AAAAAGAAAGTGAAGATGAAGAGAAAAAGAGTGAAGGTGAAGAAGAAAAA
GCGGAAGGTGAAGAGGAAGAAAAAAAGGATGGAATTGAGGAAGAAAAGAA
GGATGAAGATGAAGAAGAGAAGAAAGGTGATGATGAAGAAAAAAACGAGG
AAGAAGGAAAAAAGGATGATGAAGAAGAAAACGTAGACAAAGAAGAAAAG
AAAGATGATACGGAAGAGAAAGAGGAATAAACATTCAAAGGATAAAAGTA
AGAAGGATAGTAAGTCCGTTCAAAAGGACAAAAAAAAAAAAAAAAAAAAA
AAAAAA >10G02>msp29>>bankit479222>>>AY135365
(SEQ ID NO: 20)
ATATTTATTTTTTAATTTAACAAAAATATTTTTAATTAAAATTATTTATT
TAATGTTTAAATTGTTGTTTTTCATTTTGTTTGCCTTATTAAATTCTGTT
GATTGTCTTTTAAAATTACGAACACTGGATAAAGAACATCTTCTGGTTGA
GGAGAGATATGCCAAGGAAGATACGCTTTATCTTTTTGTTTTTCCTAGAA
CATCAAATGCCCCATATTTTGGAGCAATGTGTCTTTATGTTGAAGCTGTT
TTAACTTGGAAAGGAATTCCTTTTCATAGAATAAGTAACCAATTCTTTCT
TGGTTCAAAAACTGATGGAGCAATTCCTTTTGCTATTTATAACGGGAAAT
ATTTGGATGGAGCAGAAAAAATAATTGAAGAAGTTAGAAAAAAGGGAAAT
AAAAAATTGAGTGATGAACATGATGATAATATTAGAAAATTTGCAACTAG
AACCTTGCTAAAGACTCTAATTGCTGATAGAACATTTCGGAGAGATCTTC
CCCATGCAACAATTCCAAAAAATAATTCCGAAACACAAATAGCCTCTTCT
TCATTATCAAATAGTGCACCAGCAACTCCCAAGGGTGGAATCCCTACAAG
AAAGAGATTTAGTCCAATTGATATTAAAATCCCTCATACTAAAAATGAAG
AAATAATAATGGCAAAATCTGAGGGGCATTCTCCTGGAAGTTCTTTCTTT
TCTAGAACTATTGCTCATTTAAAATTACATAATAATAATTCTCCAAAGAA
AGGTCCGGGTGGTCTTGATTGGATGTTAAAAGATGAAGGAGTTCGTGAAC
AATTAATTCCAGTTATTCCAGAGGCTTTTTTAGAAGAAAGTATGAGTGAT
GAATATTTTGATTCCCCGGTAAAAGATAAAAATGAAAAGAAATCAAAAAG
AGAGGAGGAAGATGAAAGTGATGAAACAAAAATATCTAAAATTAAATATT
CCATTAAATTGACGTTAAGTCCAGAATTGTGGAAAGATTATTTTAATATT
TTAAATAAAATAAAAATAAATGGAAGGGAAAATAGAGAAGAAATTAATTT
ATTGAAAATAAATTTTCTTCAAGAATATTTCGGATTCTTAGCAAGAATTG
ATGATGATTGGGAACGTGTAAATTCTATTCTGAAAAATACAATTAACGAT
ATTTTAAAGAAATTAATTGTTGATAGCCAAATACCTTTTTGTTGGGAAAA
AAGGTTGAGAGAGATTAATGGGAAAAATATTAATGAAGTTGAAGTATTTA
ATGAATTTAAAGATAAAATAAAATCGTTGGGTATAATAAAAAGTTGACTG
AGGCAGAGACTAAAAATAATTTTTTGCATGGAAATAATCCAACTTTGGCT
GATTTTGCCCTTTTTGCTTTTCTCAATCAATTTTTTGAATTTCCTTTAAA
TATTCCAGAATTTAAAGAATTATTTACCCCAGAAAAGCTCAGTAATGAGG
AAAAAGAATTAATTGCGAAAAAAAAAAAAAAAAAAAAAAAAAAAAAAAAA >11A01>msp12>>bankit478790>>>AY134431
(SEQ ID NO: 21)
GGCATCAAACAATCTCCTCAACAACTAATAAACTCAAAAAACACCCCAAA
ACAACCCTAAAAACAACCCAAAAATGTCCATCTTCCCTACTTCTGCTCTT
CTAGTCATTTCAATAATCGCTATGACCGAGGGTGCAGGCGATCGAAGCGC
TTCAACCTCTACTGGTTGTACAACCTATTTTGGCATGCTTGATCATGCGG
ATACCAAGGAAAATAACAAAAGAAAAACTTTCAAACCCAACGATAAAACC
AAATCCAACACCTTGCAAGTGACTGGTGGGGCAATGTTCAGCAATACCTC
GGTGGCGTTGGTTGTCGGTGATAAGGCGTTATGTATGGCTAAGACAGGAA
GTTCAGACGATTGCGGAATGCGCTACGATGCTTTGACTGGAACAATGAAA
TTTATCATTTCTGATAATATTACTGTTGAAGTGGGTGTGGGTTTATATAA
TTGGTGCCAGACAAATGGAAAGGCCCCTGTCACTAACATACCATCCGGAG
CGTTCATGTTGCCCCGGAAGTAACTGGTGGCCCACAAAAGGGCAATCACT
ATTGATTACAACCCAAATATCTATAGGATTTTGACATTTTCTGGCATAAT
TTAGGTATTTTCTGACATTTTTCTGACATTTTTAACTAGAATTAATTCAA
TTGAAAACAAAATAATAGGATTGACCTAAATGAGCGTTTCTTGGATATCC
TTTTAACAGGAGCAGTCTCTAATTTTGTAAGAGCTCCTAATGTTTACCCT
CCTCCATCTCCCTCCCCCTCTATGCTCCTACCAATGACTGATTAAGTTAA
AAATCGTACATAAAATGGAGAGTGTATAAATCTGGGTGTATATACAATCA TABLE 2-continued GGATTCGACTTTATAACATTTGAAGGTTCCATTTGAAGACGTTTTTTTCT
TCACCGACAACAAGTGTGTCATCCAGCTTGTAAGCTACGATAATAAAACT
AATAAAACTCTTCTCAAAATTAATGATGTCGACTTCAAAATTATCCCTAC
TGATAAGAAAATTTCCCCGAAGGCTTGTACTATGAAAATGTGAGCTTGTA
CTATGAAAATGTGAGGGAAAAAAGTAAAGAAAAGAATAACAAAAAGTGTA
AATATGGAAGGATAAAAACGAAACAAAAATGAATGTGAAGTAAAAAATAA
AAAGAAATTCAAGTAGATTTAAAAAAAATGTTAAGCTTCACAATATCTGT
CTCCTTTTGTTTATGTTTTTCGAATAAATCGCATTACCAAAAAAAAAAAA
AAAAAAAAAAAAAAAA >12H03>msp13>>bankit482577>>>AY134432
(SEQ ID NO: 22)
GAATCACAAAAATGGCCACCTTTTTCACTTTTACCCTTCTAATCATTTCA
ATTATTGCGACAACTGAGGGAATGAATACTAATCGAAGTGCTTCAACCTC
CGATTCTCTCAAAGACCAAAAGGATTGTAAAGTGATATATGGCATGTTTG
TGCCTGTAGCAGGGTCAAAAATGCATGGAGACGCCAAAAGCGCAATGAAG
CCAAACAATCCAAGTCTCCCCAATAAATTAATTGTATCAGGTGGCAACTC
AAAATATTCAGTGACTTTACAGGTTGAAAACCAGCCGAAGTGTGTTGCCC
AAAATGACGGAAACCCTGTAGAATGCCAAATTCAAGGAGACAAACTTTCA
GGAAAATTGATTTATGATATTGAAAACGGCCCTTCTGTCAACGTTCCCTT
CAAAGACACCCCAATCTTTGTTGGAAATAAATGCGAAATTGTTTTTGTAG
CCTACGATAAGGACCACAAATTAACTCTTCTTATGAATAAAGTAAAGCTG
ATGATTGAGCCGACAAATAAGCAAATTGTAAAGGCTTGTGGAGCGAAAAA
TTATATGGAAAAATGATGAATGAATGAATGTGGGAGGGAAGGAAATGAAA
AATATTTTTAAAATTGAAGAAAGCATTCAAAATTTAAAAAAAAAACAATT
CTTCAAATAATATATAACTTTAATATTTTTGATAAATTTTATTTCATAAA
AAAAAAAAAAAAAAAAAAAAAAA >13A12>msp14>>bankit478806>>>AY134433
(SEQ ID NO: 23)
GGCATCAAACAATCTCCTCAACAACTAATAAACTCAAAAAACACCCCAAA
ACAACCCTAAAAACAACCCAAAAATGTCCATCTTCCTTACTTCTGCTCTT
CTAATCATTTCAATAATCGCTATGACCGAGGGTGCAGGCGATCGAAGCGC
TTCAACCTCTACTGGTTGTACAACCTATTTTGGCATGCTTGATCATGCGG
ATACCAAGGAAAATAACAAAAGAAAAACTTTCAAACCCAACGATAAAACC
AAATCCAACACCTTGCAAGTGACTGGTGGGGCAATGTTCAGCAATACCTC
GGTGGCGTTGGTTGTCGGTGATAAGGCGTTATGTATGGCTAAGACAGGAA
GTCCAGACGATTGCGGAATGCGCTACGATGCTTTGACTGGAACAATGAAA
TTTATCATTTCTGATAATATTACTGTTGAAGTTCCATTTGAAGACGTTTT
TTTCTTCACCGACAACAAGTGTGTCATCCAGCTTGTAAGCTACGATAATA
AAACTAATAAAACTCTTCTCAAAATTAATGATGTCGACTTCAAAATTATC
CCTACTGATAAGAAAATTTCCCCGAAGGCTTGTACTATGAAAATGTGAGC
TTGTACTATGAAAATGTGAGGGAAAAAAGTAAAGAAAAGAATAACAAAAA
GTGTAAATATGGAAGGATAAAAACGAAACAAAAATGAATGTGAAGTAAAA TABLE 2-continued AATAAAAAGAAATTCAAGTAGATTTAAAAAAAATGTTAAGCTTCACAATA
TCTGTCTCCTTTTGTTTATGTTTTTCGAATAAATCGCATTAGCAGCAAAA
AAAAAAAAAAAAAAAAAAAAAAAA >14E06>msp15>>bankit478812>>>AY134434
(SEQ ID NO: 24)
GAAATAATCTCCTCAACAACTAAAAAAACTCAAAAAAACACTCCAAAACA
ACTCTAAATGGCTTTCCTCTTCACTTCTACCCTTCTAATCATTTCATTGG
CTTTTATTGCCATAGCTGAGGGAGCAGGCGATCGAAATGCATCAGCTTCA
AGCCCTGGTTGTATGCAGGTTGCAACCCTTATTCATATAGGGGAAATTCG
CCCAGCAAAAGCAAACAAACCAGGTGTACAAAATACTCTAAAAATGTCTG
GAAATGTTCAAACATTCAAAACTACTCAAGTGACATTACAAGTAGCTGGG
CAAGAGCCTTGTACCGTTAAAATTAATAATGGCGAAACCAAATGTAAAAT
AACCGGAGATGAATTAAATGGAAAATTAATTTTCAAAACTGAAAAAGGAA
CTGAAATTTCTGCTTATTTCGAACTGGTTCCATTATTTTCTGAAAATAAG
TGTGTTATTGAACTTGACACTTATAACAAGGAAACCCATGAAACTAAACT
TATAATTAATGGAAATAATTTTATGATTAAAAAGAAGGAAGGTAGTGTTT
CAACTAAGTGTGGTGGAAGAGCTAATACTGTTTAAATTTTAAAAGTGTGA
ATTGAAAGAGGAAGAGAATATAAACAAATGTGAGGATGAGAAAAAAATAT
TTTTGAAGAAAGCATTACAAAAAAAAAAAAAAAAAAAAAAAAAAAA >16D10>msp16>>bankit478814>>>AY134435
(SEQ ID NO: 2)
GAGAAAATAAAATATAAATTATTCCTCAAAAATACCATAAAGTTAATTAT
TCTTCAATCAAAAAAATGTTTACTAATTCAATTAAAAATTTAATTATTTA
TTTAATGCCTTTAATGGTTACTTTAATGCTTTTGTCTGTCTCATTTGTGG
ATGCAGGCAAAAAGCCTAGTGGGCCAAATCCTGGAGGAAATAATTGAAGA
AAAATGATTGAAGAAAAACGTTTAAATTAAACGATAAATGGGAAATAATG
GAATTTAAATTAAGCTAATTTTGATGGTTTCCTTTGTTAATTTCAACATA
AAATTAATTGAATTTACTGAATAAAATTATATCTGAAAAAAAAAAAAAAA
AAAAAAAAAAAAAA >16E05>msp17>>bankit482587>>>AY134436
(SEQ ID NO: 25)
GATTCAAAAAATATTATTTAAAAATTCTTTACCATTTAATTAACAAATTG
TAATAAAAGAAAGACAATTAAAAAATGAGTCCTTCCTCATTCACCTTAAC
GGCAGTACTTCTTGAGGCGATTGTTTTTCTTTACAACCGTCAAGTAGCGG
CAATGCTTTCCATGCATCCGAGCTGTTCTGGCCGTTCATCAACCATTGAG
AATAAATTGAAAATGAGCGGGGGTGGTAACGGCATCAATAAATTTACACC
GGGAAATGTTTCATTCCCGGTAGCATGCCAATACCATTCAAAGAATCTCA
AAGCAACAAATAAAAAGGAATATAAAATCTCAGAAGATTTGCCTATGAAT
CAAGAAAAGCTTACAAACAGTAAGGAAGATGATCTCATTCATAAGGTAAA
AAAGATAGATAAGGGCAATGGAGCTGCTGTTCCTTATAAAACAAACAAGA
ACAATGAAATTGGAGATGGAGCCGAGAATGGAAAAGCTGTCAAAATTAGA
GAAATTATTTTTACTGAAGAGCAAAAGAAAATGACTAGCGAAGAATTTGA
GCATTATTTGTATAGTGTTCCATATGACAAAAACAAGAAAAACAAAATTG TABLE 2-continued GAAAAAACGAAAATGGTGAAAAAGTTGATAAACCAAGCAAAGAAGGAGGA
GATACAATGTTTTATTCAAAAGCTGGGATAATTGCTAAAAAGATAAAAGA
ATATGTCCCCACTAATGGCGAATTCAAGATCCAGACTGGACTTGTATATC
GTAACAATAGTTTTAATGCTTCCCAAGATGATAGTAAAAATTTACTAAAT
ATTTCGCATATTTTAATGGCTTTAAATGAAAATGAGAGGGATTCTCAAGA
AAATTTGAGAAATGCTGCTGATTTGTTTGTGGCACTTCATGAGTGTTACC
AACTCTTTTCGGCAATTCCTCTAGTTTTTGAAGTAGAAATGGTTTTGAAA
AAACTTGAGGAAGAGGGAAACAAAGACGATCCAATAAAATTACTCGAATA
TTTCCGTTTGCCAACAATTAAATATCCATTATTGGATTTGATTAAAATTG
AGAACTCAACTGTGTCTCCAGATGAGTTGATTGAAAACGTCACTAAAACT
ATTCACAAAGCAGACAATTTTATTGCTAAAAACATCCATGCATTCTTCAT
AAATGACAACGAAACATTTTTTAATGAAATAATTTCTCGTCTTGAAACAG
CTGATATGGTTTTGGCCAGTATCAAAAAAATTCTTAAAATGTTCAATAAC
TTTAATGAGAAAATTCCCGAAAACTTTTCGATGCTAAAACGTTTAAAACC
AATTGAAATGCACGATTTATTCGAAAATTCTAAACTGCTTCAAAAGCTTC
ATGCAGCAATTTTGCCTGGAGATGAAATGAAATTTTGAAATGAGAGTTAA
ATATTTTTAAAAAAATTTTGCGAACACAAAAACAACAACAAATTAGAAGA
ATATTAAAATTATTAATGAAACAAGAGTTGCCGCGGCTGATCGGAAATAT
TAATTAAATCCAATTTAGCTGACGTTGCCTGCTCAATCACCAAATAAATC
AATTTATGATTTTGCCCATTCTCTATCATTACCTTATTTCCTATTTGTAC
ATTTTTTTTTCTTTTTTAAAAATTATTTTTAGTTTTGTTCTTGAATGTTC
GCTTAAATAAATTCTAAAAAAAAAAAAAAAAAAAAAA >17H02>msp18>>bankit482591>>>AY134437
(SEQ ID NO: 26)
GATCAAACAATCTCCTTAACCACTAAAAAACTCAAAAAACCCCCTAAAAG
CAGCCCAAAAAATACCCAAAAATGGCCATCCTCTTTACTTCTACCCTTCT
AATCATTTCCCTTTTGGGAATTACCGAGGGAGTGAATACAGGCATTCCGA
GCGGATCTTCTCCACCCTCTTCTGCTTGTGAGACTTACAAGGGCAAAATT
GAGCACATGCCAGAAACCGCCAGAAAAATTGAATGGAAGGAAAATACTCC
CGGAGGAAAGCATTTAATCCTTAAAAAGTCTATTCAAGGTCTAGACAAAG
TAACCCTCAAAATTGAAGGCAAAGAATGTAGTGCTTCCCTCAACAACCCT
GGAACATGTCAAGTCGATGGACAGTCCCATGCCGGTCAATTAGTCTTTGT
AACTTCAAAGGCTAAAATTGAGGTTGACTTTGGGGAAGCTCAAATCTTCT
CTGGGAACAAGTGCGAGATTGAAATTGAGAAGTATGACCGTGCTACCTAC
GTAACTCTAATCAAAATTAATGGGGGTGACTTCAAAATTACGCCTGATTC
GCCACCTATGCCGATGCCATGCAAAAATATGATGAACTAAAAAGTGAGGA
GGAGGGAAGGAAAAGTGAAGGAAGAGACCATGTAAAATTGAAATATTGAA
GAAAGCATTCAAAAATTTAATTTTTAAAAAATCTGTTTGTTTAGTAACTA
AATATAGCTTTCTATTGTTCTTATATTTTGTTTATCTTTATCAAATTAAA
ATGAAAACTCAAAAAAAAAAAAAAAAAAAAAAA TABLE 2-continued >19F07>msp32>>bankit484054>>>AY142116
(SEQ ID NO: 27)
GACATTCATTTAAACATTCATTAATTACCTAAAATTGTTTTTCAAATTGT
TTGCCTCTGAGTTTTGCTCAACTGAGAAGAAAAATGCTTCCTTACTCAAT
TCTATTTCAATTGGGAATAGTTTCGTTGCTTCTACCTCATGCAAATGGAA
TGCAGTCTGGCAGTAGCAAAATTATGAACAAAGCATCTGAAAAGAAATAT
GCTTTGGTTGTTGCTCCAAACTTTCTTAAAGTTCATTTTAAAATGAACAG
TGTCTTTGCCAATGCGTTGACCAAAAAGTTTTTTGTGCACTTTCTAATTC
TGAACACCAAAAATGAAGAAATTGGAGATAATTTCGACTATGGAATTGAT
CTCGAAAAATTTGAAGAAGGAACGGGAAATACATATCAAGTTGTAAATTT
TCCAGATGATTATCCCGAAAAATTGAACGAAGGCGTGAAGAATTTAGAGA
ACAAATTCATTAAGAGAGGTTACGAACAGAGTAGTCAAATTCTGAAAAAT
GAAGCTTTCACCGTTTATAAAGATTTATTTGAAAACAATGGAGCTATTGT
TCATTACTTGAAGGAGGCAAAGTTTGATTTAGGGGTTTTTGACACTTGGG
ACACTGGAGCTCTCTTCATTCTCCATGCAGCAGGAATTAAAAATGTTTTT
GGCATTAACAACATTCAACTTAATGCTTATCAATTTAAATATGCTGGGAA
AGAATTTCCAAAAAAATATTCCAGAAATTTAATTCGGCACAAACAGGCGAT
AATGAATTATCACCAACAAAGGAAAAAAAAAAAAAAAAAAAAAAAAAA >21E02>msp19>>bankit482599>>>AY134438
(SEQ ID NO: 28)
GGCATCAAACAATCTCCTCTCCTCAACAACTAAAAAACTCAAAAAACACC
CCAAAACAACTCTAAAATGTCGGCTCTCCTCTTCACTTCTACCCTTCTAA
TCATATCATTGGCTTTTATTGCCATAGCTGAGGGAACAGGCGATCGAAAT
GCATCAGCTTCAAGCCCTGGTTGTATGCAGGTTGCAACCCTTATTCATAT
AGGGGAAATTCGCCCAGCAAAAGCAAACAAACCAGGTGTACAAAATACTC
TTAAAATGTCTGGAAATGCTCAAATATTCAAAACTACTCAAGTGACATTA
CAAGTAGCTGGGCAAGAGCCTTGTACCGTTAAAATTAATAATGGTGAAAC
CAAATGTAAAATAACCGGAGATGAATTAAATGGAAAATTAATTTTCAAAA
CTGAAAAAGGAACTGAAATTTCTGCTTCTTTCGAACAGGCTAAATTGTTT
TCTGAAAATAAGTGTGTTATTGAACTTGACACTTATAACAAGGAAACCCA
TGAAACTAAACTTAAAATTAATGGAAATAATTTTATGATTAAAAAGAAGG
AAGGTAGTGTGTCAATAAAGTGTGGTGGAAGAGCTAATACTGTTTAAATT
TTAAAAATGTGAATTGAAAGAGGAAGAGAATATAAACAAATGTGAAGATG
TGAAAAAATATTTTGAAGAAAGCATTCCAAAAAAAAAAAAAAAAAAAAAA
AAAA >25B10>msp33>>bankit487909>>AY142118
(SEQ ID NO: 29)
GACATTCATTTAAACATTCATTAATTACCTAAAATTGTTTTTCAAATTGT
GATTTTATTTATTTCTATTTAATATCTTTAAATGCGGAGTGCTTTAAAAA
CTTTAATTGTTTTGTGGCCTCCTTTGCTTGGACATTTTATTTTGTTAATT
CCTAGTGGAGTAGCTTTTGTAGTTAAAGAGAATGTTCAAGAAGTATCGCC
TGTTATTCCTGATAAACCCGGAGTAATTGGAGGTGATGTTATTGATAAAA
GCGCAAAAACTAGTCAACTAAAAAAGGGAAGTGAAAGTCTGATTTCTGGA TABLE 2-continued ATTGAACGTAGCCATGTTGAGGAATTAAAGGAGGAAATTAAAGGAGAAGG
TAAGAAAGTACCCAAAATGAATGGACAGGATAATGAAAGCCTTGAAACTA
AAATTGTTGAAAAG >28B04>msp35>>bankit484130>>>AY142119 (SEQ ID NO: 30)

GATCAACCAATCCCCTCAACAACTAAAAGACTCAAAAACACCCCAAAACA
ACTCTAATATGGCTCTCCTCTTCAGTTCTACCCTTCTAATCATTTCATTT
ATTGCCATAGCTGAGGGAGCAGGCGATCGAAATGCATCAGCTTCAAGCCC
TGGTTGTATGCAGGTTGCAACCCTTATTCATATAGGGGAAATTCGCCCAG
CAAAAGCAAACAAACCAGGTGTACAAAATACTCTAAAAATGTCTGGAAAT
GCTCAAATATTCAAAACTACTCAAGTGACATTACAAGTAGCTGGGCAAGA
GCCTTGTACCGTTAAAATTAATAATGGCGAAACCAAATGTAAAATAACCG
GAGATGAATTAAATGGAAAATTAATTTTCAAAACTGAAAAGGGAACTGAA
ATTTCTGCTTCTTTCGAACAGGCTAAATTGTTTTCTGAAAATAAGTGTGT
TATTGAACTTGACACTTATAACAAGGAAACCCATGAAACTAAACTTAAAA
TTAATGGAAATAATTTTATGATTAAAAAGAAGGAAGGTAATGTGTCAATT
AAGTGTGGTGGAAGAGCTAATACTGTTTAAATTTTAAAAGAGTGAATTGA
AAGAGGAAGAAAATATAAACAAATGTGAAGATGAGAAAAAAATATTTTGA
AGAAAGCATTCCAAAAAATAAAAAAAAATTAATTCTTCAAATCCATTTAT
TTTTTGAATAAAACATTTTACTAAAAAAAAAAAAAAAAAAAAAAAAAA

>30G11>msp21>>bankit482611>>>AY134440 (SEQ ID NO: 31)

GATTTTTATTAATTTTAAAAATTATTAACTCTCCAAAATGAAGTGTTTGC
TCCCCTTCTTTTGGATTTTATTAACAATTTTTGTTTCTTGCACTAATGGC
ACTTCAAATGAGTATAGTGAACTTGTTTTGGTTCAAGCTTTGTGGAGACA
CGGTGATCGTTCACCCACAAAAACCTTCAAAACGGATAAATATCAAGAAA
AGGATTGGCCTCAAGGATGGGGGCAATTAACACCTACAGGAATGGCTCAA
CATGTAGAGTTGGGAAGACGACTAAGACAGCGATATATAGAGGAATTGAA
ATTTGTTGGTCCTCGGTATAATAGCCATGAAATTTATGTTAGAAGTACTG
ACTGGAATAGAACATTAACTAGTGCTATATCGAATTTTATTGGCTTCTAC
GGCCCCGGAAATGATGATGAATACCCAAAGGATTTGGGCGCAAACAAATG
GCCAGGATGGTTTTTCCCAATAGCGATACATTCACTCCCTGGAAACGAAG
ATTTTATGGCTCCTGGAGAATCGGAATGTAAACGATTTGAACAAATAAAA
GAACGGATAACTTTAACAGAAGAATACAACTCGACTTTGATTAAATACAA
ATGGCTACTCGATTTTTTGAGTGAAAAGACGGGACAGAATGTCGACCCTT
TCGATATGTGGATGATTAACGATGCTTTTTATATTGAGAAATTAAAAGGC
AAAAAATTGGTAGACTGGGCAGAGGGGAACCAAACACTTTTGGATACGAT
TGCTGAACTTGACAATTTACAAGAAAGATGGATGGTTGGGTTAGATTTAA
AACCTCTGGGTGATGCCAACTTTCGCGAAGAACTTCCAAAAATTTTGGGC
GGGCCAATCTTATGGAAATTTATAACAAATATGCAGGAGAAGTTGGCTTG
TTCAAAGCGAATGAATTCTGTAAAAGAAATTGACAGGGAAATAGAGGGAA
GAAAATCGCCAATGGGGACGCCCTTGTGTAAATGGATGAACAAAATGCGC

TABLE 2-continued

TATTTTGCGTACTCTGCGCACGACAGCACAATTATTGCAATTTTTGCAGC
TTTGGGTTTAAACAAAACGAATTATGACGAGGATGGTTACCCGAAGTATT
CTACTTGTGTAACTTTTGAATTGTGGAGGGAGAAGAATACTGGTCAATTT
GATGTTAAGGTATTTTTATGGAGACCTAACACCAACGAGACTTCCCCTAA
AGAAATAACGACAGATATTGAAGGCTGTCAAAGCAATTCAACTCTAGAAC
AATTTGTTGAAAGATCAAAAAATTATCAAATGCTGCCTTCACCCAAAGAC
TATTGTTCACAACTTCTACAACCCCTAAATAATGCTGCACGTATGTTAAT
TCAGTGGAAATTGGAAATGCTTATTCTAATGGGAATTCCTTCAATTGTTG
CTAATGTTGTATAGAGAATTTTTTTGTTTTTGGAAATTATTTAGTTGCAC
CTATTCATCAAAAGAAGGGCAAAATAAATTTTTTATCCCCTAAAAAAAAAA
AAAAAAAAAAA

>30H07>msp20>>bankit478826>>>AY134439 (SEQ ID NO: 32)

GATGCTTCAATTGACATTTAAAATTAAAAAGACCCAGGTTTCTTAATTAA
AGAATGTTTTTAAAAATTTTAACTTTCCTTTTAATTATAAACAAAATTAT
TGCGGATGATTCTAATAGCGGAGATAGTGGCAATGAAAATTCTAATAGTA
AGCCCAGTGATGAGCTTGCCGACTCTGTTGATGTTCGAGAGCATGATAAT
GAGCAACATCCATCCAATTCGATCGACAAGCAAAATCTTCAAGACCCACA
ATTTATTAAAGAAGATGTTACAAATGTATTGCCACTATTAAATAACGATG
AGAATAATCTCATTGATGAATACACAACAGAAAAAATTAAAGAAGATGAG
GAAGACCAACTAAATAATGAAGGATCTGGTATAGACAATGAATTTCCTGA
GGAAGATAATGATGTAAATGGATTGGATATTAATACAACTGCAAAATATG
CTAATGATGTAGATGATAATAATAACAATGAAGGTGATGGTCAATCATGC
GTTTATGAGGATGGTGTAATTAACGATAATGGTGACGAACGCACACCTAC
ATATGAAGAACAACAACAAATTGAAGAATATCTTCAAGAAATGCGTGAAT
TTGAAGAGCAAATGGTCAAAGACAGCGCTAATTTTATGAGAAATTTGGCA
CAATTTGTGATGAGTCAATTCGAAAACATTTTTGGTTCTTCTACCTCGTC
TCTATCAGGTAACAATAATAATTTGTTGGAGAAAAAACCTTTAGAAGCAC
CAACACCTCCTTGTTTATGCAAAAAATGTGACAGTATGACATTTATACAA
AATAAGCAAACCAAATATCTTAAAAATTTTGCTAATTAATTAACAAAAAT
TTGAAGAATAATTTAAATAATGTTTATCTCTTTCTTGAGATTTTCAAATT
ATTTAATCCATTTATATATAAATTTAAATTCATTTTCTTTTACAAAAAGC
TGAAGAGATTAAATTTTAATGTTTGAAAAAAAAAAAAAAAAAAA

>31H06>msp22>>bankit482615>>>AY134441 (SEQ ID NO: 33)

GGAATAAAAAGCGGCGAAATTTTACTTTATTCATCAAAGTACTTTAAAAT
ATTCTATAATCTAAAATGAAATTCAGCCAATTATTTGTTCTCTTAATAAT
TGCTTTACAATTTGTGGTTGCTCAAGGGTTGATTTACGATGCGAAAGCAA
TAGCCAAAGGAAAAGGAAAACCGTTCAGGGCGCTGAATATTTGGTATTTG
TCTTGGGCAACTATGTAATGAAGAAACGATATCTTTATGTAATTGATAAA
TAAAAATAACCTAAGTATCAAAAAATGTTTATGGGAAATAAAAGATTTAT

TABLE 2-continued

CTTCATTTAAAATCTAATAAATTTGTCAATCCCAAAAAAAAAAAAAAAA

AAAAAAAAAAA

>34C04>pectinase>>bankit476418>>>AF527788
(SEQ ID NO: 34)

GGTTTAATTACCCAAGTTTAAGGGGTAAAAAATGTTTTCAAGCAAAACTA

GCTTCAATTTCCTTCTTCTAATTTCTTCATTTGCTTTATGTAAGGCCGAC

TTTTGGCCTAAAGCAAGAAATAATATTACGGTATCCGAAACAATACAAAT

TACTAACCGTGACTGTAATTTTGATCGTTATATTCCCGATCCGAGTAAAC

TTGGAAACGGAGGTCAGAACGAGCATCAAGGCTACGTTTTTGAAATAAAA

AATGGTGGTTCTTTATCTAATTGTATAATTGGTGCTAGGCCTGGGACTAA

AGGCTCTGCTCATGGAGTTCTTTGTGATGGAGATTGCGATATAAACAATG

TTTGGTTTGAGGATGTTGGGGAAGATGCTATTAATTTTAATGGAGATTCT

GATGGTTGTGTTTATAATGTTAATGGTGGTGGTGCTAAGAATGGAGAAGA

CAAAGTTATGCAATTTGACGGAAAGGGGACACTGAATGTTAACAACTATT

ATGTAGACAATTATGTCCGTTTTTGTCGCTCCTGTGGCGACTGCGGTGAC

CAACATCAACGCCATATCGTGATTACTAATCTGACAGCGGTTCATGGCCA

AGCTGGTCAATTCGTTTGTGGAGTAAATAGCAATTATCAGGATACGTGTA

CCTTGCATGATATAAAAATGGAGAAGGGTATTCACCCCTGCAAGGTTTTT

GATGGCAATTCTGATGGATCTGAGCCAACTTCGAATAACGACGAAGAGGA

CCACGGAGACGGGAAATTTTGTATTTATAAGAAGGGCGATATTAAATATA

TTGGATCCAAACCAAAGCCGAAAAGCAAAAAGAGCGCAAAGAATTAAGTG

CCGGAAGTTAAAAAGCCTTGAAGTTAAAAACGTTTAAAGGGATAAATTGT

AGGGTTGTCGGTTCTGAACCGAACCGAGCCGAAGAACCGATGATTTTTCG

GTTCGGTTCCGGATATCCAAAGATTTTCCAAGAGCCGACAACCCTAGTAG

TATGAGTAGAATCTATTATTATTTGGAATACTAATTTAATTTTGTGAAAT

TTCTTTTTACTATATTAATCCTGTCCAATAAAATTATGAAATCGAAAAAA

AAAAAAAAAAAAAAAAAAAAAAA

>34D01>msp23>>bankit482619>>>AY134442
(SEQ ID NO: 35)

GGCATCAAACAATCTACTCAACAAATAAAAATCCCTAAAAACACCCCAAA

ACAACCCTAAAAGCATACCAAAAATGGCCACCTTTTTCACATTTACCCTT

CTAATCATTTCAATTATTGCCACAACTGAGGGAATGCATACTAATCGAAG

TGCTTCAACCTCCGATTCTCTCAAAGCCCAAAAGGATTGTAAAGTGATAT

ATGGAATGTTTGTGCCTGTAGCAGGGTCAGAAATGCATGGAGACGCCAAA

AGCGCAATGAAGCCAAACAATCCAAGTGTCCCCAATAAATTAACTGTATC

AGGTGGCAACTCAAAATATTCAGTGACTTTACAGGTTGAAAACCAGCCGA

AGTGTGTTGCCCAAAATGACGGAAACCCTGTAGAATGCCAAATTCAAGGA

GACAAACTTTCAGGAAAATTGATTTATGATATTGAAAACGGCCCTTCTGT

CAACGTTCCCTTCAAAGACACTCCAATCTTTGTTGGAAATAAATGCGAAA

TTGTTTTTGTAGACTACGATAAGGACCACAAATTAACTCTTTTCATGAAT

AAAGTAAAGCTTATGATTTCCCCGACTGATAAGCAAATTGTAAAGGCTTG

TGGGGTGAAAAATTAGAAAGAAAAATGATGAATGAATGAAGGTGAGAGGG

TABLE 2-continued

AAGGAAAGAAAAAATATTTTTAAAATTGAAGAAAGCATTCAAAAATTAAA

AAAAACAATTCTTCAAGATAATATATAACGTTTAACTCTTTTTGATAAAT

TTTATTTCAAAAAAAAAAAAAAAAAAAAAAA

>34F06>msp24>>bankit482623>>>AY134443
(SEQ ID NO: 36)

ATTGAAGAAGATGATACATTCAATGTTCCTGTCATGGGAGAAGAAAATCA

TAGAGATATTCCTGTCGAAGAAGCTAATTATCAAGTTCCTCCTTCTGCTG

ATTTCACTTTTACAAGCTCTGAGCATGGAAGACGTACATCATTTACAGTT

GGAACACCGCATCATCGATACATGCAACCAGGCACTCGAGAAGCATATTT

ATTGCCCCATCCAGGAGGGGAAGGTGCAACGCTTATACGCAATGAAGTTC

GTCGAGATGGAACGCAAATTTCCCAACAAGACACACTTCAAAACATTGAA

GGAGGGAGAGGTTATGTTTATTCTTCATCGTCCCACACTCAAAACGAATC

AAGTAGTAGTTCAAGAATAACTTCGAGAATTCGTTTTGGGAATAATGAAA

GACATGGGAAAAAATGAGGAATAAAGGGAAGATTTAGGAAGACATGGAAA

AAAGTGAGGAATGGAGGAAGAGATTTATACTAATTATAAAATGATAGAAA

AATTGAAGAGATATTCTCTTATTCTTTCCTATATCTTTACTTTCACATAC

AAAATTCTATAATGGCAATTTATGATTTAACATTAAAATTGAATTTAGAA

ATATTTTTTAAAATTATTTTAGTTTTCATTTTTTATCAATTTTTTGATATT

TAAATACGTCTTGTATTTATCTTCATATAATTGTTGATTAAACTTTTCTT

TATCATTCTTTTGTAGGTATTCTAAAATTAAATAATTATATGTAATATTT

TTTAATTTTCAATTTGAATAAAATTTTCTGCAAAAAAAAAAAAAAAAAAA

>35A02>msp25>>bankit478844>>>AY134444
(SEQ ID NO: 37)

GACATTCCTCAGCTTCATTACCCATCCATTTTTCATAGACAACATCCCCC

TTGCCAAACATTAAAAATTGAGTAACGCTGAATGAAGCTTTTTGTCCTGT

TAATTGGAGTTTTAGCCTTCACGGTTCTAAATGTCCATGGAGGAGTCAGC

CATTCGACATTGACTCACAGAAACCCGCGAAGCAACGAAATCGAACAATT

AACTGATGTGTCGTTGGACGATACCCCATCCTCGCCTCCTCAAGCTGTGT

TGGACATTGGAATGTCAGGACAGCGAAATTTGCAACGTCGAGAAGCTCCA

ATGTCGATTGGGAAAAAAGTGGTGGCTGTAATTTTTTTATTTCTTCTGTC

TTTTACATCGTTATATCTATTGGCCGTGCCAAAACAACAAATTCAACAAG

TTGAATACAAACAATTTCCACAACCCTATAAATTTGTTCCGATTAGTAAC

ATTGTCAAGTGCGACAGAAAAACACGGCAATGTTCAATAAAGTTAGAGAA

TTTGGATCCGACAAACAACTATAGCCTCTATACTGCAAAGAATGACAAGG

GGAGAGGAGATAAAGTAAAGTTAACTAAAGTTGCAGATATAGATTTGGAC

AAATGTCAACTCGACAAGAATGTAAAACCAGAAGTAAATGGGGAAGAAAT

TTGTAATCAGATTGTCAAAGGAATTGATGATAACGCAAAAGCCGAAACTA

TTGAGGTTAACAGTGGAGAAATAGAATTTGGTTCGGAATTAGAAGGAACG

GAGGATTATGCGATAGTTGAAAAAGCAATGAATGAGAAGAATGAACATAA

AAATCAACAAGCGGTTGAGCATGTTCATATCCCTGGGCCAGGGGAACAAC

CAGTTGAACACAATCAGCCGACAATAGAATATCCAACAAATTCCAAACAA

GTTCATCCAGCTGACAAATATCAACATAAACTAGAAGAGCGCGCCAAAAA

TABLE 2-continued

ATTTGGGCTTAGCGACTTCAAACATGGAGATTTATATGAGGATTATCGCC

AACAAAAAACGGTCCAAGAAGATGAAAAGGATAAACGATATCAAAAGGTT

CTAGGAACACTAGGAGACCATAAACATCCATCGCTAGTTGATCAATATAA

CGAAGATAAAGGAAAATTCAATCAACGTGTTAAAAGTGACCCCACAGGCA

ATAAAGTTGAAAAGGCAAAAAATTCTGATTCTAATGGACTTGAACAAAAA

TTAGAAAAACTGGCACTGAGTGACTTCAAACATGGAGATTTATATAAAGA

TTATCAGCAACAAATCACGGTCAGAGATGATGAAAAGGATAAACGATATC

AAAAGGTTCTAGGAACACTAGGAGACCATAAACATCCATCGCTAGTTGAA

CAATATAACAGAGATAAAGGAAAATTCAATCAACGCGTTAAAAGTGACCC

CACTAGCAATTGGCATGAAGATTTATTCGGAAAGGATTACCGACGTGCTA

TGAGCGATTTCGATCATTTAAAGGCTAAACAACGTGAAAAGATCCTTGGA

ACACTAGAAGATCATAAGCATCCATCGCTAATTGATCAATATAACAAAGG

AAGCTTAAATCAACGCGCTAAAAGTGACCCCACAGGCAATAATATTGGAA

AGGCAAAAAATTCTAATTTTAATGGGTCTGAACAAAAATTAGAAAAACTG

GCACTGAGTGACTTCAAACATGGAGATTTATTAGGTCGAAAAGGAGGAAT

TAAACAACGCACTATAAATGTTCTCGCTGGCAAAAAAATAGAACATGAAA

AAGGAAGTGATTTTAATGCAAACGTTGAAGAAATGATAGGGGCAGAAAAC

GGCAAGGCTAATCAAGTGAATCCCAAATTAACTGGACGCAAACTAGCTGA

ATTTAATCATATTCCAGCTGTTGACAGAATTCTTGGTTTTAAACGTGGAG

GTCATGCGCTAGAGGAGCCTCATAAAAATTGAGATATTTTGCCTGAAGAG

TTGGATTGAACGATGTATATAAGATTTTTTAACCATGTAAATATTTTTAA

AAAAGATTTTATTAGAGCCAGGAAATTACGATACTGAATCCCGAAAAATA

TCGTAATGGCTCTTAATTTTTTATTTTTTAACTTTTCCATTGCAAAGATT

TTTTTAAAATTTTTCCCGATTGTCTGGTAAACTTGTGATGAGATAAACTG

ATTTTGATTGATAATAATCGTCCATTTTCCAAAAAAAAAAAAAAAAAAAA

AAAAAAAAAA

>35E04>>bankit487871>>>AY142121

(SEQ ID NO: 38)

TACCTAAAATTGTTTTTAAATTGTTTGCCTCTGAGTTTTGCTCAACTGAG

AAGAAAAAATGCTTCCTTACTCAATTCTATTTCAATTGGGAATAGTTTCGT

TGCTTCTACCTCATGCAAATGGAATGCAGTCTGGCAGTAGCAAAATTATG

AACAAAGCATCTGAAAAGAAATATGCTTTGGTTGTTGCTCCAAACTTTCT

TAAAGTTCATTTTAAAATGAACAGTGTCTTTGCCAATGCGTTGACCAAAA

AGTTTTTTGTGCACTTTCTAATTCTGAACACCAAAAATGAAGAAATTGGA

GATAATTTCGACTATGGAATTGATCTCGAAAAATTTGAAGAAGGAACGGG

AAATACATATCAAGTTGTAAATTTTCCAGATGATTATCCCGAAAAATTGA

ACGAAGGCGTGAAGAATTTAGAGAACAAATTCATTAAGAGAGGTTACGAA

CAGAGTAGTCAAATTCTGAAAAATGAAGCTTTCACCGTTTATAAAGGTTA

AAATCCAAAATATTTTGCCTTCTAAAATTGTTATTTGATTAATAATATAT

AAAATATTTAAGATTTATTTGAAAACAATGGAGCTATTGTTCATTACTTG

AAGGAGGCAAAGTTTGATTTAGGGGTTTTTGACACTTGGGACACTGGAGC

TABLE 2-continued

TCTCTTCATTCTCCATGCAGCAGGAATTAAAAATGTTTTTGGCATTAACA

ACATTCAACTTAATGCTTATCAATTTAAATATGCTGGGAAAGAATTTCCA

AAAAATATTCCAGAAATTTATTCGGCACAAACAGGCGATAATGAATTATC

ACCACCAAGGGAAAAAAAAAAAAAAAAAAAAAAAAA

>35F03>>bankit487855>>>AY142120

(SEQ ID NO: 39)

GACATTTAATTTTTTAAATTTCTTAACATTAAATAAATTCAAAAAGAAAA

TTGAGAAAAAAAAATCTTTTAATTTAAAAAAAAAGAAAAAAGAAAAATGTA

TCCTTGGACAATTTTTCTTTTATTAATTATTTTGTTGGCTATGGCCATTG

AAATAATTGGAGGAAAAGGTCGAAAGTTAAGGAAGAGAGACAAAGAGGAA

AAAGGTCATGCCTCAATTTTCTGTTGGGCATTCATCTAGGGAAGGTTTCG

AGGAAAAGCTTGATGAAATGGTTGAATCAACTTCAAATATGTTAATAAAT

CTTGGTAAAAAAGTAAAGAAAGGAGGGAAGAAAGTTGTAAAAGGAGTTGT

AGAAACTGCGCAGCTGATCAAAAAAAAAAAAAAAAAAAAAAAAAAAAAA

>42G06>cbp>>>AF049139

(SEQ ID NO: 40)

CAAGTTTGAGCGTCAGCAATTTTAAATTAAAAAAAGACAAACTATAAAAT

CTCTCTTATTTAAAATAAGCAGTATACCCTTCAATCTATCCACAATCCAA

TAAAACTTTCTAATAAAAATCCTCCACTAAAATGGCATCCTTTTTTTATT

TCTTATTTATTTCTGTTAGTCTTTTGATTCTAGCTAATGCTGATGATGCT

GGTAGATATCCTTCAGGAGATGATTTAGTTGAAGGTACTACTGCTGCTCG

GCTTCATTCGTCTTCTGACCTACCAGACGATGATGAAGAAGAATGCGAGT

GCGAAGATGACGACGAGACAACAGTCGCAACTCACATTTCTACACGCAGC

AATGGTTACCCTTCTAATAACGGAGCCCCCACTAGCACTAAACGCCCTTC

AAACAACGGAAGCTCAAACAATGGAGGCTCAAGCTCTGTCACAGGATCTG

TTATATTGAGAGATAAATGGGTAAATGGCGCCAATTGTATTTTAGCTTTC

AAGAATAATGGAAACGCTAGAGCATGTGGTGTCAAGTTCGAGCTGACTCT

CGGTGATAATCAAAGAATCCAAAGCATTTGGAACGTTGAGAAAGTCGGAG

ATAAAGTTTACAGAATTCCGGACTACATCCAACTTGGTCCAGGAGTCGAA

AACAGAGATATTGGAGTTGTTTACAATGATGTGCCAGAACTCTTCCACAA

TCAAGGTCTTGGACAAGAAGAAGGATGCAACATTATTGAATAAAAAATAT

GGATATAAAAATATTTAAAAAAGATTAAATAAGTATTATTAAAGCTTGTG

AATATAAACTTTTTCGAAAATTAAAATAATGGCAGAAAAAAAAAAAAAAA

AAAAAAAAAA

>1C05B>msp36>>AY422829

(SEQ ID NO: 41)

TATTAAAAAAATAACAATTTCTTTTAAAAATAAAATGTATTCCCGTTCAT

CTTTAATTTCTTTTTTTCTTTTAATTAATTTAATTTTGACTCCAATGATT

TTGGCTACTAATAATGATGGTGTTGCTGCTCCGGTTGTTGCTAATAAAGA

TGCTGGGAAAGTTAGAGCGACGGAAATTATAAGAGCACTCCGTGGATTTT

GGAAAGGAGTGGCAGGTGGAGCATTGGTAGGAGGAGGTGCTGTTTTAGCT

GCACGGATATTTCGGAACGCTGGCCGGCGCGGATCGCCCCGACCCATCTG

GATGAGGTCCATCTGGATAATGGAGATGCAGCATGAGCGGTCCTCACAGA

TABLE 2-continued

CTTTCCTCGGTCGAACTGGACGCCGCGACGCTGCCGGCGGCGACCGCAGA
GATCGAGCATGAGCGCCGCGTGGCCATCTTCGATCTGGTCGAAAAGAACA
GTTTCGAGCCGGTCGGCGCCGAGGGCGGCCCGTATCAGCTGAAGCTGTCG
CTGCAGGACAACCGGCTGGTGTCCGGCTAAATTCGCATTTAAGGAAATTC
GATGTTTTTAATAATTTAATTTAATAAATTTGTTTTATCTTTAAAAAAAA
AAAAAAAAAAAAAAAA

>1C11B>eng-1>>AF100549

(SEQ ID NO: 42)

ATTAATTTTAAAAATCTAATTAAAAATGAATTCTCTCTTATTAATAGCAT
TTTTATCCCTCTCATTTTGTGTTCCAATAAAGGCTGCTCCTCCATATGGG
CAATTATCTGTGAAAGGAAGTCAATTAGTGGGCAGTAATGGACAACCAGT
TCAACTTGTTGGAATGTCACTTTTCTGGTCGAGTTGTGGTGAAGGAGAAG
TTTTTTATAATAAAGCAACAGTAAATAGTCTTAAATGCTCTTGGAATTCA
AATGTAGTTAGGGCTGCAATGGGTGTAGAGTATTCAGGGTGCCAACGACC
AGGTTATTTGGATGCCCCAAATGTTGAGCTGGGCAAGGTTGAAGCTGTTG
TTAAGGCCGCAATAGAGTTGGATATGTATGTTATCCTTGACTTTCACGAC
CACAATGCTCAACAACATGTGAAACAAGCTATCGAATTCTTCACATATTT
TGCCCAAAACTACGGATCTAAATACCCTAACATAATCTATGAGACTTTCA
ATGAGCCACTACAAGTAGACTGGAGTGGTGTAAAGTCATATCATGAGCAA
GTTGTTGCAGAAATTAGAAAATATGACACAAAGAATGTCATCGTTCTCGG
TACAACAACATGGTCTCAGGATGTCGATACTGCTGCTAACAATCCTGTAA
GCGGCACAAACCTTTGCTACACTCTACACTTCTACGCAGCAACTCATAAA
CAAAACATAAGAGACAAGGCGCAAGCTGCAATGAATAAAGGAGCTTGTAT
CTTTGTAACTGAATACGGAACTGTTGATGCAAGTGGAGGTGGTGGAGTGG
ATGAAGGTTCGACAAAAGAATGGTATAACTTCATGGATAGTAACAAGATT
TCTAACCTCAACTGGGCTATCTCAAACAAGGCAGAAGGTGCTTCAGCACT
CACATCTGGAACGAGTGCTTCTCAAGTTGGCAATGATGACCGATTGACTG
CCTCCGGTGTTCTAGTGAAGAAGTATATTAAATCAAAGAATACTGGTGTC
AGTTGCAATGGTGCATCACCAGGCAGTGGTTCAGGAAGTAACCCCTCAGG
AAATAAACCGAGCAACTCACAAACCAGCACTGCCAAAACATCAAGCAATT
CAGGAAATAAAGGCGGTAATTCTAACACAGGGAATAATGCAAATAACTCA
GGAAGTAAACCGGGCAACTCCGGAAGTAATACAGGAAATACGGGTAGCAA
TGCCGGAGCCAGTTCAGGAAATACGGGGACCAGTACAAGCGGTAGTTCTG
TTACAGCTTCAGTACAAGTTCCCGATAAATGGGATAATGGCGCAAGATTC
CAATTAGTATTTAAAAACAATGCAAGTACAAAAAAGTGTGCAGTGAAATT
TTCATTGACTTTTGCCTCTGGACAACAAATTACTGGCATTTGGAACGTTC
AAAATGTAACAGGAAATAGTTTTGTTCTTCCAGACTACGTTACAATTGAG
GCAGGGAAACAATATACAGATGCAGGAATGAATATAAATGGGCCAGCAAC
TCCTCCACAAATTAAGGTGCTCGGCGATGGAAAATGCGTTTTTTGAAATT
AAAGACTCCGTCTTAATTGTTGAATTATTTTAATCTTATGATTGTTTAAA
TTGGAAAAAAAATATATGTATAATTTGCTTCTGTTAATTTTGTTTATTTTA
AATATACGATAAAAATTA

1D08B>msp37>>AY422830

(SEQ ID NO: 43)

TAAAAAATGATTTTTATTTCCTTAATTATCCTCGTATTGGCTGCTGAATC
TAATGAAGCAAGCACAAACTGCAAGGATGGTGAAGGCGCGGTAACCTTCT
TGTCCAACCAGCTCGGTAACATACAGGGAATAAAAGGAAATAGTTATTAT
AACAAAACTTGTTCCAACAAAAATACTGCAAAACGTTGCTACCCAAATGA
TGAATCAAATATTAGCGTTTTTAAAATTGTTTGCCCCACAAATATTTGTA
TTTGTGGTAATGTTGATAATCAATGTTACTCTGCAAAAACAGTTAATCCT
GGAGATTTAGACTATATGTTCTATTCTCATAGTGGCAGCATGTTTGTTAA
CCCAAATGTTGGTTCAATTTCATTATCGTCACCTGATAATCATTATTTTG
ATCCAAAGACTAGTGCCCCAAAATTCATGGAATTAACCCCAGGCACAAAA
TCATATCTTAATGGGAATGAGCTTTCTGTTGCTTGTACATCTTGTGCTAA
CTTTAAGCAGCTAACGTGTTGAACAATAAAAAAAAAAAAAAAAAAAA

2B02B>pel2>>AY327873

(SEQ ID NO: 44)

GAAAATAAATTATTCTTTTTAAAATTATCAAAAAATGCCACATTTTTATT
TAAAATTTTTAATTAATTTAATTTTATTAAATTTATTCCCATTACTTATA
AAAAGCGATTTGTGTAAATTTCCAACGGCTAAGGGGAACCAAACTGTTGA
TGAAACAATACCATTAAATAAAGATAAAGATTTTGGGTTTATTCGTCTGA
TAGCTTCTCCAAAGTTGGGAAGTTGTACAATTGACTTTAGTAAGAAAATG
TCGCCAATATTATGGTTATCCGATGGGGTGACTGTTAGTAATTTAATTAT
TGGAACTGAATCTTCTTCAGGCATTTGGTGTAGTGGAAGTTGTACCTTGA
AGAATGTCTATTTTGAACGTGTTTGTACTCACGCCGCAGCTTTTAATGCA
ACAACAGACTTTACAAAAACTGATAGACGTTCATTTACATATACAGTTGA
GGGGGGCGCTGGACTCCATGCTTTAGATAAAATGTTTGTACAATCTGGCC
CCGGAAAGACAATAATTAATAATTTTTGTGGGGATGGATTCCAAAAAGTT
TGGCGATCGTGTGGGACGTGTAATGATGAAGTGAGTCAAAATTCTAAACA
AAGAACTGTTACTATAACAAATTCAAATTTTACTGGCAAAGGACATGTAA
TTGCATCTGGAAATGCCCCTTATAAAGACAAAGTTTCCTTCAATAATGTC
AAAATATTTGGTTATAAAAATCGTTCAACAAGAGTTGTTTATGCCTGTGG
GGAAGTTAAACCAGAAATAAGTGAAGATCATTTAGATACAGGAGCTTCAA
ATTGGTATATACCTGGACGTGCTGGTACTGGAACTGTTTGTAATTATCCC
GCTTCAGCAGTTAAAATTGTTAATTAAACATTAAAAGCTTGATATTTAGA
AAATAGTAATAATAAATGTTATTTATTGTGAATAAAGTTTTATAATTAAA
AAAAAAAAAAAA

2G06B>cm1>>AY422834

(SEQ ID NO: 45)

GGTTTAATTACCCAAGTTTAAGACAATAAACTTTTTAATAAAAATATTTA
ATTTTGAATGTCTTTGAATTGGCTTTATTGCAATTTATTTATTGTAATAC
TCCTTTTCAACATTGTAAAGAGTGATACCGATACTAATGCTGATATTGAT

TABLE 2-continued

CGATTTGTTGAAATTGCAGACGATCGTTTAACTCTTTCTGATTATGTTGC

TTTATATAAAATTGTTAATAACAAAAGTATTACTGATCCAAAACGAGAAG

AAAAACTTTTGAACGATATGAGAAGTAAGGGAAAGAATCTTTCGTTAAAT

GAGGATTATGTTACTTTAATATTCCAAGACCAAATAAATGCTAGTAAATA

TTTTCAGAATTATTTGGTTAATTTATGGAATCAATCAGGCATTCCACCTA

TTAAAGTTCGAGATTTAAATACAGACTTACGCCCAGCAATTGATCAAATA

AATACAGAAATGCTGCAATTGCTAGTTAAAATACAAAAACTTCCCTCCAA

AGATTGTTTAAAAAAAGTAGATAAGTCTGTAAATAATTTTATTATGAGAG

TTAATCAAATTGATGAACAAAATGATGCTTTGAAAATGGCTGTGAAAGGC

AAAGACCTCTGCCCTGCATGTAAACATAATTAACGTTTAGTTAATTATAA

AGGGAAAAGAAATTATAATTTTGAAAAAATTTTGGGTTTCACCAAAAAAA

AAAAAAAAAAAAAAAAAAAA

4F05B>msp38>>AY422831

(SEQ ID NO: 46)

AATACACAAAAACTATTTTAAAAAAGGCACTAACTTAAATAATGACTTGT

AGTATTAATATTTTTATTATTTTATTTATTACATTAATTATTGGAATATG

CACGGAGGCAAAAATCCGTAAACAATTTGTTGACTCTCCACAGGAACCAC

AAGCTAAATCGGTTGATTTGAATTTGCAAGTTTTAATCTTTATAAAAAGA

TGCAAATCACAATTATGGGCAGTTGGGTTAAATAATTATAAAACACAATT

TCCAAACTGCTCATTAATTGAGGAAATATATTCTCGTCATTATCCTTTTG

GAATGTTAAAAACTACACAATGGTTATTACAAACACTTCTTTTATTTTCT

GCAATGTATTTTCCATATTTTGAAGTTCATGATATATCTTTGGTTGTTTT

TTTCACCCTGCAATTTTCAGTTTTATTCACTGGCTTTTATATTATTGCGC

AGTTCATGAAAGTCAAAATAATCCAAAACCAATTAATTTGTCTACTCTCT

TCTTTTCTGATATAATCATTTCATATTGCTTCACTATATTATTTATTGTA

CAGTTTATATCATCAGGAAGATATGGGGCATATTTGTTTCTCTTTGGATT

AATTTTGTATGGTGGTTATTCTTTAATTTTAACTTTTGTTTATTTACGTA

ATAATGAAGATGGATCCTTTAAATTCCCAATTTCAATAAAAATAAATGTT

GAAATTATTCAAAAATCGGATAAAGAATTAAAACAGGAAAAAAAAAAAAA

AAAAAAAAAAAA

5A12B>eng3>>AY422836

(SEQ ID NO: 47)

GACAACACAAATCAAATTAATTTTAAAAATCTAATTAAAAATGAATTCTC

TCTTATTAATAGCATTTTTATCCCTCTCATTTTGTGTTCCAATAAAGGCT

GCTCCTCCATATGGGCAATTATCTGTGAAAGGAAGTCAATTAGTGGGCAG

TAATGGACAACCAGTTCAACTTGTTGGAATGTCACTTTTCTGGTCGAGTT

GTGGTGAAGGAGAAGTTTTTTATAATAAAGCAACAGTAAATAGTCTTAAA

TGCTCTTGGAATTCAAATGTAGTTAGGGCTGCAATGGGTGTAGAGTATTC

AGGGTGCCAACGACCAGGTTATTTGGATGCCCCAAATGTTGAGCTGGGCA

AGGTTGAAGCTGTTGTTAAGGCCGCAATAGAGTTGGATATGTATGTTATC

CTTGACTTTCACGACCACAATGCTCAACAACATGTGAAACAAGCTATCGA

ATTCTTCACATATTTTGCCCAAAACTACGGATCTAAATACCCTAACATAA

TABLE 2-continued

TTTATGAGACTTTCAATGAGCCACTACAAGTAGACTGGAGTGGTGTAAAG

TCATATCATGAGCAAGTTGTTGCAGAAATTAGAAAATATGACACAAAGAA

TGTCATCGTTCTCGGTACAACAACATGGTCTCAAGATGTCGATACTGCTG

CTAACAATCCTGTAAGCGGCACAAACCTTTGCTACACTCTACACTTCTAC

GCAGCAACTCATAAACAAAACTTAAGAGACAAGGCTCAGGCTGCAATGAA

TAAGGGAGCTTGTATCTTTGTAACTGAATACGGAACTGTTGATGCAAGTG

GAGGTGGTGGAGTGGATGAAGGTTCGACAAAAGAATGGTATAACTTCATG

GATAGTAACAAGATTTCTAACCTCAACTGGGCTATCTCAAACAAGGCAGA

AGGTGCTTCAGCACTCACATCTGGAACGAGTGCTTCTCAAATTGGCAATG

ATGACCGATTGACTGCCTCCGGTCTTATAGTGAAGAAGTATATTAAATCA

AAGAATACTGGTGTCAGTTGCAATGGTGCATCATCAGGCAGTGGTTCCGG

AAATAACCCCTCAGGAAATGAACCGAGCAACTCACAAACCAGCACTGCCA

AAACATCAAGCAATTCAGGAAATAAAGGCGGTAATTCTAACACAGGGAAT

AATGCAAATAACTCAGGAAGTAAACCGGGCAACTCCGGAAGTAATACAGG

AAATACGGGCAGCAATGCTGGGGCAAATTCAGGAAATACGGGGACCAGTA

CAGGCAGTAGTTCTGTTACAGCTTCTGTGCAAGTTCCCGATAAATGGGAT

AATGGCGCAAGATTCCAATTAGTATTTAAAAACAATGCGAGTACAAAAAA

GTGTGCAGTGAAATTTTCATTGACTTTTGCCTCTGGACAACAAATTACTG

GCATTTGGAATGCCCAAAATGTAACAGGAAATAATTTTGTTCTTCCAGAC

TACGTTACAATTGGAGCAGGGAAACAATATACAGATGCAGGAATGAATAT

AAATGGGCCAGCAACTCCTCCACAAATTAAGGTGCTCGGCGATGGAAAAT

GCGTTTTTTGAAATTAAAGACTCCGTCTAAATTGTTGAATTATTTAATCT

TATGATTGTTTAAATTGGAAAATAAATATATGTATAATTTGCTTCTGTTA

ATTTTGTTTATTTAAATATACGATAAAAATTAAAAAAAAAAAAAAAAAAA

AAAAAA

5C03B>msp39>>AY422832

(SEQ ID NO: 48)

TAAATTTCTTCCCTAAAATTTATTTAAAATTTTATAACAAAAAAATGTTT

TCAATTCAAGGATTATCTTCTTTTCACTTCATTTTCCTCTCATTATTGAT

ATTATTGCAAAACTCTTCTACTGTATTTTCTCAACTTGGTTGTGATTATG

GATCAATGTATGGCGGGGGAATGAGTGGTTATGGCCAAGCAGGTTATGGA

AATGAAAGTACACACATCACTTCTGCCCACATTATATTGGCCAAAGTGAA

TCACATGGTTTCTCCTGACTTCAACAAGCAGGGCATGAATAATCTAACCT

CCCACAAAGAACACGACTAGGAAAGAAAATAGAATAATTGGCAAACACTA

ATGCAATCTACTACAGAAGTCAATGGAGAATTTACCTCCTAAACAGGAAA

ATGATTTGTGCCTAAAAGGAAGGAAGAAGAACCTCCTCTTTGTTGAGGGG

AAAAGTCCATAACACAGGAGTGCTTGGACCCAAGTACACAAATATAAGAA

CCCTTCTAGGAAAACACGAGCTGGGGAAGCAGTTTCTCTTTGCTATTTTG

TGAGAAAATAAATGCCAAAAAAAAAAAAAAAAAAAAAAA

6D09B>cm2>>AY422835

(SEQ ID NO: 49)

GGTTTAATTACCCAAGTTTAAGAAAATAAACTTTTTAATAAAAATATTTA

TABLE 2-continued

ATTTTGAATGTCTTTTAATTGGCTTTATTGCAATTTATTTATTGCAATAC

TCTTTTTCAACATTGTAAAGAGTGATACCGATACTAATCCTGATATTGAT

CGATTTGTTGAAATTGCAGACGATCGTTTAACTCTTTCTGATTATGTTGC

TTTATATAAAGTTGTTAATAATCAAAGTATTACTGATCCAAAACGAGAAG

AAAAACTTTTGAACGATATGAGAAGTAAGGGAAAGAATTTTTCGTTAAAT

GAGGATTATGTTACTTTAATATTCCAAGACCAAATAAATGCTAGTAAATA

TTTTCAGAATTATTTAGTTAATTTATGGAATCAATCAGGCATACCACTTA

TTAAAGTTCGAAATTTAACAACAGACTTACGCCCAGCAATTGATCAAATA

AATACAGAAATGCTGCAATTGCTAGTTAAAATACAAAAACTTCCCTCCAA

AGATTGTTTAAAAAAAGTAGATAAGTCTGTAAATAATTTTATTATGATAG

TTAATCAAATTGATGAACAAAATGATGCTTTGAAAATGGCTGTGAAAGGC

AAAGACCTCTGCCCAGCATGTAAACATAATTAACGAAAAAAAAAAAAAAA

AAAAAAAAAA

8E08B>eng4>>AY422837

(SEQ ID NO: 50)

ACGCGGGGAACACAAATCGAAATATTTTTAAAAATTTAATTAAATGTTTT

CCCTCTCATTAGTAGCATTTTTATCCCTCACATTTTGTATTCAAATTAAT

GCTGCTCCTCCGTATGGGCAATTATCTGTGAAAGGAAGTCAATTAGTGGG

CAGTAATGGACAACCAGTTCAACTTGTTGGAATGTCACTTTTCTGGTCGA

GTTGTGGTGAAGGGGAAGGTTTCTATAACAGAGAAACTGTAAATAGTCTT

AAATGCTCTTGGAATTCAAATGTTGTTAGAGCTGCAATGGGTGTAGAATA

TTCTGGATGCCAACGACCAGGTTACCTTGATGCCCCAAATGTTGAGCTGG

CAAAGGTTGAAGCTGTAGTGAAGGCGGCGATTGAGTTGGATATGTATGTT

ATTCTTGATTTTCACGACCACAATGCTCAGGGTCATGTGAAACAAGCTAA

ACAATTCTTCGCATATTTTGCCCAAAACTACGGATCTAAATACCCAAATA

TCATTTATGAGACTTTCAATGAGCCACTACAAGTAGACTGGAATGGTGTA

AAATCATATCATGAGCAAGTTGTTGCAGAAATTAGAAAATATGACAATAA

GAATGTCATCGTTCTTGGTTCAACAACTTGGTCTCAAGATGTTGATACTG

CCGCTAATAATCCTGTACGAGGTTCAAACCTTTGCTATTCTTTACACTAC

TACGCAGCAACTCATAAACAAAACTTAAGAGACAAGGCACAGGCTGCAAT

TAATAAAGGAGCCTGTATCTTCGTAACTGAGTACGGAACCGTTGATGCAA

GTGGAGGTGGTGGAGTGGATGAAGGCTCGACAAAAGAGTGGTATAACTTC

TTGGATAGCAAGAAAATTTCTAACCTCAACTGGGCTATCTCGAACAAGGC

AGAAGGGGCTGCAGCACTCACCCCTGGAACGACTTCTTCTCAAGTTGGCA

TABLE 2-continued

ATGATGACCGATTGACTGCCTCCGGTCGTCTAGTGAAAAGTTATATTAAA

TCAAAGAATACTGGTGTCAGATGCAATGGAGGGGGTGCTGCAAAAAAAGG

CTCTTCATCATCTAATACTGGTTCAAAAAAAGACAAACAAAAATTCAAAG

AACAAAAATTCAAAGAAAAAATCTAACAACGCCAAACTGCCGAAAAAAAG

GTCCCAAAAAGAACACTTAGACAAATATCAAGGAATTTAATGTTAAATGG

AATATAATTGTTTTAAATTAAAAAAAAAAAAAAAAAAAAAAA

8E10B>msp40>>AY422833

(SEQ ID NO: 51)

GGTCATTCTTATAACTAAAAACCTTCAAACTTCAAAAAATATTCCTTAAA

CTTCTTCAGAAAAATAATTGAAAAATGTTATTAAAATTCTTTTTCCCATT

ATTGCTTTTGCTTACCCTTATCTATTTGGGTTGTTCTGAGGAGGATAAGG

GAGACATTGCAAATGGTCCTCAGGAATCTGAGAATCAGGTTGATCAAGAA

TTGGTTAGATTGAAAAGAGATGATGAAGAAGAGGAGGGAGAGAAGGCCGA

AGATGAAGAGAAGGCTGAAGAGGATGGAGATAAAGCTGAAGATGCTGAGA

GTGCAGAGGAGGGAGATAAGGCTGAAGATGCTGATGAGGGAGAAAAAAAG

AGTGAAGATGAAGAGAAAAAGAGTGAAGGTGACGAAGAAAAAGCGGAAGG

TGAAGAGGAAGAAAAAAAGGATGGAACTGAGGAAGAAAAGGAGGATGAAG

ATGAAGAAGAGAAAAAAGATGATGATGAAGAAAAAAATGAGGAAGAAGAA

AAAAAGGATGACGAAGAAGAGAATGGAGATAAAGAAGAAAAGAAGGATGA

TACGGAAGAGAAAGAGGATAAACACACAAAGGATAAAAGTAAGAAGAAGG

ATAGTAAGTCCGTTCAAAAGGATAAAAAGGAGGAAGATGACAAGGAGAAA

AAGGAAAAAAGTTCAAGTGGTGATAATTCTAAAACAGATAAATCACAAAA

TCAAAAACAAAGCAAAGAATCATGTAATGGGGATACTGCTTACAACTGTC

CTAAACTATCAGGTCTTTGTGAATCAAAAATTCAAGTACAACAAGACTTC

ATGGGTGAAAAATGTTGTGCTACGTGCAAAAATTCGGCTCCTGCTGCGAA

GAAAGATATACCCCTATGCACTGATTTGGCTGATAATTGTGATCAAATAG

CATCCACCTGTGGGGAAGAGGCGTGGCAACCGACTATGATTTCTGATTGT

GCTGAGACCTGCGATAAGTGTGAATTACATTTTCAAATGTTGGAGAAGAG

ACTTGCAGCAGCTGCTGCTTAAAATTTTGAAAGGAAAAGAATTTTATCAA

AAATATATGTGTATCATATTCACTAAGCAAGAAATTTTCTTTGATTTTCA

CACCTTTAATACGTAAAATTTCAATCTATTCATCCGTGTTTCTCGTAATT

ATGTTTTATTAATTTTTTCGAAATTTAGTAAAAATGCCTCCAAAAAAAAA

AAAAAAAAAAAAAAAA

What is claimed is:

1. A transgenic plant or transgenic plant cell comprising:

an inhibitory dsRNA specific for mRNA of a protein encoded by SEQ ID NO:1 or 2 or a complement thereof, wherein the dsRNA is present in an amount effective to provide resistance to parasitic nematode disease or infestation caused by at least two different nematode species, and wherein the dsRNA comprises at least 21 contiguous nucleotides.

2. The transgenic plant or transgenic plant cell of claim 1, wherein the transgenic plant or transgenic plant cell is resistant to nematode disease caused by *M. incognita.*

3. The transgenic plant or transgenic plant cell of claim 2, wherein the transgenic plant or transgenic plant cell is also resistant to nematode disease caused by *M. javanica.*

4. The transgenic plant or transgenic plant cell of claim 3, wherein the transgenic plant or transgenic plant cell is also resistant to nematode disease caused by *M. arenaria.*

5. The transgenic plant or transgenic plant cell of claim 4, wherein the transgenic plant or transgenic plant cell is also resistant to nematode disease caused by *M. hapla* or *M. chitwoodi.*

6. The transgenic plant or transgenic plant cell of claim 1, wherein the nematode is a member of *Meloidogyne* spp.

7. The transgenic plant or transgenic plant cell of claim 1, wherein the transgenic plant or transgenic plant cell is a monocot or dicot.

8. The transgenic plant or transgenic plant cell of claim 1, wherein the transgenic plant or transgenic plant cell is a member of the phylogenic family selected from the group consisting of Rosaceae, Fabaceae, Passifloraceae, Cucurbitaceae, Malvaceae, Euphorbiaceae, Vitaceae, Solanaceae, Convolvulaceae, Rubiaceae, Leguminosae, and Brassicaceae.

9. The transgenic plant or transgenic plant cell of claim 8, wherein the transgenic plant is a tomato, eggplant, potato, melon, cucumber, carrot, lettuce, artichoke, celery, cucurbits, barley, corn, peanut, soybean, sugar beet, cotton, cowpea, beans, alfalfa, tobacco, citrus, clover, pepper, grape, coffee, olive, or tea.

10. The transgenic plant or transgenic plant cell of claim 1, wherein the dsRNA induces or promotes the degradation or mRNA encoding the nematode polypeptide encoded by SEQ ID NO:1 or 2.

11. The transgenic plant or transgenic plant cell of claim 1, wherein the transgenic plant or transgenic plant cell comprises two or more dsRNAs specific for mRNA encoding different nematode esophageal gland cell polypeptides.

* * * * *